(12) United States Patent
Huang

(10) Patent No.: US 8,053,583 B2
(45) Date of Patent: Nov. 8, 2011

(54) ANTI-CANCER COMPOUND AND MANUFACTURING METHOD THEREOF

(75) Inventor: Hsu-Shan Huang, Taipei (TW)

(73) Assignee: National Defense Medical Center, Taipei (TW)

( * ) Notice: Subject to any disclaimer, the term of this patent is extended or adjusted under 35 U.S.C. 154(b) by 146 days.

(21) Appl. No.: 12/399,935

(22) Filed: Mar. 7, 2009

(65) Prior Publication Data

US 2010/0145070 A1 Jun. 10, 2010

(30) Foreign Application Priority Data

Nov. 28, 2008 (TW) .............................. 97146185 A

(51) Int. Cl.
C07C 233/33 (2006.01)
C07D 207/10 (2006.01)
A61K 31/167 (2006.01)
A61K 31/40 (2006.01)
A61P 35/00 (2006.01)

(52) U.S. Cl. ...................................... 548/528; 552/260

(58) Field of Classification Search ........................ None
See application file for complete search history.

(56) References Cited

U.S. PATENT DOCUMENTS

| 6,596,774 | B1 * | 7/2003 | Huang | 514/676 |
| 6,777,564 | B2 * | 8/2004 | Lee et al. | 552/261 |
| 2003/0008316 | A1 * | 1/2003 | Smith et al. | 435/6 |
| 2005/0009924 | A1 * | 1/2005 | Huang | 514/649 |
| 2006/0148777 | A1 * | 7/2006 | Smith et al. | 514/183 |
| 2009/0253709 | A1 * | 10/2009 | Huang | 514/252.11 |

FOREIGN PATENT DOCUMENTS

| JP | 50-138021 | * | 11/1975 |
| WO | WO 91/00265 | * | 1/1991 |
| WO | WO 98/25884 | * | 6/1998 |

OTHER PUBLICATIONS

Huang, Hsu-Shan et al., "Synthesis and Antitumor Activity of 1,8-Diaminoanthraquinone Derivatives", Chemical and Pharmaceutical Bulletin-Tokyo, 53(9), 1136-1139, 2005.*
Huang, Hsu-Shan et al., "Synthesis and Human Telomerase Inhibition of a Series of Regioisomeric Disubstituted Amidoanthraquinones", Chemical and Pharmaceutical Bulletin—Tokyo, 55(2), 284-292, Feb. 2007.*
Perry, Philip J. et al., "Human Telomerase Inhibition by Regioisomeric Diamido Anthracene-9,10-diones", Journal of Medicinal Chemistry, 41(24), 4873-4884, 1998.*
Keppler, Melanie B. et al., "Stabilization of DNA Triple Helices by a Series of Mono and Disubstituted Amidoanthraquinones", European Journal of Biochemistry, 263, 817-825, 1999.*
Agbandje, Mavis et al., "Anthracene-9,10-diones as Potential Anticancer Agents. Synthesis, DNA Binding, and Biological Studies on a Series of 2,6-Disubstituted Derivatives", Journal of Medicinal Chemistry, 35(8), 1418-1429, 1992.*

* cited by examiner

*Primary Examiner* — Fiona T Powers
(74) *Attorney, Agent, or Firm* — Ming Chow; Sinorica, LLC

(57) ABSTRACT

Anti-cancer compounds and manufacturing methods thereof are disclosed. The anti-cancer compounds are 1,8-diamidoanthraquinone derivatives with amino compounds. The manufacturing method includes the steps of: add 1,8-bis (chloroacetamido)anthraquinone or 1,8-bis(3-chloropropionamido)-anthraquinone with amino compounds, catalysts, and dehydrated dimethylformamide (DMF) to form a mixture and react with one another. Then by purification and recrystallization, the anti-cancer compounds are obtained. The anti-cancer compounds of the present invention are compounds with whole new structure that overcome serious cardiac toxicity of the conventional anti-cancer drug-doxorubincin.

1 Claim, 14 Drawing Sheets

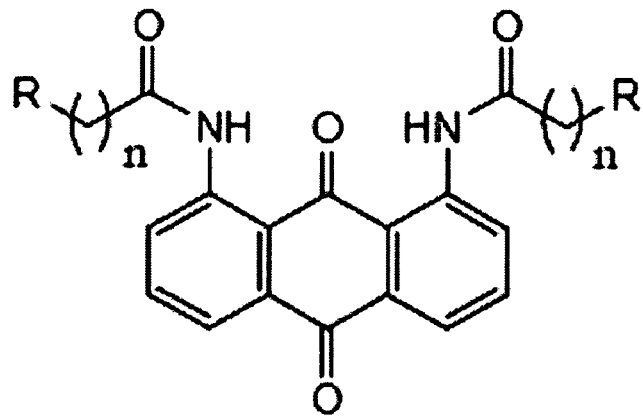

If n=1, R=NHCH$_2$CO$_2$CH$_3$、NHCH(CH$_2$CH$_2$SCH$_3$)CO$_2$CH$_3$、
N(CH$_2$CH$_2$CH$_2$CH$_2$)CO$_2$CH$_3$、NHCH(CH(CH$_3$)$_2$)CO$_2$CH$_3$、
(D)-NHCH(CH(CH$_3$)$_2$)CO$_2$CH$_3$、N(CH$_3$)CH$_2$CO$_2$CH$_3$、
NHCH(CH$_2$CH(CH$_3$)$_2$)CO$_2$CH$_3$、NHCH(CH$_3$)CO$_2$CH$_3$、
(D)-NHCH(CH$_3$)CO$_2$CH$_3$、NHCH(C$_6$H$_5$)CO$_2$CH$_3$、
NHCH$_2$CH(CH$_3$)$_2$、N(CH$_2$CH$_3$)$_2$、N(CH$_3$)$_2$、
N(CH$_2$CH$_2$CH$_3$)$_2$、NHCH(CH$_3$)$_2$、NHCH$_2$CH$_3$、
3-(CF$_3$)C$_6$H$_4$CH$_2$NH、N(CH$_3$)CH$_2$CH$_3$、
N(CH$_3$)CH$_2$CH$_2$CH$_3$ or NHCH(CH$_2$OCH(CH$_3$)$_3$)CO$_2$CH$_3$.

n=2, R=N(CH$_2$CH$_3$)$_2$、NHCH$_2$CH(CH$_3$)$_2$、3,5-F$_2$C$_6$H$_3$CH$_2$NH、
NHCH$_2$CH$_2$NHCO$_2$C(CH$_3$)、NHCH$_2$CH$_2$N(CH$_3$)$_2$、
N(CH$_3$)$_2$、N(CH$_2$CH$_2$CH$_3$)$_2$、NHCH$_3$、NHCH(CH$_3$)$_2$、
NHCH$_2$CH$_2$CH$_2$N(CH$_3$)$_2$ or N(CH$_3$)CH$_2$CH$_3$.

Fig. 8

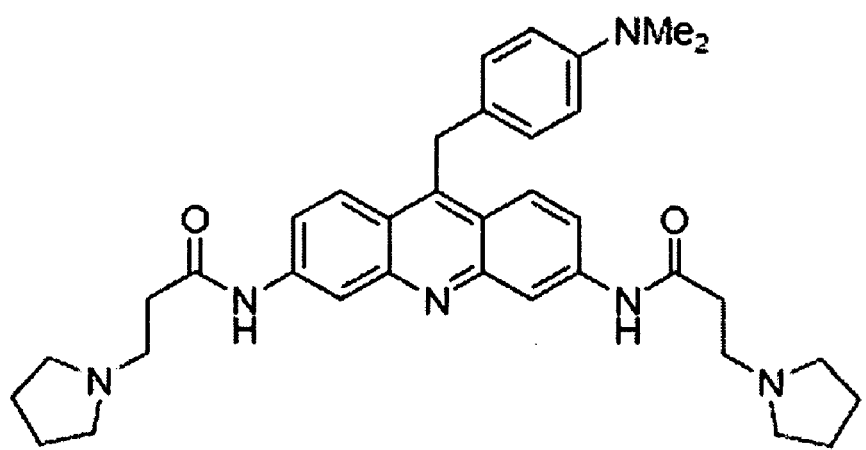
BR-ACO-19
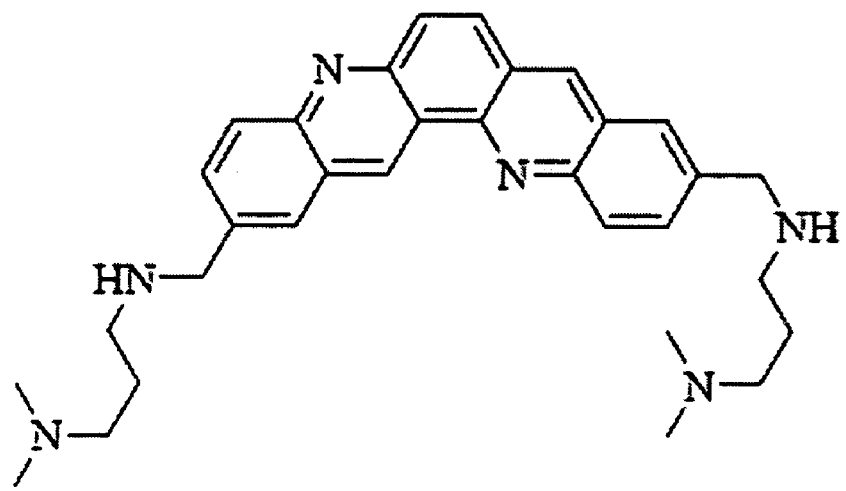
dibenzo[b, j](1,7)phenathroline
Fig. 14

ANTI-CANCER COMPOUND AND MANUFACTURING METHOD THEREOF

BACKGROUND OF THE INVENTION

1. Field of Invention

The present invention relates to a series of compounds that inhibit tumors, being applied to tumor suppression.

2. Description of Related Art

A telomere is a region of repetitive DNA at the end of chromosome which protects the end of the chromosome from fusion and recombination with other chromosomes that may lead to structure change so as to keep chromosome stability and integrity. In the end of 1930s-1938. Muller, researchers that study genetic inheritance in fruit flies, found that chromosomes broken by external forces such as X-ray were unstable and had chromosomal rearrangements. In 1941, McClintock found genetic instability in hybrid corn with broken ends of chromosomes. Thus Muller said that in the end of the chromosome, there is a functional region without important genetic message and involved in chromosome stability and named it in Greek as Telomere (Telos : end ; meres ; part). The sequence of telomere was not found until 1978 when Blackburn found repeated sequence TTGGGG (SEQ ID NO: 1) in a flagellate called Tetrahymena. Later sequences of telomeres in other creatures were also provided. In eukaryote, repeated DNA sequence with a lot of Guanine is on two ends of the chromosome. As to human telomere, it has been shown to consists of a tandem array of 5-15 Kb of the simple repeat (TTAGGG)n (SEQ ID NO: 2) by Moyzis et al. in 1988. Moreover, there are at least two proteins-Telomeric repeat binding factors-TRF1, TRF2 bound with a T-loop that is formed by single strand of telomere DNA held together by telomere binding proteins. In fore-end of the T-loop, (both strands of the chromosome which are joined to an earlier point in the double-stranded DNA by the third stand end invading the strand pair to form a D-loop.)
the two strands of a double-stranded DNA molecule are separated for a stretch and held apart by a third strand of DNA that pairs with one of the strands so as to form a triple-stranded DNA called D-loop or displacement loop.

Generally, chromosomes DNA in eucaryotes is linear. In semiconservative replication, primase synthesizes a primer that is complementary of the end of a parent DNA. Then a DNA polymerase starts replication of a daughter strand. When the replication is over, the primer will have to be removed by another polymerase. An enzyme-ligase that joins DNA synthesizes new molecules to fill gaps in DNA. Yet a 5' end of the daughter stand is unable to be filled so that an end replication problem is raised. Each DNA replication, end of DNA (telomere) loses 50-150 bp. Now a plurality of studies show striking correlation between the length of telomere and the times of cell division. When the length of telomere is shortened to a certain degree, cells become senescence or death. That means that telomeres loss may act as a mitotic clock. However, germ cells and tumor cells are different from normal somatic cells and their proliferative capabilities are unlimited. This means these cells must overcome senescence problems and have some mechanisms that maintain the length of telomere. Such mechanism is related to reactivation of telomerase.

The telomerase is a specific ribonucleoprotein reverase transcriptase inside human bodies that synthesize repeated sequence (TTAGGG)n (SEQ ID NO: 2) on the end of telomeres to extend the length of telomeres.

This enzyme consists of two subunits-telomerase RNA and telomerase catalytic subunit (hTERT). The hTR containing RNA includes repeated 11 nucleotides-5'-CUAAC-CCUAAC-3' (SEQ ID NO: 3) that is complementary to TTAGGG (SEQ ID NO: 2) of telomere and is used as replication template to extend the length of telomere. As to the telomerase catalytic subunit, abbreviated as hTERT, it is a main catalytic subunit. Moreover, there are some other structure proteins such as TEP1, Dyskerin, p23, hsp90, L22 and hStau are used to stabilize the telomerase. Thus the telomerase uses RNA as template to produce a segment of DNA with the same sequence of telomere that connects with a 3' end of the chromosome under the catalysis of the subunits of the reverase transcriptase so that the chromosomes will not be shortened progressively after replication and cells will continue to divide.

It is found from a plurality of studies that normal somatic cells express undetectable levels of telomerase while in highly proliferative cells such as germline cells, hematopoietic cells, trophoblast, endometric cells and over 85%~90% tumor cells, telomerase is highly expressed. Thus expression of telomerase is an important characteristic of tumor cells. According to nature of tumors, it is found that in malignant tumors, high telomerase activity represents immortalization of tumor cells with unlimited proliferative capacity. On the contrary, most of benign tumors and normal tissues can't produce enough telomerase so that their proliferative capacity is limited. Since expression of telomerase is feature of tumors cells, telomerase has been considered as an important target in cancer diagnosis and therapeutics. Reacting with different sections in telomerase structure such as hTR formed by RNA, main catalytic subunit of telomerase hTERT, various telomerase inhibitors are studied to find out compounds that suppress unlimited proliferative activity of tumor cells given by telomerase.

Researches show that under normal physical situations and in the presence of K+·Na+, a single strand on the end of chromosomes that is rich in guanine is capable of forming G-quadruplex structure. The G-quadruplex structure consists of a small TTA loops formed bh TTA segments and a guanine-tetrad formed by a square co-planar bonding of four guanine bases connected by hydrogen bondings. Once the interaction between the G-quadruplex with RNA (AATCCC) (SEQ ID NO: 4) of telomerase is inhibited for stabilizing G-quadruplex structure, the telomerase is unable to extend telomeres (add bases). Thus compounds that facilitate or stabilize formation of G-quadruplex structure in human telomeres may have potential in cancer treatment. In previous studies based on stabilization of G-quadruplex structure to develop compounds for suppression of telomere activity, the compounds are divided into two categories-tricyclic G-tetrad ligands and multi-cyclic G-tetrad ligands. 2,6-diamidoanthraquinone is a first tricyclic compound that was found to stabilize the G-quadruplex structure. This is due to delocalized skeletal structure of anthraquinone containing amido group that potentially enhances $\pi$-$\pi$ stacking interactions with DNA bases. Thus nitrogen atoms on side chains interacts with guanine and the 2,6-diamidoanthraquinone plays an important role in the binding of deoxyribonucleotides. The tertiary nitrogen and the quaternary nitrogen are preferred because that an ionic interaction is generated between positive charges and bases. The anticancer activity of anthraquinone compounds depends on various functional groups on its two side chains. The functional groups on the end can bind to the minor grooves of DNA while the grooves beside a plane of the quadruplex structure are minor grooves. Thus different functional groups have great effects on binding capacity and sequence selectivity of the anthraquinone-DNA interaction.

Neidle and his co-workers compared a series of tricyclic Fluoreone derivatives with anthraquinone derivatives. Although the Fluoreone has lower cytotoxicity while on the G-Quadruplex stabilization, it's not as good as anthraquinone derivatives. That means the carbonyl groups on 9, 10-positions have positive effects on its stabilizing ability of G-quadruplex structure. Later, Neidle et al. synthesis a series of 3,6-bisamideacridines derivatives and expect that a nitrogen atom on the center of the chromophore can carry positive charge to stabilize the whole structure. Next 3,6,9-trisubstituted acridines such as BR-ACO-19 are developed and is shown to good abilities to stabilize the G-quadruplex structure. As to TMPyP4, PIPER, RHPS4 and a natural product-Telomestatine, they are all multi-cyclic molecules that stabilize G-quadruplex structure. These multi-cyclic compounds are easily intercalated in and overlapped with the G-quadruplex structure by their planar structure. Moreover, they all include nitrogen atoms with positive charge that enhances interactions between guanines and ions. Therefore, while developing and designing compounds that stabilize the G-quadruplex structure, the following factors should be considered: (a) a planar structure that favors intercalation of molecules within the G-quadruplex structure should be maintained. (b) it's optimal that the nitrogen atoms include positive charges around and the effect of the number of the charge on the interaction is 4+>3+>2+. (c) The compound activity may be affected by introduction hydrogen bonding and the length of side chains. (d) Addition of some certain functional groups into the compounds can enhance the interaction between the compounds and the G-quadruplex structure.

In 1925, Anthraquinone derivatives are used broadly on industries as dyes. A plurality of materials extracted from plants such as emodin, aloe-emodin include anthraquinone as bases and have tumor suppression effects. Furthermore, due to good anticancer effects of anthraquinone structure, the anthraquinone derivatives are synthesized and studied. For example, doxorubincin is a anticancer drug. Doxorubicin is well-known as a highly promising anticancer drug and is applied to a plurality of tumors such as leukemia with good therapeutic effects. It is supposed that anticancer mechanisms of Doxorubicin include intercalation into DNA, change of deoxyribonucleotide structure or function such as suppression of deoxyribonucleotide synthesis and formation of cleavable complex of DNA-topoisomerase II. Through formation of cleavable complex of DNA-topoisomerase II, the topoisomerase II activity is inhibited and free radicals that cause DNA cleavage are free radicals generated. These effects result in cell apoptosis. Yet doxorubincin has serious cardiac toxicity so that its clinical applications are restricted. As to mitoxantrone and ametantrone, they are clinically used anthraquinone derivatives with lower cardiac toxicity than doxorubicin. They are doxorubicin analogues developed in 1970s and their anticancer mechanism is supposed to be the same with doxorubicin-suppression of topoisomerase II activity. In clinical used, the two drugs are applied to leukemia, prostate cancer and multiple sclerosis treatment.

It is mentioned in previous papers that Amidoanthraquinone derivatives have anticancer effect in tumor cell test. In the beginning, Amidoanthraquinone is modified in 1,4-positions. Refer to the paper of Neidle in *J. Med. Chem.*, 1988, compounds formed by substitution on a side chain of 1,4-diaminoanthraquinone can inhibit cancer cell line L1210. Anticancer drug-mitoxantrone used clinically is also a derivative of 1,4-diaminoanthraquinone. Thus the inventor starts from compounds substituted in 1,4-positions or other positions on side chains. In 2004, a series of 1,4-diaminoanthraquinone derivatives is revealed. In the study, methods of synthesizing 1,4-diamindoanthraquinone derivatives are disclosed. One of the ways is to dissolve 1,4-diaminoanthraquinone in N,N-diethylacetamide, then being connected with the substituents containing chloride by acylation (compound $I_{2-4}$). The product is dissolved in ethanol and is added with substituents with amines, the compounds $I_{5-9}$ are obtained through reflux of the solution. Another way is to dissolve 1,4-diaminoanthraquinone in N,N-diethylacetamide, various compounds $I_{10-38}$ are obtained by various substituents connected after acylation (as shown FIG. 1).

In the paper, the mechanism of drug action of 1,4-diaminoanthraquinone derivatives is by binding to and stabilization of the G-quadruplex structure for further inhibition of telomerase. Then three cancer cell lines-C6 Cell (rat glioma cell), Hep G2 (human hepatocellular carcinoma cell line HepG2), 2.2.15 (HBV-producing human hepatoblastoma cell line) are used to evaluate cytotoxic effects of compounds $I_{2-38}$ against cancer cell lines. Results of pharmacological tests show that compounds $I_{5-7}$, $I_9$, $I_{28}$ and $I_{31}$ have good cytotoxicity in C6 cell line, especially $I_9$ and $I_{28}$, twice as effective asadriamycin (IC50), yet still not as good as mitoxantrone. The structure formulas of compounds $I_{5-7}$, $I_9$, $I_{28}$ and $I_{31}$ are shown in FIG. 2. As to in vitro cytotoxic tests on Hep G2 cells, compounds $I_5$, $I_6$, $I_9$ and $I_{11}$ (as shown in FIG. 3) have higher cytotoxic effects. The effect of $I_{11}$ is a bit higher than adriamycin while all four compounds are with higher activity than mitoxantrone. In cytotoxic tests of 2.2.15 cell line, compounds $I_5$, $I_6$ and $I_{11}$ are most active and $I_6$ has higher effect than adriamycin but not better than mitoxantrone. To sum up, compounds $I_5$ and $I_6$ have better cytotoxic effects on these tumor cell lines.

Due to tumor cell suppression of substituents at 1,4-position, the inventors further work on synthesis of 1,5-diaminoanthraquinone derivatives with different substituents at 1,5-positions. In 2006, a series of 1,5-diaminoanthraquinone derivatives is revealed. In the paper, methods of synthesizing 1,5-diamido-isomers are disclosed. One of the ways is to dissolve 1,5-diaminoanthraquinone in DMF and reflux heated, the being connected with the substituents containing chloride by acylation (compound $II_{2-4}$). The product is dissolved in DMSO and is added with substituents with amines, the compounds $II_{5-10}$ are obtained through reflux of the solution. Another way is to dissolve 1,5-diaminoanthraquinone in DMF, reflux heated, and connected with the substituents containing chloride by acylation. Then the product got is dissolved in DMSO, added with substituents with amines and reflux heated to get compounds $II_{12-18}$. Or dissolve 1,5-diaminoanthraquinone in DMF and reflux heated, acylated to connect with substituents to obtain various compounds $II_{19-27}$ (as shown FIG. 4).

As to mechanisms of drug action, it is mentioned above that 1,4-diaminoanthraquinone derivatives can bind to and stabilize the G-quadruplex structure so as to inhibit telomerase. No 1,5-diamido-isomers is found not only inhibit telomerase by above mechanim, another way to intercalate into DNA and inhibit topoisomerase II. Moreover, free radicals generated cause damage of DNA directly. In pharmacological tests, three cancer cell lines-C6 Cell (rat glioma cell), Hep G2 (human hepatocellular carcinoma cell line HepG2), 2.2.15 (HBV-producing human hepatoblastoma cell line) are used to determine cytotoxic effects of compounds $II_{2-27}$ against cancer cell lines. Results of pharmacological tests show that compounds $II_5$, $II_{16}$ and $II_{18}$ have better cytotoxic effect, compared to mitoxantrone. In cytotoxic tests on G2 Cells, the cytotoxic effect of compounds $II_5$ and $II_{18}$ on tumor cells are not bad, especially compound $II_{18}$ is with higher cytotoxic effect on HBV-producing human hepatoblastoma than mitoxantrone. The chemical structures of mitoxantrone and compounds $II_5$, $II_{16}$ and $II_{18}$ are shown in FIG. 5.

Next another series of compounds 2,6-diaminoanthraquinone derivatives are synthesized and compared with 1,4-diamido-isomers, 1,5-diamino-isomers, 1,5-diamido-isomers, 1,5-diacyloxy-isomers and 1,5-dithio-isomers to review their anti-tumor effects. A series of papers is published in 2007. In the papers, methods to synthesize 2,6-diamido-isomers is disclosed. One of the methods is to dissolve 2,6-diaminoanthraquinone in DMF and being connected with the substituents containing chloride by acylation (compound $III_{31-32}$, $III_{39}$).

Then the product got is dissolved in DMF, added with substituents with amines, the compounds $III_{33-38}$ are obtained through reflux heated.

Another way is to dissolve 2,6-diaminoanthraquinone in DMF, being acylated to connect with various substituents for obtaining compounds $III_{45-47}$ (as shown in FIG. 6).

As to pharmacological activity comparison between 1,5-diamido-isomers and 2,6-diamido-isomers, hTERT-BJ1 (human normal skin fibroblast cells) and H1299 (non-small cell lung cancer cells) cell lines are used.

The pharmacological tests used include TRAP assay that measures whether the compounds can stabilize telomeric G-quadruplex structure and SEAP assay that is used as the reporter system to evaluate activation and suppression of telomerase(PhTERT). The results of the TRAP assay show that compounds $II_5$, $II_{17}$, $III_{33}$ and $III_{34}$ (as shown in FIG. 7) can stabilize G-quadruplex and further suppress tolomerase activity with good effects. Moreover, it is noted that most of derivatives of 1,5-diacyloxy-isomers and 1,5-dithio-isomers has no effects of telomerase inhibition. As to previous synthesized 1,4-diamino、1,5-diamino、1,5-diamido、2,6-diamido-isomers, once they are connected with substitutes like side chain substitution pattern of mitoxantrone, the compounds have stronger inhibition activity. In the SEAP assay, it is found that 1,5-diacyloxy-isomers、1,5-dithio-isomers、1,4-diamido-isomers can activate hTERT-BJ1 cells yet 1,5-diamido-isomers derivatives and 2,6-diamido-isomers derivatives have no effects on hTERT-BJ1 cells or H1299 cells.

Until now, anthraquinone derivatives with substituents at various positions have been synthesized. The derivatives substituted at positions of 1,4, 1,5, 2,6, or 2,7 are all found with telomerase inhibition activity in pharmacological tests, especially derivatives with amido substituents in the side chain, the inhibition of telomerase activity is obvious.

In order to overcome shortcomings of traditional anticancer drug-doxorubicin and base on synthesis anthraquinone derivatives with substituents at different positions for tumor inhibitions, there is a need to provide anti-cancer compounds and manufacturing methods thereof. The anticancer compounds are a series of 1,8-diamidoanthraquinone derivatives with amino compounds having a novel chemical structure yet without side effects such as serious cardiac toxicity of traditional anticancer drugs-doxorubicin.

SUMMARY OF THE INVENTION

Therefore it is a primary object of the present invention to provide anti-cancer compounds and manufacturing methods thereof. The anticancer compounds are a series of 1,8-diamidoanthraquinone derivatives with amino compounds having a novel chemical structure.

It is another object of the present invention to provide anti-cancer compounds and manufacturing methods thereof that overcome shortcomings of serious cardiac toxicity of conventional anticancer drug-doxorubicin.

The anti-cancer compounds of the present invention include:

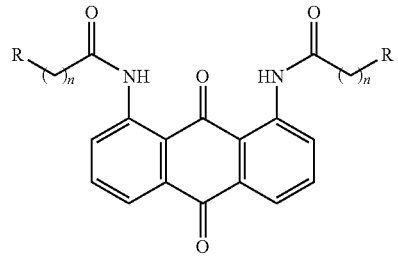

wherein n=1, R is one of the followings:
$NHCH_2CO_2CH_3$, $NHCH(CH_2CH_2SCH_3)CO_2CH_3$, $N(CH_2CH_2CH_2CH_2)CO_2CH_3$, $NHCH(CH(CH_3)_2)CO_2CH_3$, (D)-$NHCH(CH(CH_3)_2)CO_2CH_3$, $N(CH_3)CH_2CO_2CH_3$, $NHCH(CH_2CH(CH_3)_2)CO_2CH_3$, $NHCH(CH_3)CO_2CH_3$, (D)-$NHCH(CH_3)CO_2CH_3$, $NHCH(C_6H_5)CO_2CH_3$, $NHCH_2CH(CH_3)_2$, $N(CH_2CH_3)_2$, $N(CH_3)_2$, $N(CH_2CH_2CH_3)_2$, $NHCH(CH_3)_2$, $NHCH_2CH_3$, 3-$(CF_3)C_6H_4$—$CH_2NH$, $N(CH_3)CH_2CH_3$, $N(CH_3)CH_2CH_2CH_3$ 及$NHCH(CH_2OCH(CH_3)_3)CO_2CH_3$, wherein n=2 and R is one of the followings: $N(CH_2CH_3)_2$, $NHCH_2CH(CH_3)_2$, 3,5-$F_2C_6H_3CH_2NH$, $NHCH_2CH_2NHCO_2C(CH_3)_3$, $NHCH_2CH_2N(CH_3)_2$, $N(CH_3)_2$, $N(CH_2CH_2CH_3)_2$, $NHCH_3$, $NHCH(CH_3)_2$, $NHCH_2CH_2CH_2N(CH_3)_2$ A manufacturing method of the anti-cancer compound consists of following steps:

1,8-bis(chloroacetamido)anthraquinone or 1,8-bis(3-chloropropionamido)anthraquinone is added with an amino compound, a catalyst, and dehydrated dimethylformamide (DMF) to form a mixture and react with one another.

Then by purification and recrystallization, the anti-cancer compound is obtained.

BRIEF DESCRIPTION OF THE DRAWINGS

The structure and the technical means adopted by the present invention to achieve the above and other objects can be best understood by referring to the following detailed description of the preferred embodiments and the accompanying drawings, wherein

FIG. 8 shows chemical structure of anti-cancer compounds according to the present invention;

FIG. 14 shows chemical structure of telomerase inhibitor BR-ACO-19 and dibenzo[b,j] (1,7)phenathroline.

DETAILED DESCRIPTION OF THE PREFERRED EMBODIMENT

Figure 1:
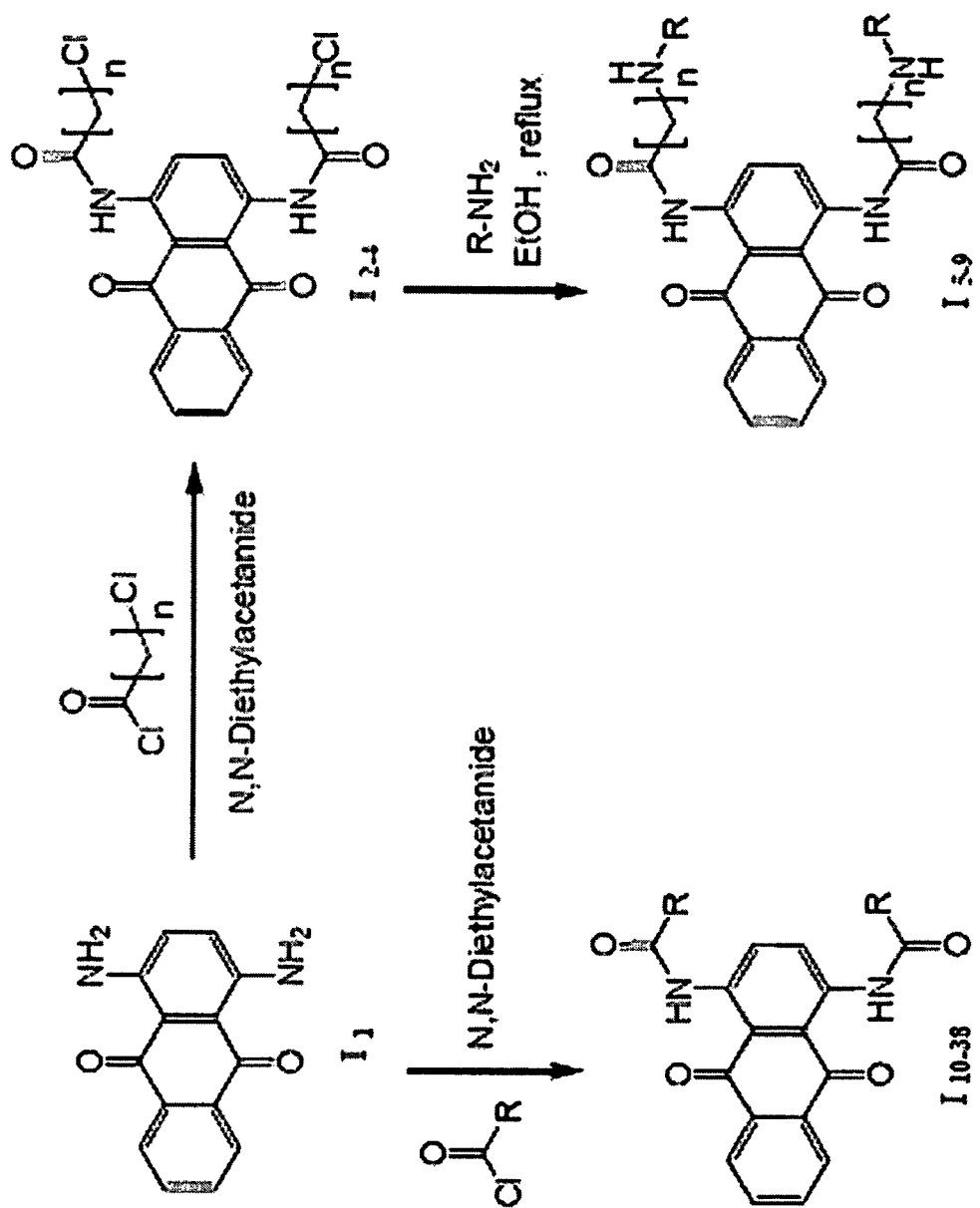
FIG. 1 shows synthesis of conventional compounds $I_{2-4}$, $I_{5-9}$ and $I_{10-38}$.
Figure 2:
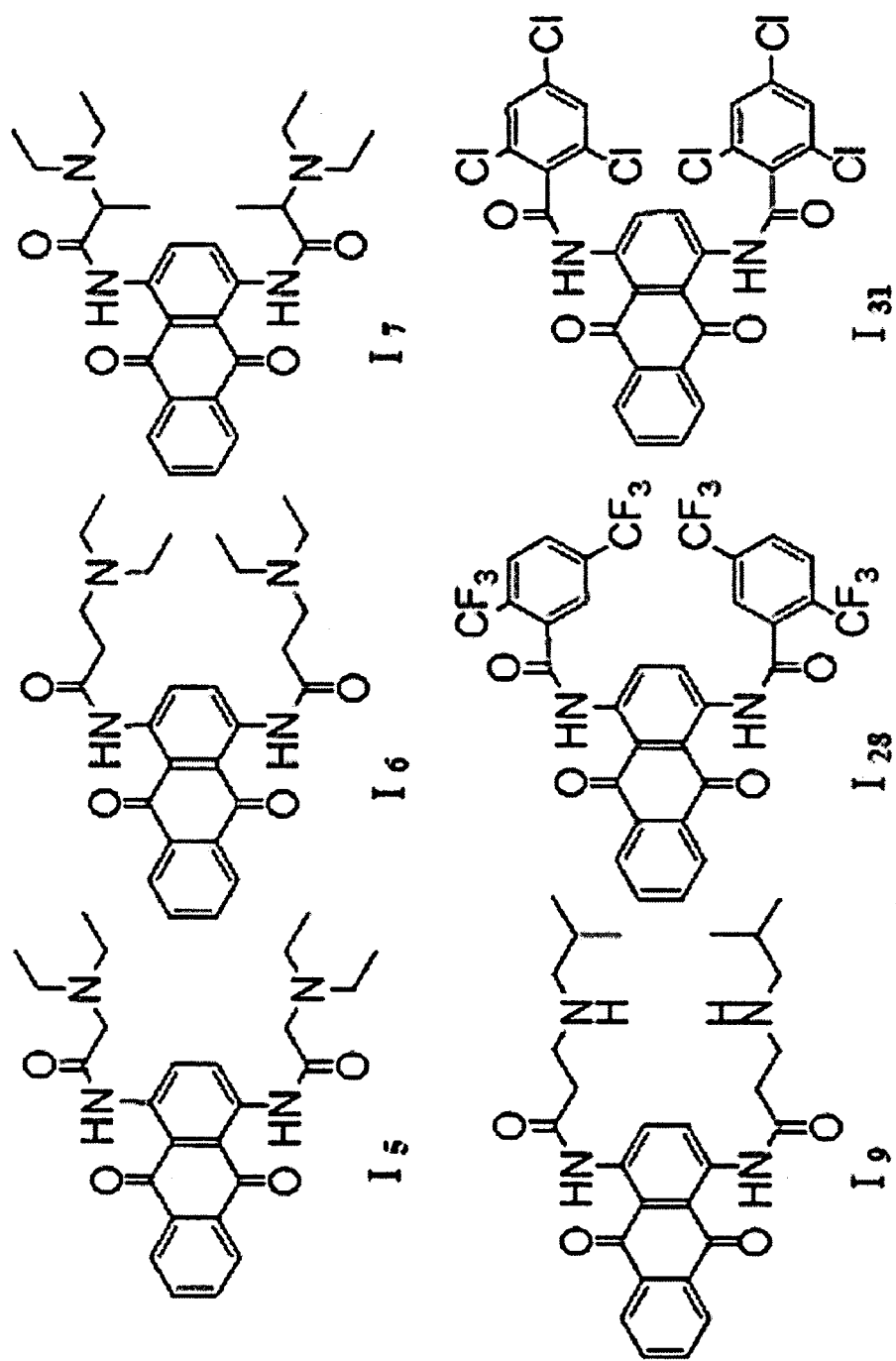
FIG. 2 shows chemical structure of conventional compounds $I_{5-7}$, $I_9$, $I_{28}$ and $I_{31}$.
Figure 3:
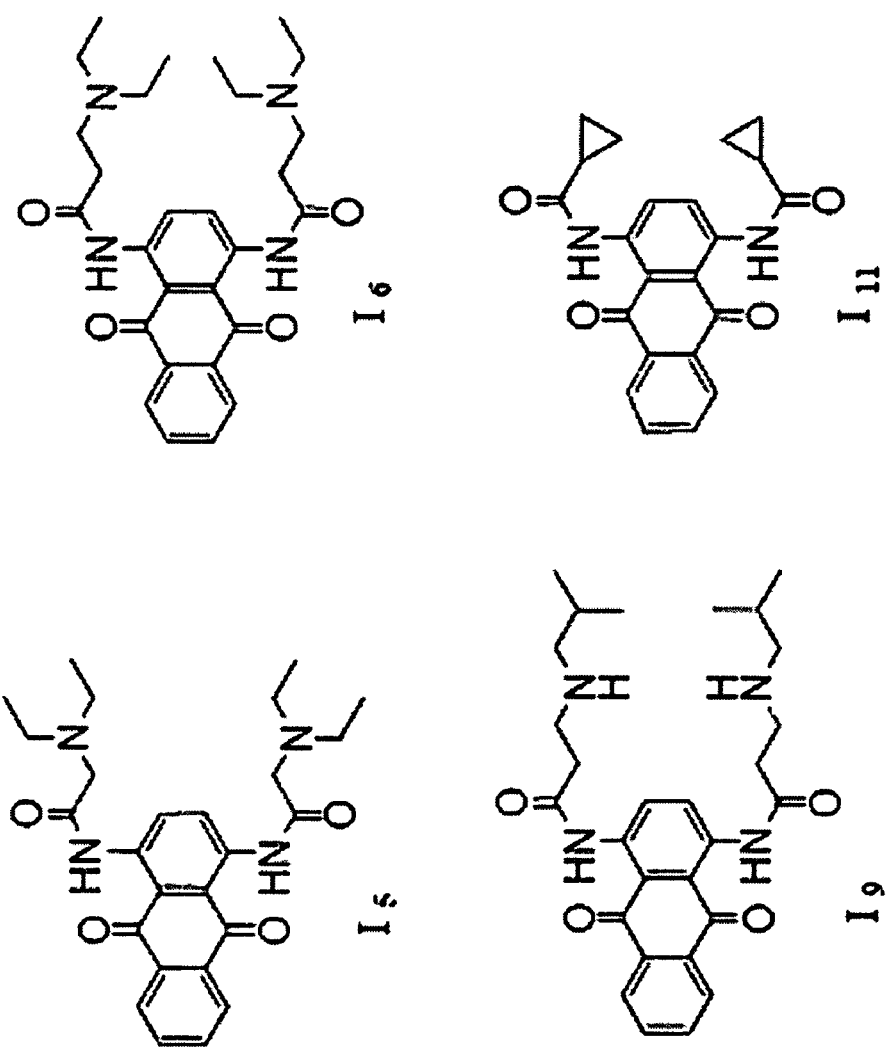
FIG. 3 shows chemical structure of conventional compounds $I_5$, $I_6$, $I_9$ and $I_{31}$.
Figure 4:
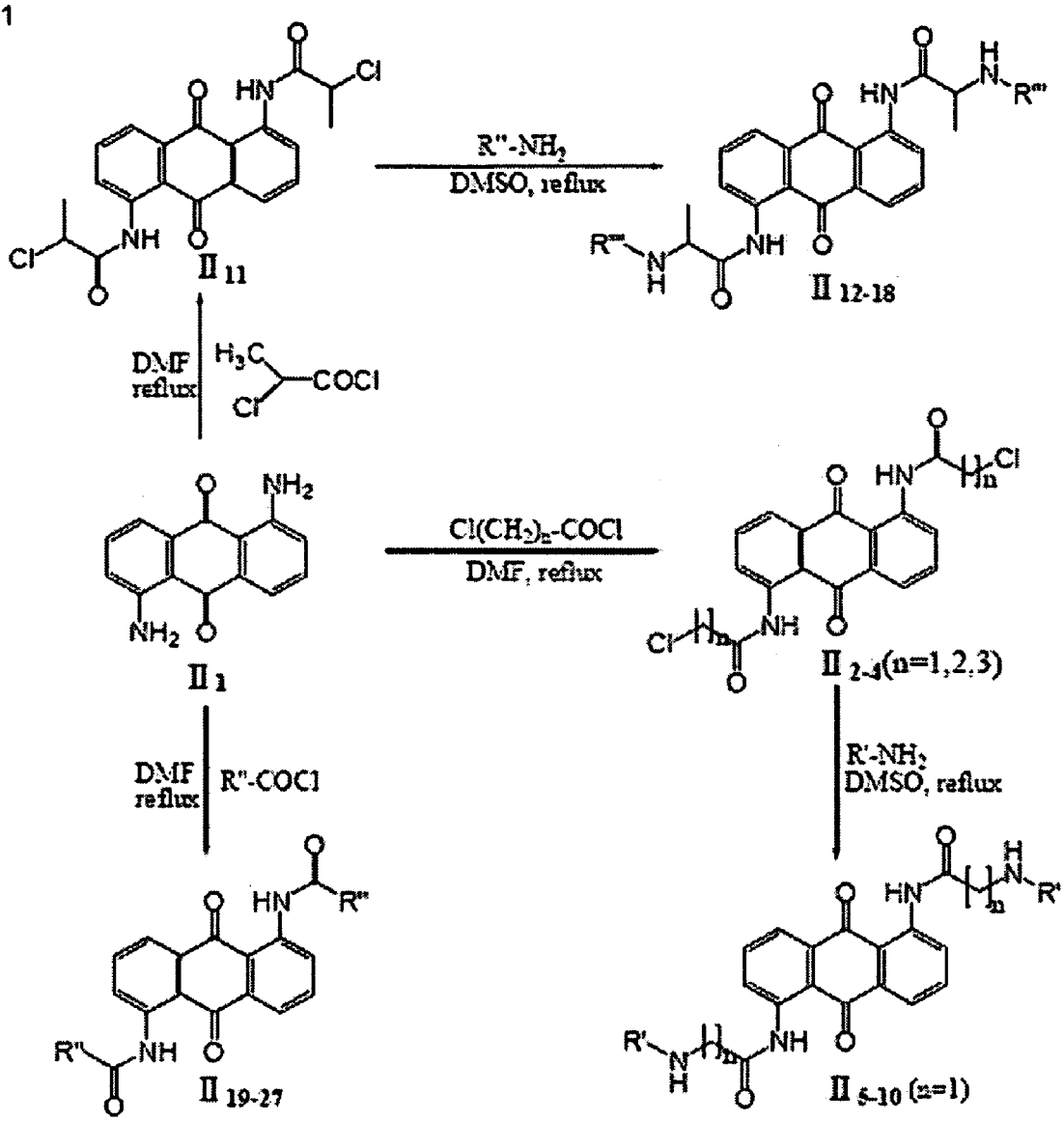
FIG. 4 shows synthesis of conventional compounds $II_{2-4}$, $II_{5-10}$, $II_{12-18}$ and $II_{19-27}$.
Figure 5:
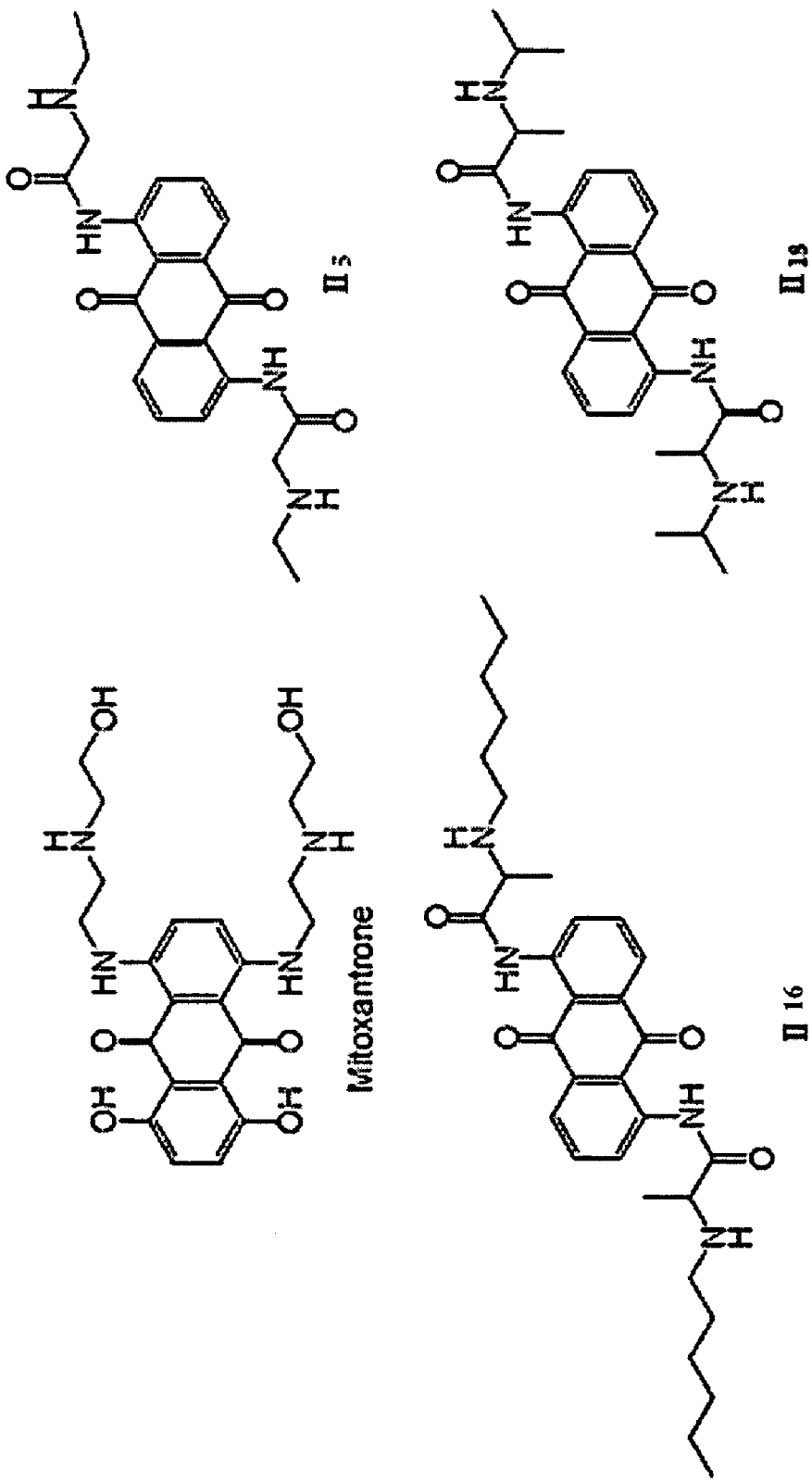
FIG. 5 shows chemical structure of compounds mitoxantrone, $II_5$, $II_{16}$ and $II_{18}$.
Figure 6:
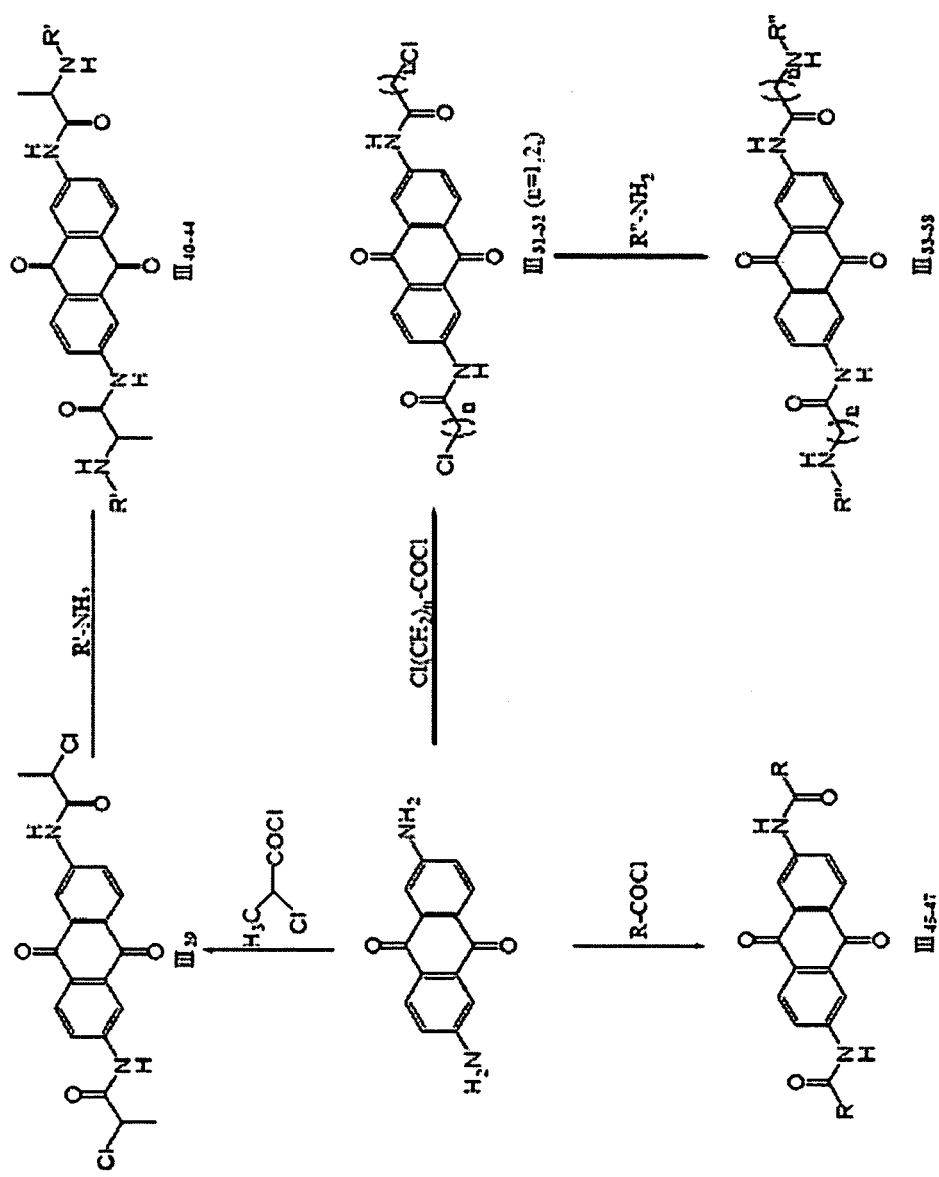
FIG. 6 shows synthesis of conventional compounds $III_{31-32}$, $III_{33-38}$, $III_{40-44}$ and $III_{45-47}$.
Figure 7:
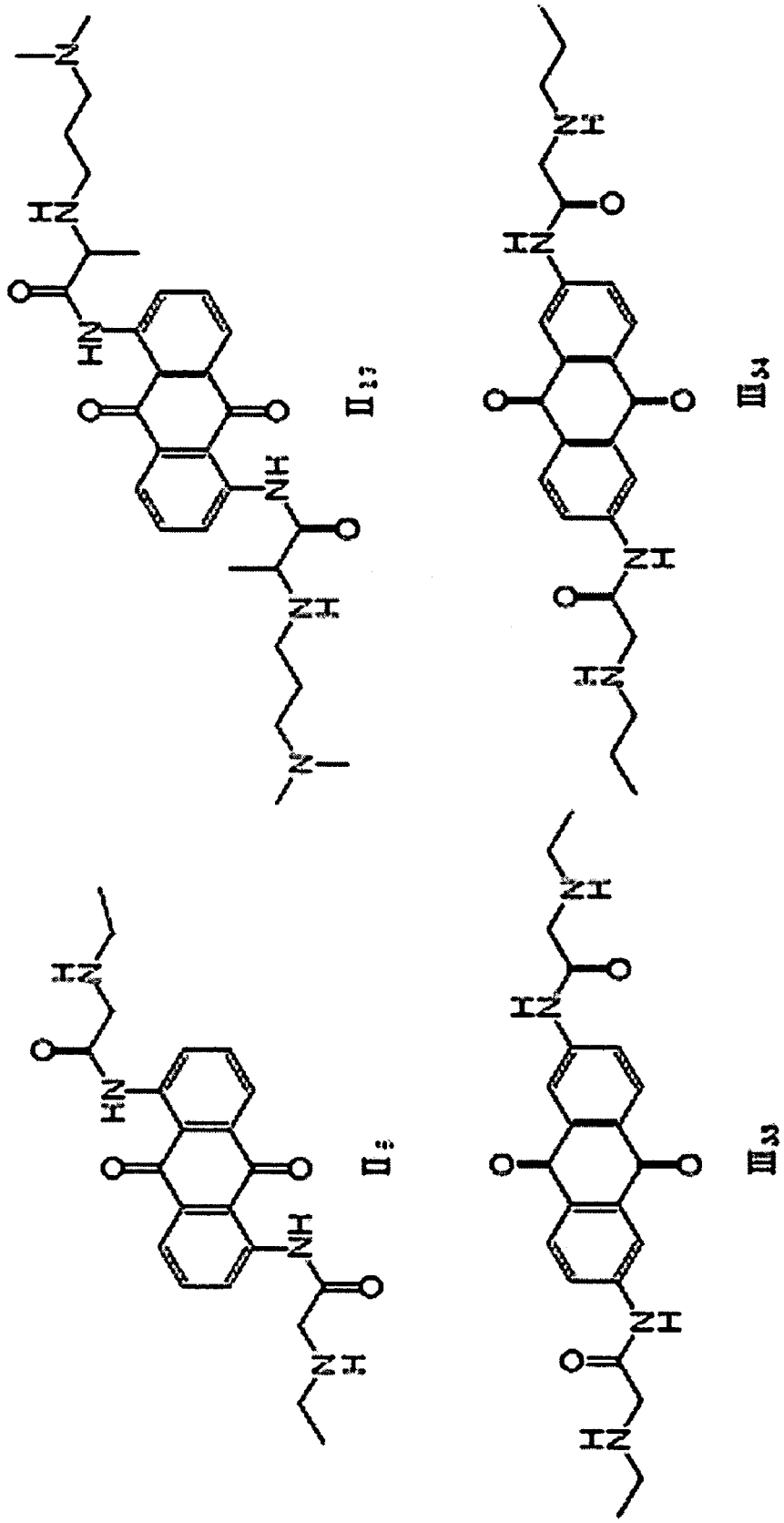
FIG. 7 shows chemical structure of compounds $II_5$, $II_{17}$, $III_{33}$ and $III_{34}$.
Figure 9:
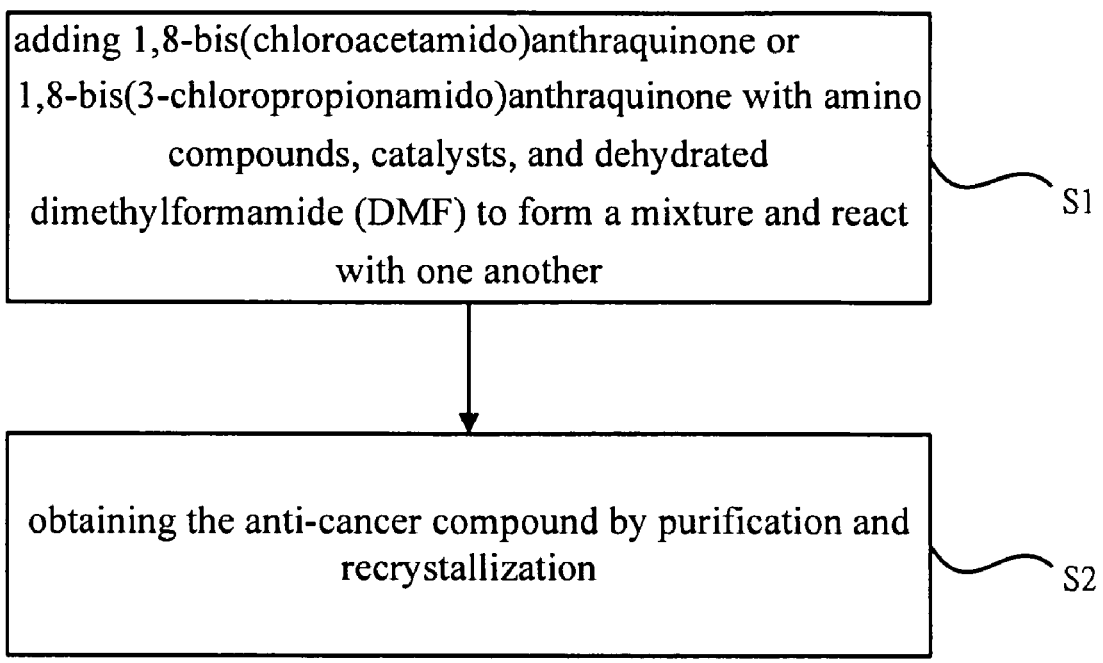
FIG. 9 is a flow chart showing manufacturing steps of the anti-cancer compounds according to the present invention.

Refer to FIG. 8, an anti-cancer compound of the present invention include:

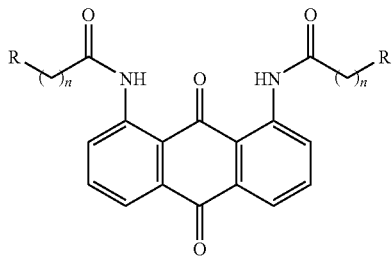

wherein once n=1 and R is $NHCH_2CO_2CH_3$
$NHCH(CH_2CH_2SCH_3)CO_2CH_3$, $N(CH_2CH_2CH_2CH_2)CO_2CH_3$, $NHCH(CH(CH_3)_2)CO_2CH_3$, (D)-$NHCH(CH(CH_3)_2)CO_2CH_3$, $N(CH_3)CH_2CO_2CH_3$, $NHCH(CH_2CH(CH_3)_2)CO_2CH_3$, $NHCH(CH_3)CO_2CH_3$, (D)-$NHCH(CH_3)CO_2CH_3$, $NHCH(C_6H_5)CO_2CH_3$, $NHCH_2CH(CH_3)_2$, $N(CH_2CH_3)_2$, $N(CH_3)_2$, $N(CH_2CH_2CH_3)_2$, $NHCH(CH_3)_2$, $NHCH_2CH_3$, $3-(CF_3)C_6H_4CH_2NH$, $N(CH_3)CH_2CH_3$, $N(CH_3)CH_2CH_2CH_3$ 及NHCH $(CH_2OCH(CH_3)_3)CO_2CH_3$ . . .

wherein once n=2 and R is $N(CH_2CH_3)_2$, $NHCH_2CH(CH_3)_2$, $3,5-F_2C_6H_3CH_2NH$,
$NHCH_2CH_2NHCO_2C(CH_3)$, $NHCH_2CH_2N(CH_3)_2$, $N(CH_3)_2$, $N(CH_2CH_2CH_3)_2$, $NHCH_3$, $NHCH(CH_3)_2$, $NHCH_2CH_2CH_2N(CH_3)_2$ 及$_{N(CH3)}CH_2CH_3$ A manufacturing method of the anti-cancer compound according to the present invention consists of the following steps, as shown in FIG. 9:

S1: 1,8-bis(chloroacetamido)anthraquinone or 1,8-bis(3-chloropropionamido)anthraquinone is added with amino compounds, catalysts, and dehydrated dimethylformamide (DMF) to form a mixture and react with one another; and S2: By purification and recrystallization, the anti-cancer compound is obtained.

In the step S1, amino compounds is selected from one of the followings: glycine methyl ester hydrochloride, methionine methyl ester hydrochloride, proline methyl ester hydrochloride, (L)-valine methyl ester hydrochloride, (D)-valine methyl ester hydrochloride, sacrocine methyl ester hydrochloride, leucine methyl ester hydrochloride, (L)-alaline methyl ester hydrochloride, (D)-alaline methyl ester hydrochloride, (S)-phenylglycine methyl ester hydrochloride, isobutylamine, diethylamine, dimethylamine, dipropylamine, isopropylamine, ethanamine, 3-(trifluoromethyl) benzylamine, N-ethylmethylamine, N-methylpropylamine, O-tert-butyl-serine methyl ester hydrochloride, 3,5-difluorobenzylamine, N-Boc-ethanediamine, N,N-dimethylethanediamine, methylamine and N,N-dimethylpropane-1,3-diamine.

In the step S1, the catalysts is selected from N,N-Diisopropylethylamine (DIPEA), pyridine, and triethylamine (TEA). The step S1 further includes a step of reacting in a sealed container and a step of reacting of the mixture in an oil bath and then pouring the mixture into ice-water. The reaction temperature of the oil bath ranges from 70° C. to 150° C. and the reaction time is from 0.5 to 6 hours.

In the step S2, the purification includes filtration, vacuum pressure reduction concentration or extraction. The extraction is run with ethyl acetate. The step S2 further having a step of recrystallization from ethanol.

In the step S1, a manufacturing method of 1,8-bis(chloroacetamido)anthraquinone includes the steps of: add 1,8-dinitroanthraquinone with ethanol, and then add sodium sulfide nonahydrate and sodium hydroxide solution into the mixture to be mixed and reflux heated. After standing and filtration, 1,8-diaminoanthraquinone is obtained by recrystallization of the solution. Next the 1,8-diaminoanthraquinone is dissolved in N,N-dimethylform amide, and pyridine is added for catalyzing, and then chloroacetyl chloride is added into and mixed with the mixture to react. Pour the solution into ice water, 1,8-bis(chloroacetamido) anthraquinone is obtained after filtration and recrystallization of the solution. The step of adding pyridine for catalyzing is run under an ice-bath while in the step of adding and mixing chloroacetyl chloride into the mixture, the ice bath is removed, the nitrogen gas is introduce and the step is run under light protection condition. The step of adding and mixing chloroacetyl chloride into the mixture is run at the room temperature for 24 hours.

In the step S1, a manufacturing method of 1,8-bis(3-chloropropionamido)anthraquinone includes the steps of: dissolve 1,8-diaminoanthraquinone in N,N-dimethylformamide, add pyridine for catalyzing, and then 3-chloropropioyl chloride is added into and mixed with the mixture to react. Pour the solution into ice water, 1,8-bis(3-chloropropionamido)anthraquinone is obtained after filtration and recrystallization of the solution.

The step of adding pyridine for catalyzing is taken in an ice-bath while in the step of adding and mixing 3-chloropropioyl chloride into the mixture, the ice bath is removed, the nitrogen gas is introduced and the step is run under light protection condition. The step of adding and mixing 3-chloropropioyl chloride into the solution is run at the room temperature for 24 hours.

EMBODIMENT 1,8-diaminoanthraquinone (2)

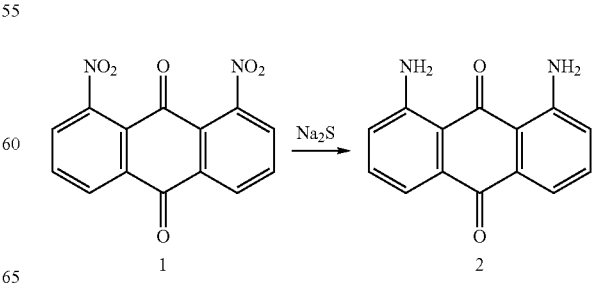

Add 1,8-dinitroanthraquinone (1.49 g, 5 mmol) into 56 ml ethanol and stir the mixture. Then add a reductive solution containing sodium sulfide nonahydrate (5.4 g, 22.5 mmol), sodium hydroxide (2.14 g, 53.5 mmol) dissolved in 95 ml water. The mixed solution is reflux heated for 6 hours, standing overnight, and filter the precipitate. The precipitate is recrystallized from ethanol to get red compound 2.

Mol. Wt.: 238.0742 ($C_{14}H_{10}N_2O_2$)

Yield: 73%

Mp: 272-273° C. (EtOH)

HRMS (EI) m/z calcd for $C_{14}H_{10}N_2O_2$ $^+[M+H]^+$: 238.0742. Found: 238.0742.

$^1$H-NMR (300 MHz, $CDCl_3$) δ (ppm):

7.15 (dd, J=8.1 Hz, 1.2 Hz, 2H, Ar—$H_{2,7}$), 7.34 (dd, J=7.5 Hz, 1.2 Hz, 2 H, Ar—$H_{4,5}$), 7.44 (t, J=7.2 Hz, 2H, Ar—$H_{3,6}$), 12.86 (b, 7.84, 2 H, Ar—NH—)

1,8-Bis(chloroacetamido)anthraquinone (3)

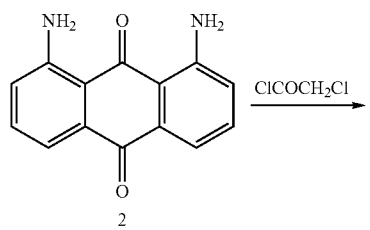

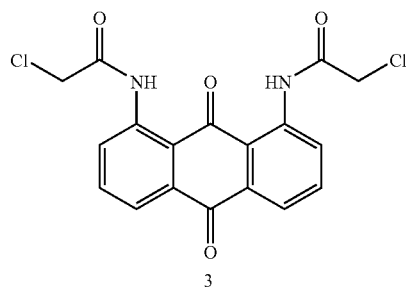

Dissolve 1,8-diaminoanthraquinone (0.476 g, 2.0 mmol) in 20 ml DMF. Add pyridine (0.5 ml) as catalyst in an ice bath. Then add chloroacetyl chloride (0.5 ml, 6 mmol) into the solution, remove the ice bath, introduce nitrogen, protect from light, and stir the solution at room temperature for 24 hours. The reacted solution is poured into ice water (50 ml), filtered to get precipitate. At last, the precipitate is recrystallized to get yellow compound 3.

Mol. Wt.: 390.0174 ($C_{18}H_{12}C_2N_2O_4$)

Yield: 80%

Mp: 280-281° C. (EtOH)

HRMS (EI) m/z calcd for $C_{18}H_{12}C_2N_2O_4$ $^+[M+H]^+$: 390.0174. Found: 390.0174.

$^1$H-NMR (300 MHz, $CDCl_3$) δ (ppm) 4.30 (s, 8H, —$CH_2$—), 7.83 (t, J=7.8 Hz, 2H, Ar—$H_{3,6}$), 8.13 (d, J=7.2 Hz, 2H, Ar—$H_{4,5}$), 9.17 (d, J=8.1 Hz, 2H, Ar—$H_{2,7}$), 13.02 (s, 2H, Ar—NH—)

1,8-Bis[2-(glycin methyl ester)acetamido]anthraquinone (3a)

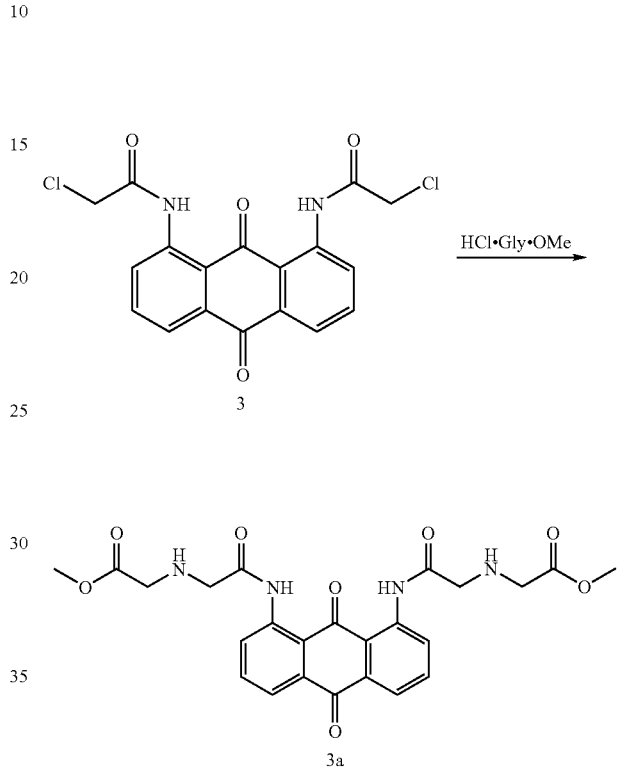

Add glycine methyl ester hydrochloride (0.75 g, 6 mmole) into DIPEA (2 ml, 12 mmole) and 20 ml dehydrated dimethylformamide (DMF), stir the solution for 10 minutes. Then add compound 3 (0.3 g, 0.75 mmol) into the mixture and react in a sealed device-mini-reactor. The reaction temperature is 130-150° C. in the oil bath and the reaction time is 90 minutes. The reacted solution is poured into 50 ml ice water, extracted with ethyl acetate, vacuum pressure reduction concentrated, and recrystallized from ethanol to get brown yellow compound 3a.

Mol. Wt.: 496.1594 ($C_{24}H_{24}N_4O_8$)

Yield: 42%

Mp: 173-174° C. (EtOH)

IR (KBr) cm-1: 3187 (NH), 2938 (NH), 1732 (CO), 1693 (CO)

HRMS (EI) m/z calcd for $C_{24}H_{24}N_4O_8$ $^+[M+H]^+$: 496.1594. Found: 496.1596.

$^1$H-NMR (300 MHz, $CDCl_3$) δ (ppm):

3.60 (s, 8H, —$CH_2$—), 3.75 (s, 6H, —$OCH_3$—), 7.75 (t, J=8.1 Hz, 2H, Ar—$H_{3,6}$), 8.02 (d, J=7.8 Hz, 2H, Ar—$H_{4,5}$), 9.18 (d, J=8.7 Hz, 2H, Ar—$H_{2,7}$), 12.86 (s, 2H, Ar—NH—)

$^{13}$C-NMR (300 MHz, $CDCl_3$) δ (ppm):

50.07, 51.23, 53.13, 118.60 ($C_{8a,9a}$), 121.91 ($C_{2,7}$), 126.18 ($C_{4,5}$), 132.87 ($C_{3,6}$), 134.92 ($C_{4a,5a}$), 140.63 ($C_{1,8}$), 171.07 (NCO), 172.02 (CCO), 181.93 ($C_{10}$O), 189.77 ($C_9$O)

1,8-Bis[2-(methioine methyl ester)acetamido]anthraquinone (3b)

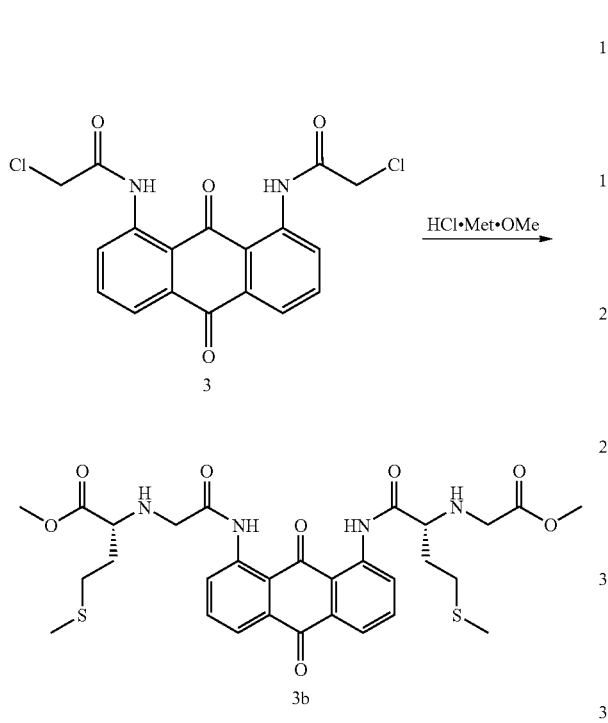

Add methionine methyl ester hydrochloride (1.2 g, 6 mmole) into DIPEA (2 ml, 12 mmole) and 20 ml dehydrated dimethylformamide (DMF) and stir the solution for 10 minutes. Then add compound 3 (0.3 g, 0.75 mmol) into the mixture and react in a sealed device-mini-reactor. The reaction temperature is 130-150° C. in the oil bath and the reaction time is 90 minutes. The reacted solution is poured into 50 ml ice water, extracted with ethyl acetate, vacuum pressure reduction concentrated, and recrystallized from ethanol to get brown yellow compound 3b.

Mol. Wt.: 644.1975 ($C_{30}H_{36}N_4O_8S_2$)

Yield: 40%

Mp: 126-127° C. (EtOH)

IR (KBr) cm-1: 3194 (NH), 2938 (NH), 1738 (CO), 1694 (CO), 1628 (CO)

HRMS (EI) m/z calcd for $C_{30}H_{36}N_4O_8S_2$ $^+$[M+H]$^+$: 644.1975. Found: 644.1976.

$^1$H-NMR (300 MHz, CDCl$_3$) δ (ppm):

1.98 (s, 6H, SCH3), 2.01-2.11 (m, 4H, —CH$_2$), 2.65-2.71 (m, 4H, —CH$_2$—), 3.48 (t, J=6.3 Hz 2H, CH), 3.34 (d, J=17.1 Hz, 2H, —CH—), 3.74 (s, 6 H, —OCH$_3$), 3.76 (d, J=17.1 Hz, 2H, —CH$_2$—), 7.67 (t, J=8.1 Hz, 2H, Ar—H$_{3,6}$), 7.94 (d, J=7.2 Hz, 2H, Ar—H$_{4,5}$), 9.46 (d, J=8.4 Hz, 2H, Ar—H$_{27}$), 12.61 (s, 2H, Ar—NH—)

$^{13}$C-NMR (300 MHz, CDCl$_3$) δ (ppm):

14.58, 29.72, 32.06, 51.46, 52.01, 59.76, 118.39 ($C_{8a,9a}$), 121.97 ($C_{2,7}$), 126.20 ($C_{4,5}$), 132.85 ($C_{3,6}$), 135.02 ($C_{4a,5a}$), 140.80 ($C_{1,8}$), 171.16 (NCO), 174.20 (CCO), 181.90 ($C_{10}$O), 189.85 ($C_9$O)

1,8-Bis[2-(proline methyl ester)acetamido]anthraquinone (3c)

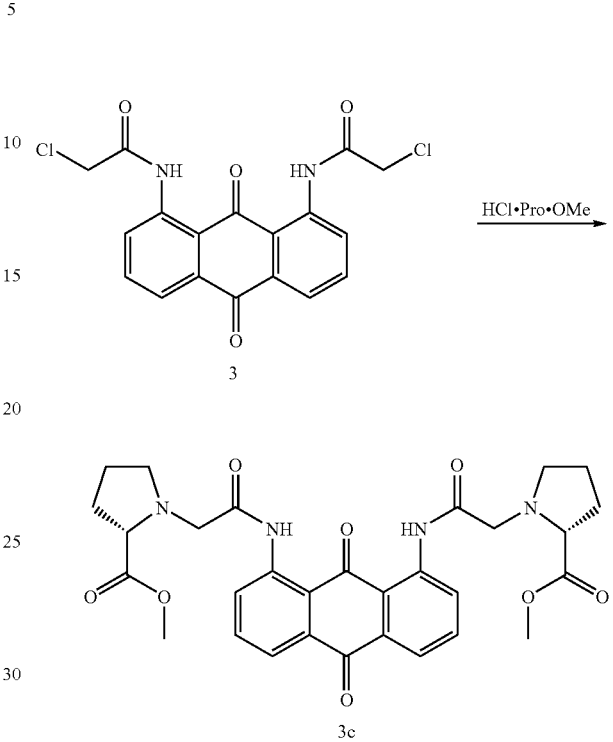

Add 1.2 g, 6 mmole proline methyl ester hydrochloride into DIPEA (2 ml, 12 mmole) and 20 ml dehydrated dimethylformamide (DMF) and stir the solution for 20 minutes. Then add compound 3 (0.3 g, 0.75 mmol) into the mixture and react in a sealed device-mini-reactor. The reaction temperature is 130-150° C. in the oil bath and the reaction time is 90 minutes. The reacted solution is poured into 50 ml ice water, extracted with ethyl acetate, vacuum pressure reduction concentrated, and recrystallized from ethanol to get yellow compound 3c.

Mol. Wt.: 576.2220 ($C_{30}H_{32}N_4O_8$)

Yield: 60%

Mp: 170-171° C. (EtOH)

IR (KBr) cm-1: 3202 (NH), 2952 (NH), 1732 (CO), 1694 (CO), 1627 (CO)

HRMS (EI) m/z calcd for $C_{30}H_{32}N_4O_8$$^+$[M+H]$^+$: 576.2220. Found: 576.2224.

$^1$H-NMR (300 MHz, CDCl$_3$) δ (ppm): 1.92-2.23 (m, 8H, —CH$_2$—), 2.78 (dd, 2H, J=7.5 Hz, 15.3 Hz, —CH—), 3.23-3.67 (m, 4H, NCH$_2$), 3.53 (d, J=16.8 Hz, 2H, —CH—), 3.67 (s, 6H, —OCH$_3$), 3.75 (d, J=16.8 Hz, 2H, —CH$_2$—), 7.62 (t, J=8.1 Hz, 2H, Ar—H$_{3,6}$), 7.86 (d, J=7.5 Hz, 2H, Ar—H$_{4,5}$), 9.06 (d, J=8.7 Hz, 2H, Ar—H$_{27}$), 12.33 (s, 2H, Ar—NH—)

$^{13}$C-NMR (300 MHz, CDCl$_3$) δ (ppm):

23.55, 28.95, 51.03, 53.18, 57.28, 63.96, 118.22 ($C_{8a,9a}$), 121.70 ($C_{2,7}$), 126.07 ($C_{4,5}$), 132.77 ($C_{3,6}$), 134.93 ($C_{4a,5a}$), 141.01 ($C_{1,8}$), 170.34 (NCO), 173.44 (CCO), 181.78 ($C_{10}$O), 189.97 ($C_9$O)

(L)-1,8-Bis[2-(valine methyl ester)acetamido]anthraquinone (3d)

(D)-1,8-Bis[2-(valine methyl ester)acetamido]anthraquinone (3e)

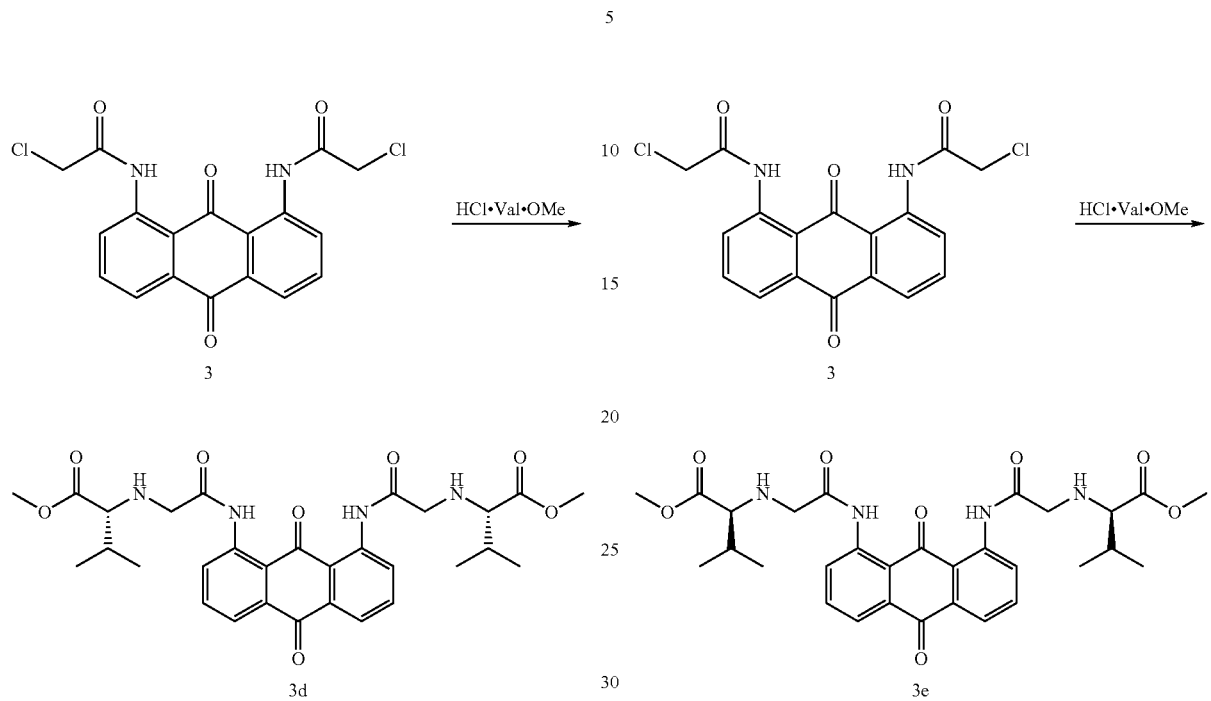

Add 1.0 g, 6 mmole (L)-valine methyl ester hydrochloride into DIPEA (2 ml, 12 mmole) and 20 ml dehydrated dimethylformamide (DMF) and stir the solution for 10 minutes. Then add compound 3 (0.3 g, 0.75 mmol) into the mixture and react in a sealed device-mini-reactor. The reaction temperature is 130-150° C. in the oil bath and the reaction time is 90 minutes. The reacted solution is poured into 50 ml ice water, extracted with ethyl acetate, vacuum pressure reduction concentrated, and recrystallized from ethanol to get yellow compound 3d.

Mol. Wt.: 580.2533 ($C_{30}H_{36}N_4O_8$)

Yield: 47%

Mp: 150-151° C. (EtOH)

IR (KBr) cm-1: 3225 (NH), 2961 (NH), 1736 (CO), 1693 (CO), 1630 (CO)

HRMS (EI) m/z calcd for $C_{30}H_{36}N_4O_8{}^+[M+H]^+$: 580.2533. Found: 580.2532.

1H-NMR (300 MHz, CDCl$_3$) δ (ppm):

0.98 (d, J=6.6 Hz, 6H, —CH$_3$), 1.02 (d, J=6.6 Hz, 6H, —CH$_3$), 2.01-2.08 (m, 2H, —CH$_2$—), 2.27 (s, 2H, NH), 3.09 (d, J=5.4 Hz, 2H, —CH—), 3.28 (d, J=16.8 Hz, 2H, —CH$_2$—), 3.63 (d, J=16.8 Hz, 2H, —CH$_2$—), 3.71 (s, 6 H, —OCH$_3$), 7.63 (t, J=7.8 Hz, 2H, Ar—H$_{3,6}$), 7.90 (d, J=7.2 Hz, 2H, Ar—H$_{4,5}$), 9.07 (d, J=8.4 Hz, 2H, Ar—H$_{2,7}$), 12.44 (s, 2H, Ar—NH—)

13C-NMR (300 MHz, CDCl$_3$) δ (ppm): 18.05, 18.46, 30.94, 51.00, 52.52, 66.90, 118.45 ($C_{8a,9a}$), 121.92 ($C_{2, 7}$), 126.29 ($C_{4, 5}$), 132.87 ($C_{3, 6}$), 134.93 ($C_{4a,5a}$), 140.77 ($C_{1, 8}$), 170.95 (NCO), 174.11 (CCO), 181.83 ($C_{10}O$), 189.69 ($C_9O$)

Add 1.0 g, 6 mmole (D)-valine methyl ester hydrochloride into DIPEA (2 ml, 12 mmole) and 20 ml dehydrated dimethylformamide (DMF) and stir the solution for 10 minutes. Then add compound 3 (0.3 g, 0.75 mmol) into the mixture and react in a sealed device-mini-reactor. The reaction temperature is 130-150° C. in the oil bath and the reaction time is 90 minutes. The reacted solution is poured into 50 ml ice water, extracted with ethyl acetate, vacuum pressure reduction concentrated, and recrystallized from ethanol to get yellow compound 3e.

Mol. Wt.: 580.2533 ($C_{30}H_{36}N_4O_8$)

Yield: 35%

Mp: 150-151° C. (EtOH)

IR (KBr) cm$^{-1}$: 3215 (NH), 2960 (NH), 1732 (CO), 1694 (CO), 1632 (CO)

HRMS (EI) m/z calcd for $C_{30}H_{36}N_4O_8$ $^+[M+H]^+$: 580.2533. Found: 580.2527.

$^1$H-NMR (300 MHz, CDCl$_3$) δ (ppm):

1.01 (d, J=6.9 Hz, 6H, —CH$_3$), 1.05 (d, J=6.6 Hz, 6H, —CH$_3$), 2.04-2.08 (m, 2H, —CH$_2$—), 3.11 (d, J=5.7 Hz, 2H, —CH—), 3.30 (d, J=16.8 Hz, 2H, —CH$_2$—), 3.68 (d, J=17.1 Hz, 2H, —CH$_2$—), 3.75 (s, 6H, —OCH3), 7.73 (t, J=8.4 Hz, 2H, Ar—H$_{3,6}$), 8.02 (dd, J=7.5 Hz, 0.9 Hz, 2 H, Ar—H$_{4,5}$), 9.16 (dd, J=8.7 Hz, 0.9 Hz, 2H, Ar—H2,7), 12.59 (s, 2H, Ar—NH—)

$^{13}$C-NMR (300 MHz, CDCl$_3$) δ (ppm):

18.04, 18.48, 30.97, 51.02, 52.57, 66.94, 118.61 ($C_{8a,9a}$), 122.05 ($C_{2, 7}$), 126.39 ($C_{4, 5}$), 133.00 ($C_{3, 6}$), 135.01 ($C_{4a,5a}$), 140.81 ($C_{1, 8}$), 171.01 (NCO), 174.15 (CCO), 182.02 ($C_{10}O$), 189.81 ($C_9O$)

1,8-Bis[2-(sacrocine methyl ester)acetamido]anthraquinone (3f)

1,8-Bis[2-(leucine methyl ester)acetamido]anthraquinone (3g)

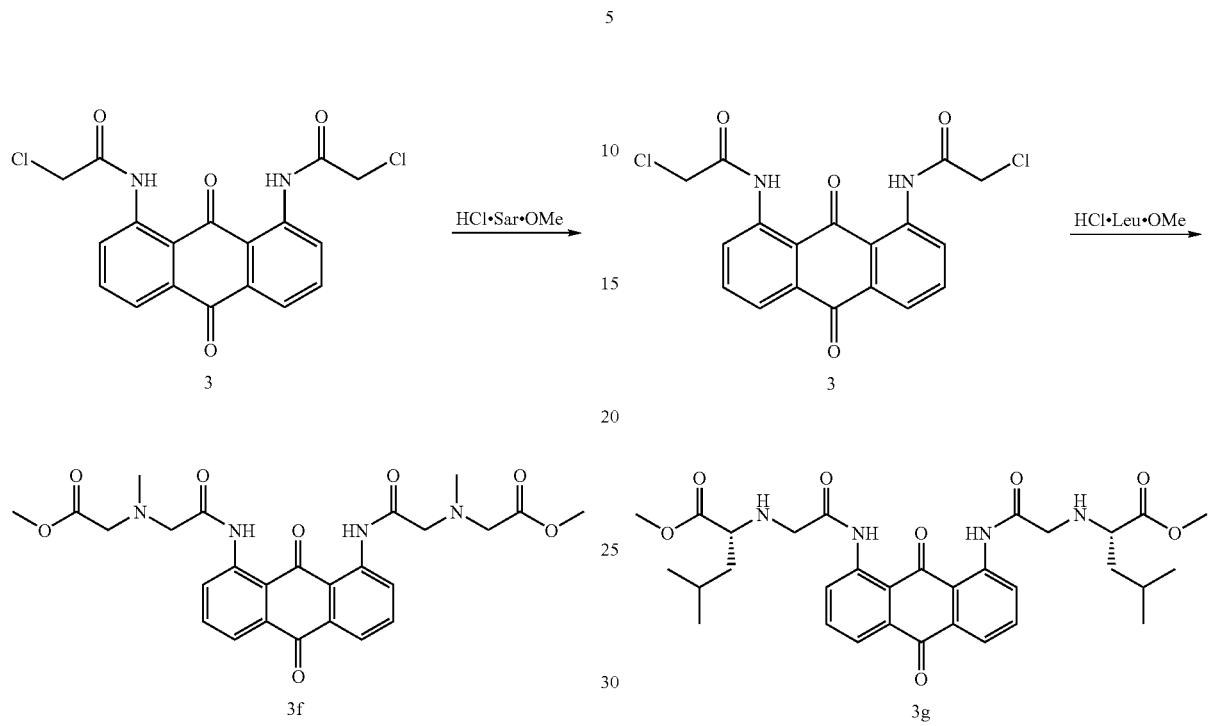

Add 0.84 g, 6 mmole Sacrocine methyl ester hydrochloride into DIPEA (2 ml, 12 mmole) and 20 ml dehydrated dimethylformamide (DMF) and stir the solution for 10 minutes. Then add compound 3 (0.3 g, 0.75 mmol) into the mixture and react in a sealed device-mini-reactor. The reaction temperature is 130-150° C. in the oil bath and the reaction time is 90 minutes. The reacted solution is poured into 50 ml ice water, extracted with ethyl acetate, vacuum pressure reduction concentrated, and recrystallized from ethanol to get yellow compound 3f.

Mol. Wt.: 524.1907 ($C_{26}H_{28}N_4O_8$)

Yield: 65%

Mp: 129-130° C. (EtOH)

IR (KBr) cm-1: 3206 (NH), 2947 (NH), 1739 (CO), 1691 (CO), 1630 (CO)

HRMS (EI) m/z calcd for $C_{26}H_{28}N_4O_8$ $^+$[M+H]$^+$: 524.1907. Found: 524.1906.

1H-NMR (300 MHz, CDCl$_3$) δ (ppm):

2.62 (s, 6H, —NCH$_3$), 3.56 (s, 4H, —CH$_2$—), 3.58 (s, 4H, —CH$_2$—), 3.69 (s, 6H, —OCH$_3$), 7.66 (t, J=7.8 Hz, 2H, Ar—H$_{3,6}$), 7.92 (d, J=6.9 Hz, 2H, Ar—H$_{4,5}$), 9.08 (d, J=8.1 Hz, 2H, Ar—H$_{27}$), 12.52 (s, 2H, Ar—NH—)

13C-NMR (300 MHz, CDCl$_3$) δ (ppm):

42.18, 50.78, 57.15, 60.89, 118.62 ($C_{8a,9a}$), 121.92 ($C_{2,7}$), 126.36 ($C_{4,5}$), 132.87 ($C_{3,6}$), 134.84 ($C_{4a,5a}$), 140.73 ($C_{1,8}$), 170.23 (NCO), 170.31 (CCO), 181.90 ($C_{10}$O), 189.73 ($C_9$O)

Add 1.1 g, 6 mmole Leucine methyl ester hydrochloride into DIPEA (2 ml, 12 mmole) and 20 ml dehydrated dimethylformamide (DMF) and stir the solution for 10 minutes. Then add compound 3 (0.3 g, 0.75 mmol) into the mixture and react in a sealed device-mini-reactor. The reaction temperature is 130-150° C. in the oil bath and the reaction time is 90 minutes. The reacted solution is poured into 50 ml ice water, extracted with ethyl acetate, and recrystallized from ethanol to get compound 3g.

Mol. Wt.: 608.2846 ($C_{32}H_{40}N_4O_8$)

Yield: 40%

Mp: 238-239° C. (EtOH)

IR (KBr) cm-1: 3206 (NH), 2955 (NH), 1737 (CO), 1693 (CO), 1630 (CO)

HRMS (EI) m/z calcd for $C_{32}H_{40}N_4O_8$ $^+$[M+H]$^+$: 608.2846. Found: 608.2832.

$^1$H-NMR (300 MHz, CDCl$_3$) δ (ppm):

0.83 (d, J=6.6 Hz, 6H, —CH$_3$), 0.88 (d, J=6.6 Hz, 6H, —CH$_3$), 1.54-1.73 (m, 4H, —CH$_2$—), 1.88-1.93 (m, 2H, —CH—), 3.33-3.38 (m, H, —CH—), 3.35 (d, J=17.1 Hz, 2H, —CH$_2$—), 3.68 (d, J=17.1 Hz, 2H, —CH$_2$—), 3.75 (s, 6H, —OCH$_3$), 7.80 (t, J=8.1 Hz, 2H, Ar—H$_{3,6}$), 8.08 (dd, J=7.5 Hz, 1.2 Hz, 2 H, Ar—H$_{4,5}$), 9.26 (dd, J=8.4 Hz, 1.2 Hz, 2H, Ar—H$_2$, 7), 12.82 (s, 2H, Ar—NH—)

$^{13}$C-NMR (300 MHz, CDCl$_3$) δ (ppm):

22.06, 24.15, 42.09, 51.17, 51.90, 59.36, 118.35 ($C_{8a,9a}$), 121.91 ($C_{2,7}$), 126.15 ($C_{4,5}$), 132.89 ($C_{3,6}$), 134.99 ($C_{4a,5a}$), 140.74 ($C_{1,8}$), 171.04 (NCO), 174.97 (CCO), 181.83 ($C_{10}$O), 189.65 ($C_9$O)

17

(L)-1,8-Bis[2-(alaline methyl ester)acetamido]anthraquinone (3h)

18

(D)-1,8-Bis[2-(alaline methyl ester)acetamido]anthraquinone (3i)

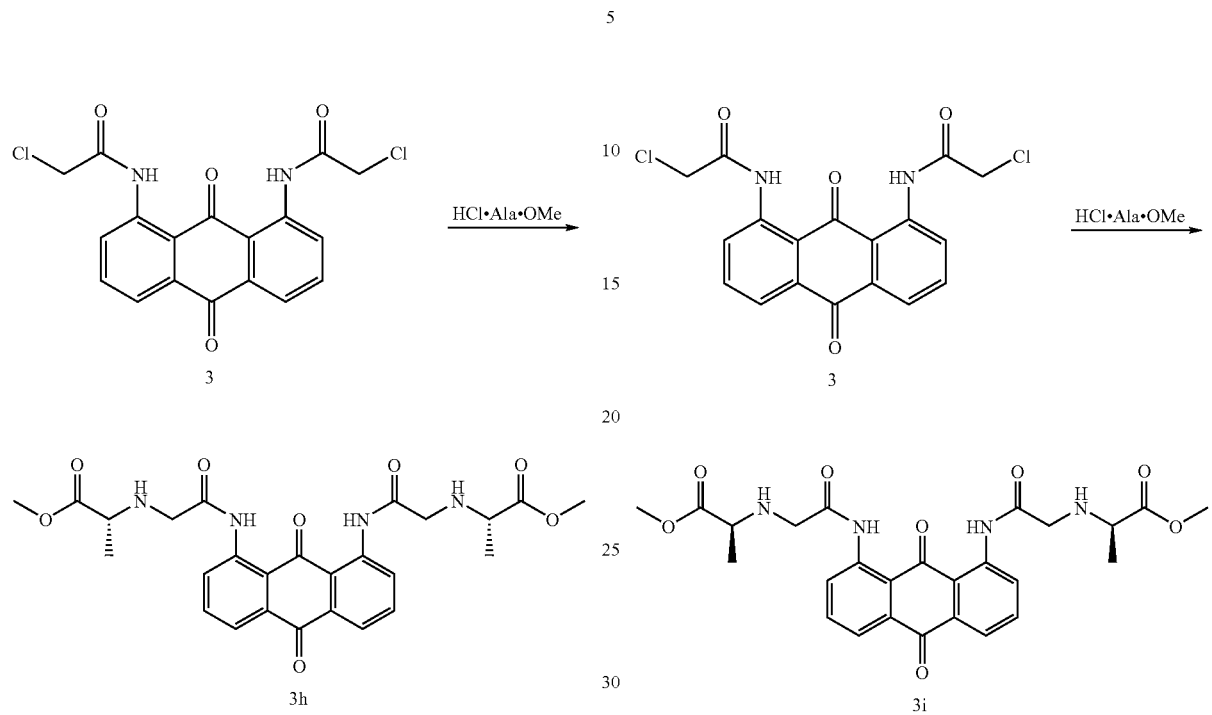

Add 0.84 g, 6 mmole (L)Alaline methyl ester hydrochloride into DIPEA (2 ml, 12 mmole) and 20 ml dehydrated dimethylformamide (DMF) and stir the solution for 10 minutes. Then add compound 3 (0.3 g, 0.75 mmol) into the mixture and react in a sealed device-mini-reactor. The reaction temperature is 130-150° C. in the oil bath and the reaction time is 90 minutes. The reacted solution is poured into 50 ml ice water, extracted with ethyl acetate, and recrystallized from ethanol to get compound 3h.

Mol. Wt.: 524.1907 ($C_{26}H_{28}H_4O_8$)

Yield: 41%

Mp: 119-120° C. (EtOH)

IR (KBr) cm-1: 3194 (NH), 2938 (NH), 1738 (CO), 1694 (CO), 1628 (CO)

HRMS (EI) m/z calcd for $C_{26}H_{28}N_4O_8$ $^+$[M+H]$^+$: 524.1907. Found: 524.1904.

$^1$H-NMR (300 MHz, CDCl$_3$) δ (ppm):

1.46 (d, J=6.9 Hz, 6H, —CH$_3$), 3.38 (d, J=17.4 Hz, 2H, —CH$_2$—), 3.46 (q, J=6.9 Hz, 2H, —CH—), 3.70 (d, J=17.4 Hz, 2H, —CH$_2$—), 3.75 (s, 6H, —OCH$_3$), 7.77 (t, J=7.8 Hz, 2H, Ar—H$_{3,6}$), 8.06 (dd, J=7.5 Hz, 1.2 Hz, 2H, Ar—H$_{4,5}$), 9.23 (dd, J=8.4 Hz, 1.2 Hz, 2H, Ar—H$_{27}$), 12.84 (s, 2H, Ar—NH—)

$^{13}$C-NMR (300 MHz, CDCl$_3$) δ (ppm):

18.29, 51.36, 51.52, 55.94, 118.18 ($C_{8a,9a}$), 121.79 ($C_{2,7}$), 126.01 ($C_{4,5}$), 132.67 ($C_{3,6}$), 134.93 ($C_{4a,5a}$), 140.69 ($C_{1,8}$), 170.18 (NCO), 174.86 (CCO), 181.70 ($C_{10}$O), 189.60 ($C_9$O)

Add 0.84 g, 6 mmole (D)Alaline methyl ester hydrochloride into DIPEA (2 ml, 12 mmole) and 20 ml dehydrated dimethylformamide (DMF) and stir the solution for 10 minutes. Then add compound 3 (0.3 g, 0.75 mmol) into the mixture and react in a sealed device-mini-reactor. The reaction temperature is 130-150° C. in the oil bath and the reaction time is 90 minutes. The reacted solution is poured into 50 ml ice water, extracted with ethyl acetate, and recrystallized from ethanol to get compound 3l.

Mol. Wt.: 524.1907 ($C_{26}H_{28}N_4O_8$)

Yield: 45%

Mp: 118-119° C. (EtOH)

IR (KBr) cm-1: 3194 (NH), 2952 (NH), 1738 (CO), 1694 (CO), 1628 (CO)

HRMS (EI) m/z calcd for $C_{26}H_{28}N_4O_8$ $^+$[M+H]$^+$: 524.1907. Found: 524.1908.

$^1$H-NMR (300 MHz, CDCl$_3$) δ (ppm):

1.45 (d, J=7.2 Hz, 6H, —CH$_3$), 3.38 (d, J=17.4 Hz, 2H, —CH$_2$—), 3.46 (q, J=6.9 Hz, 2H, —CH—), 3.70 (d, J=17.4 Hz, 2H, —CH$_2$—), 3.75 (s, 6H, —OCH$_3$), 7.77 (t, J=7.8 Hz, 2H, Ar—H$_{3,6}$), 8.06 (dd, J=7.5 Hz, 1.2 Hz, 2H, Ar—H$_{4,5}$), 9.24 (dd, J=8.4 Hz, 1.2 Hz, 2H, Ar—H$_{2,7}$), 12.85 (s, 2H, Ar—NH—)

$^{13}$C-NMR (300 MHz, CDCl$_3$) δ (ppm):

18.23, 51.28, 51.45, 55.89, 118.03 ($C_{8a,9a}$), 121.64 ($C_{2,7}$), 125.90 ($C_{4,5}$), 132.54 ($C_{3,6}$), 134.83 ($C_{4a,5a}$), 140.63 ($C_{1,8}$), 170.08 (NCO), 174.77 (CCO), 181.51 ($C_{10}$O), 189.43 ($C_9$O)

(S)-1,8-Bis[2-(phenylglycin methyl ester)acetamido]anthraquinone(3j)

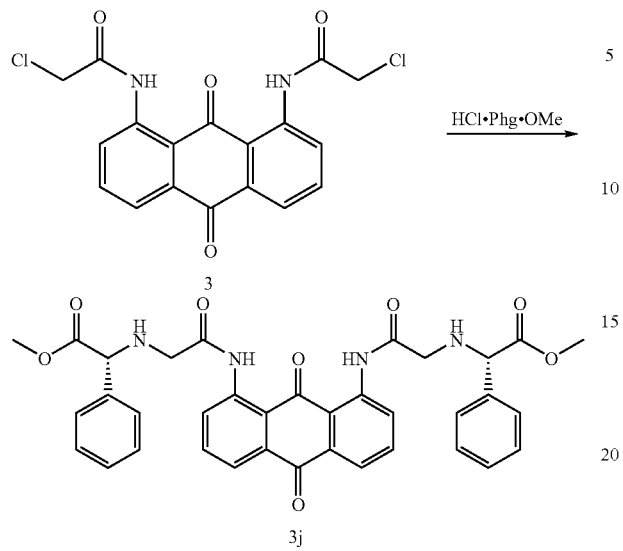

Add 1.2 g, 6 mmole (S)-phenylglycine methyl ester hydrochloride into DIPEA (2 ml, 12 mmole) and 20 ml dehydrated dimethylformamide (DMF) and stir the solution for 10 minutes. Then add compound 3 (0.3 g, 0.75 mmol) into the mixture and react in a sealed device-mini-reactor. The reaction temperature is 130-150° C. in the oil bath and the reaction time is 90 minutes. The reacted solution is poured into 50 ml ice water, extracted with ethyl acetate, and recrystallized from ethanol to get compound 3j.

Mol. Wt.: 648.2220 ($C_{36}H_{32}N_4O_8$)

Yield: 33%

Mp: 256-260° C. (EtOH)

IR (KBr) cm$^{-1}$: 3249 (NH), 2938 (NH), 1741 (CO) 1702 (CO), 1629 (CO)

HRMS (EI) m/z calcd for $C_{36}H_{32}N_4O_8$ $^+$[M+H]$^+$: 648.2220. Found: 648.2226.

$^1$H-NMR (300 MHz, CDCl$_3$) δ (ppm):

3.42 (d, J=17.4 Hz, 2H, —CH$_2$—), 3.51 (d, J=17.7 Hz, 2H, —CH$_2$—), 3.69 (s, 6H, —OCH$_3$), 4.52 (s, 2H, —CH—), 7.33-7.36 (m, 10H, —C$_6$H$_5$) 7.69 (t, J=8.1 Hz, 2H, Ar—H$_{3,6}$), 7.94 (d, J=7.2 Hz, 2H, Ar—H$_{4,5}$), 9.07 (d, J=8.1 Hz, 2H, Ar—H$_{27}$), 11.94 (s, 2H, Ar—NH—)

$^{13}$C-NMR (300 MHz, CDCl$_3$) δ (ppm):

24.89, 51.70, 51.45, 64.39, 117.62 ($C_{8a,9a}$), 121.84 ($C_{2,7}$), 125.98 ($C_{4,5}$), 127.14, 128.15, 128.47, 132.79 ($C_{3,6}$), 135.10 ($C_{4a, 5a}$), 135.43, 141.69 ($C_{1, 8}$), 169.04 (NCO), 172.20 (CCO), 181.66 ($C_{10}$O), 191.16 ($C_9$O)

1,8-Bis[2-(isobutylamino)acetamido]anthraquinone (3k)

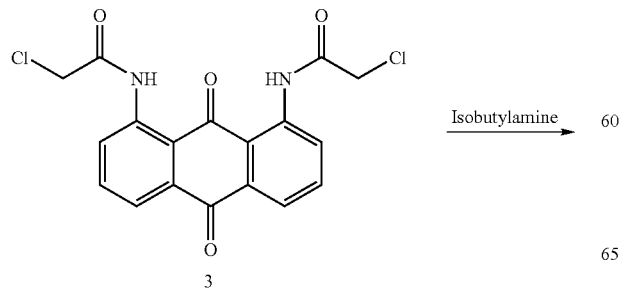

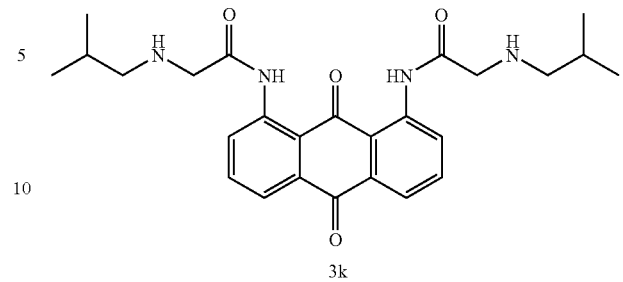

Add 0.4 g, 1.0 mmol 1,8-bis(chloroacetamido)anthraquinone (compound 3) with pyridine (0.5 ml), and 0.6 ml, 6 mmole Isobutylamine, dissolved in 20 ml dehydrated dimethylformamide (DMF). The mixture is reacted in a mini-reactor. The reaction temperature is 120° C. in the oil bath and the reaction time is 30 minutes. The reacted mixture is poured into 50 ml ice water and is filtered to collect precipitate. The precipitate is recrystallized from ethanol to get yellow compound 3k.

Mol. Wt.: 464.2424 ($C_{26}H_{32}N_4O_4$)

Yield: 40%

Mp: 139-140° C. (EtOH)

IR (KBr) cm-1: 3196 (NH), 2947 (NH), 1693 (CO), 1630 (CO)

HRMS (EI) m/z calcd for $C_{26}H_{32}N_4O_4$ $^+$[M+H]$^+$: 464.2424. Found: 464.2424.

$^1$H-NMR (300 MHz, CDCl$_3$) δ (ppm):

0.95 (d, J=6.3 Hz, 12H, —CH$_3$), 1.85-1.89 (m, 2H, —CH—), 2.55 (d, J=6.9 Hz, 4H, —CH$_2$—), 3.55 (s, 4H, —CH$_2$—), 7.77 (t, J=8.1 Hz, 2H, Ar—H$_{3,6}$), 8.06 (d, J=7.5 Hz, 2H, Ar—H$_{4,5}$), 9.23 (d, J=8.4 Hz, 2H, Ar—H$_{27}$), 12.75 (s, 2H, Ar—NH—)

$^{13}$C-NMR (300 MHz, CDCl$_3$) δ (ppm):

19.92, 27.79, 53.72, 57.64, 118.60 ($C_{8a,9a}$), 121.93 ($C_{2, 7}$), 126.32 ($C_{4, 5}$), 132.98 ($C_{3, 6}$), 134.69 ($C_{4a,5a}$), 140.91 ($C_{1, 8}$), 171.83 (NCO), 182.12 ($C_{10}$O), 189.93 ($C_9$O)

1,8-Bis[2-(diethylamino)acetamido]anthraquinone (3l)

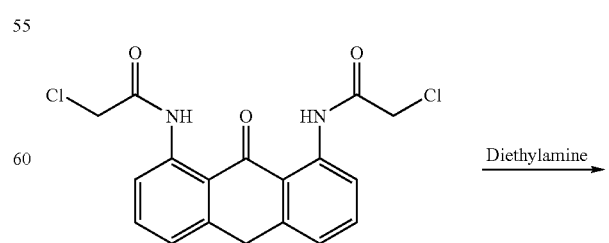

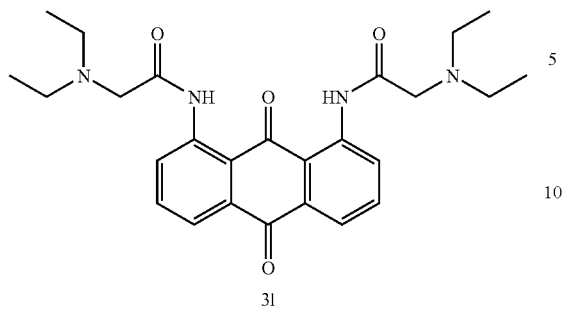

3l

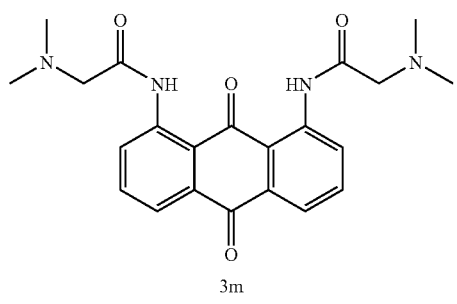

3m

Add 0.4 g, 1.0 mmol 1,8-bis(chloroacetamido)anthraquinone (compound 3) with pyridine (0.5 ml), and 0.6 ml, 6 mmole Diethylamine, dissolved in 20 ml dehydrated dimethylformamide (DMF). The mixture is reacted in a mini-reactor. The reaction temperature is 120° C. in the oil bath and the reaction time is 30 minutes. The reacted mixture is poured into 50 ml ice water and is filtered to collect precipitate. The precipitate is recrystallized from ethanol to get yellow compound 3l.

Mol. Wt.: 464.2424 ($C_{26}H_{32}N_4O_4$)

Yield: 70%

Mp: 228-229° C. (EtOH)

IR (KBr) cm-1: 3187 (NH), 2968 (NH), 1693 (CO), 1628 (CO)

HRMS (EI) m/z calcd for $C_{26}H_{32}N_4O_4$ $^+[M+H]^+$: 464.2424. Found: 464.2424.

$^1$H-NMR (300 MHz, CDCl$_3$) δ (ppm):

1.133 (t, J=6.9 Hz, 12H, —CH$_3$), 2.75 (q, J=7.2 Hz, 8H, —CH$_2$—), 3.33 (s, 4H, —CH$_2$—), 7.71 (t, J=8.1 Hz, 2H, Ar—H$_{3,6}$), 8.00 (dd, J=7.5 Hz, 1.2 Hz, 2H, Ar—H$_{4,5}$), 9.19 (dd, J=8.4 Hz, 1.2 Hz, 2H, Ar—H$_{27}$), 12.75 (s, 2H, Ar—NH—)

$^{13}$C-NMR (300 MHz, CDCl$_3$) δ (ppm):

11.28, 47.97, 58.27, 118.88 ($C_{8a,9}$a), 121.89 ($C_{2,7}$), 126.55 ($C_{4,5}$), 133.03 ($C_{3,6}$), 134.67 ($C_{4a,5a}$), 140.82 ($C_{1,8}$), 172.01 (NCO), 182.19 ($C_{10}$O), 189.47 ($C_9$O)

1,8-Bis[2-(dimethylamino)acetamido]anthraquinone (3m)

Add 0.4 g, 1.0 mmol 1,8-bis(chloroacetamido)anthraquinone (compound 3) with 0.5 ml TEA, and 0.4 ml, 6 mmole Dimethylamine, dissolved in 20 ml dehydrated dimethylformamide (DMF). The mixture is reacted in a mini-reactor. The reaction temperature is 120° C. in the oil bath and the reaction time is 30 minutes. The reacted mixture is poured into 50 ml ice water and is filtered to collect precipitate. The precipitate is recrystallized from ethanol to get yellow compound 3m.

Mol. Wt.: 408.1798 ($C_{22}H_{24}N_4O_4$)

Yield: 64%

Mp: 194-195° C. (EtOH)

IR (KBr) cm-1: 3206 (NH), 2779 (NH), 1693 (CO), 1633 (CO)

HRMS (EI) m/z calcd for $C_{22}H_{24}N_4O_4$ $^+[M+H]^+$: 408.1798. Found: 408.1798.

$^1$H-NMR (300 MHz, CDCl$_3$) δ (ppm):

2.49 (s, 8H, —CH$_3$), 3.25 (s, 4H, —CH$_2$—), 7.77 (t, J=7.8 Hz, 2H, Ar—H$_{3,6}$), 8.06 (dd, J=7.5 Hz, 1.2 Hz, 2H, Ar—H$_{4,5}$), 9.24 (dd, J=8.7 Hz, 1.2 Hz, 2 H, Ar—H$_{2,7}$), 12.69 (s, 2H, Ar—NH—)

$^{13}$C-NMR (300 MHz, CDCl$_3$) δ (ppm):

45.46, 64.23, 118.64 ($C_{8a,9a}$), 121.79 ($C_{2,7}$), 126.36 ($C_{4,5}$), 132.80 ($C_{3,6}$), 134.62 ($C_{4a,5a}$), 140.64 ($C_{1,8}$), 170.50 (NCO), 181.88 ($C_{10}$O), 189.35 ($C_9$O)

1,8-Bis[2-(dipropylamino)acetamido]anthraquinone (3n)

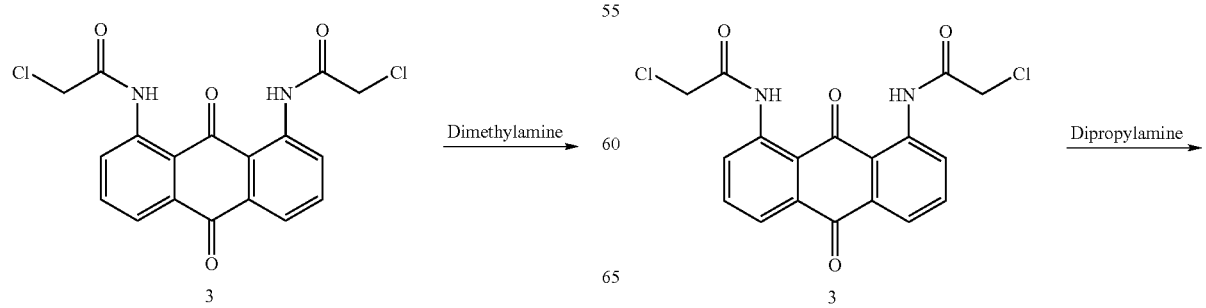

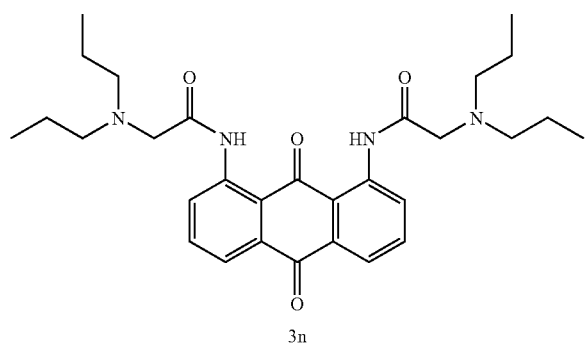

3n

Add 0.4 g, 1.0 mmol 1,8-bis(chloroacetamido)anthraquinone (compound 3) with 0.5 ml TEA, and 0.7 ml, 6 mmole Dipropylamine, dissolved in 20 ml dehydrated dimethylformamide (DMF). The mixture is reacted in a mini-reactor. The reaction temperature is 120° C. in the oil bath and the reaction time is 30 minutes. The reacted mixture is poured into 50 ml ice water and is filtered to collect precipitate. The precipitate is recrystallized from ethanol to get yellow compound 3n.

Mol. Wt.: 520.3050 ($C_{30}H_{40}N_4O_4$)

Yield: 82%

Mp: 129-130° C. (EtOH)

IR (KBr) cm-1: 3167 (NH), 2957 (NH), 1694 (CO), 1628 (CO)

HRMS (EI) m/z calcd for $C_{30}H_{40}N_4O_4$ $^+[M+H]^+$: 520.3050. Found: 520.3048.

1H-NMR (300 MHz, CDCl$_3$) δ (ppm):

0.91 (t, J=7.5 Hz, 12H, —CH$_3$), 1.55-1.62 (m, 8H, —CH$_2$—), 2.62-2.67 (m, 8H, —N—CH$_2$—), 3.38 (s, 4H, —CH$_2$—), 7.76 (t, J=8.1 Hz, 2H, Ar—H$_{3,6}$), 8.07 (dd, J=7.8 Hz, 1.5 Hz, 2H, Ar—H$_{4,5}$), 9.23 (dd, J=8.7 Hz, 1.5 Hz, 2 H, Ar—H$_{2,7}$), 12.53 (s, 2H, Ar—NH—)

$^{13}$C-NMR (300 MHz, CDCl$_3$) δ (ppm):

11.11, 19.53, 56.73, 59.37, 118.63 ($C_{8a,9a}$), 121.73 ($C_{2,7}$), 126.33 ($C_{4,5}$), 132.97 ($C_{3,6}$), 134.70 ($C_{4a,5a}$), 140.94 ($C_{1,8}$), 171.68 (NCO), 181.95 ($C_{10}$O), 189.58 ($C_9$O)

1,8-Bis[2-(isopropylamino)acetamido]anthraquinone
(3o)

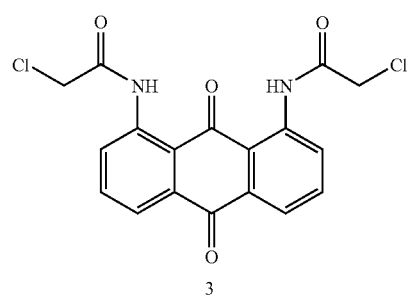

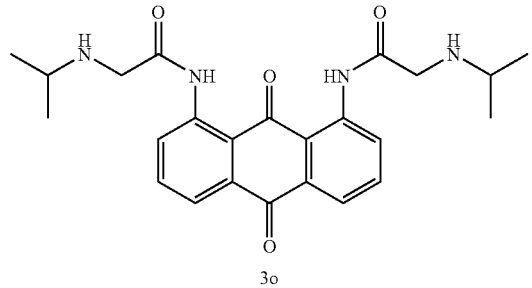

3o

Add 0.4 g, 1.0 mmol 1,8-bis(chloroacetamido)anthraquinone (compound 3) with 0.5 ml TEA, and 0.6 ml, 6 mmole isopropylamine, dissolved in 20 ml dehydrated dimethylformamide (DMF). The mixture is reacted in a mini-reactor. The reaction temperature is 120° C. in the oil bath and the reaction time is 30 minutes. The reacted mixture is poured into a little bit ice water and is filtered to collect precipitate. The precipitate is recrystallized from ethanol to get yellow compound 3o.

Mol. Wt.: 436.2111 ($C_{24}H_{28}N_4O_4$)

Yield: 65%

Mp: 196-197° C. (EtOH)

IR (KBr) cm$^-$1: 3183 (NH), 2962 (NH), 1698 (CO), 1628 (CO) HRMS (EI) m/z calcd for $C_{24}H_{28}N_4O_4$ $^+[M+H]^+$: 436.2111. Found: 436.2101.

$^1$H-NMR (300 MHz, CDCl$_3$) δ (ppm):

1.17 (d, J=5.4 Hz, 12H, —CH$_3$), 2.89-2.93 (m, 2H, —CH—), 3.55 (s, 4H, —CH$_2$—), 7.76 (t, J=8.4 Hz, 2H, Ar—H$_{3,6}$), 8.04 (d, J=7.5 Hz, 2H, Ar—H$_{4,5}$), 9.23 (d, J=8.7 Hz, 2H, Ar—H$_{27}$), 12.76 (s, 2H, Ar—NH—)

$^{13}$C-NMR (300 MHz, CDCl$_3$) δ (ppm):

22.38, 48.67, 51.30, 118.57 ($C_{8a,9a}$), 121.95 ($C_{2,7}$), 126.27 ($C_{4,5}$), 133.01 ($C_{3,6}$), 135.04 ($C_{4a,5a}$), 140.95 ($C_{1,8}$), 172.27 (NCO), 182.22 ($C_{10}$O), 189.96 ($C_9$O)

1,8-Bis[2-(ethanamino)acetamido]anthraquinone
(3p)

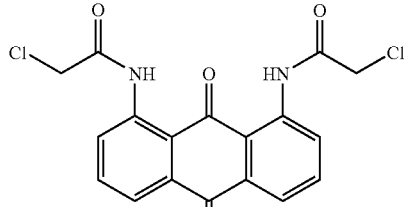

3

Ethylamine →

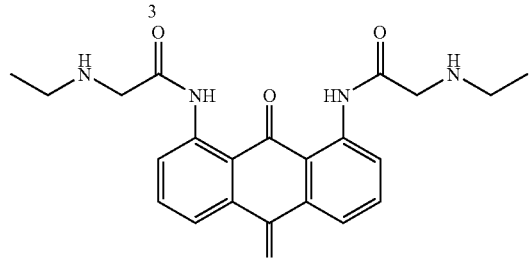

3p

Add 0.4 g, 1.0 mmol 1,8-bis(chloroacetamido)anthraquinone (compound 3) with 0.5 ml TEA, and 0.5 ml, 6 mmole ethanamine, dissolved in 20 ml dehydrated dimethylformamide (DMF). The mixture is reacted in a mini-reactor. The reaction temperature is 120° C. in the oil bath and the reaction time is 30 minutes. The reacted mixture is poured into 50 ml ice water and is filtered to collect precipitate. The precipitate is recrystallized from ethanol to get yellow compound 3p.

Mol. Wt.: 408.1798 ($C_2H_{24}N_4O_4$)
Yield: 52%
Mp: 182-183° C. (EtOH)
IR (KBr) cm$^{-1}$: 3175 (NH), 2957 (NH), 1694 (CO), 1628 (CO)
HRMS (EI) m/z calcd for $C_{22}H_{24}N_4O_4$ $^+$[M+H]$^+$: 408.1798. Found: 408.1801.
$^1$H-NMR (300 MHz, CDCl$_3$) δ (ppm)
1.24 (t, J=6.9 Hz, 6H, —CH$_3$), 2.79 (q, J=6.9 Hz, 4H, —CH$_2$—), 3.55 (s, 4H, —CH$_2$—), 7.75 (t, J=8.1 Hz, 2H, Ar—H$_{3,6}$), 8.04 (d, J=7.5 Hz, 2H, Ar—H$_{4,5}$), 9.23 (d, J=8.4 Hz, 2H, Ar—H$_{2,7}$), 12.82 (s, 2H, Ar—NH—)
$^{13}$C-NMR (300 MHz, CDCl$_3$) δ (ppm)
14.70, 43.71, 53.24, 118.52 ($C_{8a,9b}$), 121.63 ($C_{2,7}$), 126.01 ($C_{4,5}$), 132.70 ($C_{3,6}$), 134.75 ($C_{4a,5a}$), 140.77 ($C_{1,8}$), 171.79 (NCO), 181.73 ($C_{10}$O), 189.48 ($C_9$O)

1,8-Bis [2-(3-(trifluoromethyl)benzylamino)acetamido]anthraquinone (3q)

Add 0.4 g, 1.0 mmol 1,8-bis(chloroacetamido)anthraquinone (compound 3) with 0.5 ml TEA, and 0.8 ml, 6 mmole 3-(trifluoromethyl)benzylamine, dissolved in 20 ml dehydrated dimethylformamide (DMF). The mixture is reacted in a mini-reactor. The reaction temperature is 120° C. in the oil bath and the reaction time is 30 minutes. The reacted mixture is poured into 50 ml ice water and is filtered to collect precipitate. The precipitate is recrystallized from ethanol to get yellow compound 3q.

Mol. Wt.: 668.1858 ($C_{34}H_{26}F_6N_4O_4$)
Yield: 66%
Mp: 190-191° C. (EtOH)
IR (KBr) cm$^{-1}$: 3202 (NH), 2836 (NH), 1693 (CO), 1632 (CO) HRMS (EI) m/z calcd for $C_{34}H_{26}F_6N_4O_4$ $^+$[M+H]$^+$: 668.1858. Found: 668.1859.
$^1$H-NMR (300 MHz, CDCl$_3$) δ (ppm):
3.40 (s, 4H, —CH$_2$—), 3.77 (s, 4H, —CH$_2$—), 7.74-7.54 (m, 6H, Ar—H$_{4,5,6}$), 7.65 (s, 2H, Ar'—H$_2$) 7.75 (t, J=8.1 Hz, 2H, Ar—H$_{3,6}$), 8.08 (d, J=7.2 Hz, 2H, Ar—H$_{4,5}$), 9.23 (d, J=8.4 Hz, 2H, Ar—H$_{2,7}$), 12.91 (s, 2H, Ar—NH—)
$^{13}$C-NMR (300 MHz, CDCl$_3$) δ (ppm):
52.80, 52.87, 114.95, 118.67 ($C_{8a,9b}$, 122.17 ($C_{2,7}$), 123.87, 124.52, 126.29 ($C_{4,5}$), 128.50, 131.17, 133.04 ($C_{3,6}$), 135.21 ($C_{4a,5a}$), 139.85, 140.81 ($C_{1,8}$), 171.05 (NCO), 182.14 ($C_{10}$O), 190.28 ($C_9$O)

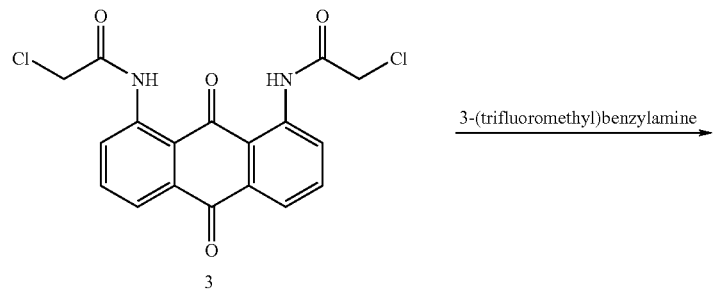

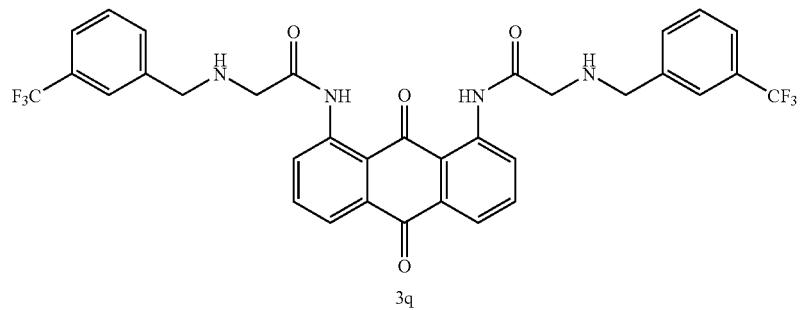

1,8-Bis[2-(ethylmethylamino)acetamido]anthraquinone(3r)

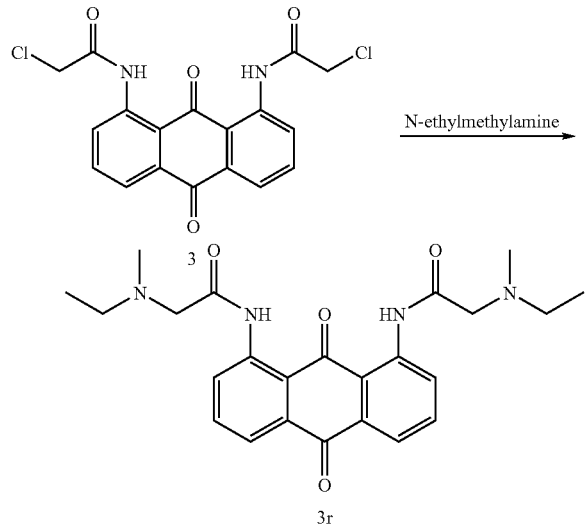

Add 0.4 g, 1.0 mmol 1,8-bis(chloroacetamido)anthraquinone (compound 3) with pyridine (0.5 ml), and 0.5 ml, 6 mmole N-ethylmethylamine, dissolved in 20 ml dehydrated dimethylformamide (DMF). The mixture is reacted in a mini-reactor. The reaction temperature is 120° C. in the oil bath and the reaction time is 30 minutes. The reacted mixture is poured into 50 ml ice water and is filtered to collect precipitate. The precipitate is recrystallized from ethanol to get yellow compound 3r.

Mol. Wt.: 436.2111 ($C_{24}H_{28}N_4O_4$)
Yield: 79%
Mp: 186-187° C. (EtOH)
IR (KBr) cm$^{-1}$: 3215 (NH), 2967 (NH), 1665 (CO)
HRMS (EI) m/z calcd for $C_{24}H_{28}N_4O_4$ $^+$[M+H]$^+$: 436.2111. Found: 436.2108.
$^1$H-NMR (300 MHz, CDCl$_3$) δ (ppm):
1.18 (t, J=7.2 Hz, 6H, —CH$_3$), 3.48 (s, 6H, —CH$_3$), 2.64 (q, J=7.2 Hz, 4 H, —CH$_2$—), 3.29 (s, 4H, —CH$_2$—), 7.76 (t, J=8.4 Hz, 2H, Ar—H$_{3,6}$), 8.06 (d, J=7.5 Hz, 2H, Ar—H$_{4,5}$), 9.22 (d, J=8.7 Hz, 2H, Ar—H$_{27}$), 12.62 (s, 2H, Ar—NH—)
$^{13}$C-NMR (300 MHz, CDCl$_3$) δ (ppm):
11.66, 42.25, 51.15, 61.73, 118.84 ($C_{8a,9a}$), 121.93 ($C_{2,7}$), 126.52 ($C_{4,5}$), 132.94 ($C_{3,6}$), 134.73 ($C_{4a,5a}$), 140.74 ($C_{1,8}$), 171.20 (NCO), 182.19 ($C_{10}$O), 189.49 ($C_9$O)

1,8-Bis[2-(methylethylamino)acetamido]anthraquinone(3s)

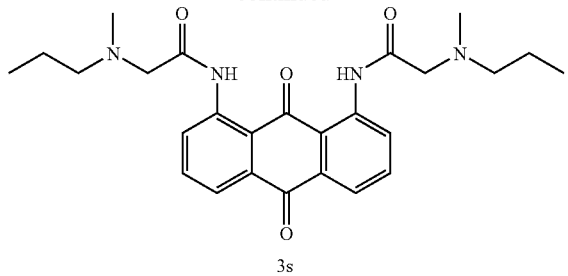

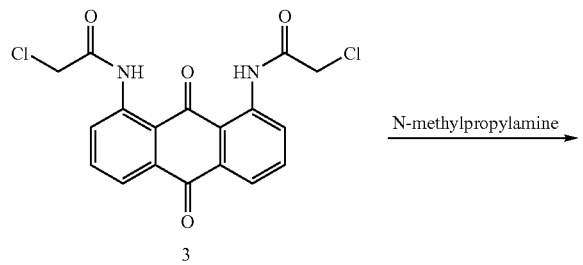

Add 0.4 g, 1.0 mmol 1,8-bis(chloroacetamido)anthraquinone (compound 3) with pyridine (0.5 ml), and 0.6 ml, 6 mmole N-methylpropylamine, dissolved in 20 ml dehydrated dimethylformamide (DMF). The mixture is reacted in a mini-reactor. The reaction temperature is 120° C. in the oil bath and the reaction time is 30 minutes. The reacted mixture is poured into 50 ml ice water and is filtered to collect precipitate. The precipitate is recrystallized from ethanol to get yellow compound 3s.

Mol. Wt.: 464.2424 ($C_{26}H_{32}N_4O_4$)
Yield: 67%
Mp: 159-160° C. (EtOH)
IR (KBr) cm$^{-1}$: 3215 (NH), 2958 (NH), 1692 (CO), 1631 (CO)
HRMS (EI) m/z calcd for $C_{26}H_{32}N_4O_4$ $^+$[M+H]$^+$: 464.2424. Found: 464.1654.
$^1$H-NMR (300 MHz, CDCl$_3$) δ (ppm):
0.92 (t, J=7.2 Hz, 6H, —CH$_3$), 1.61 (q, J=7.2 Hz, 4H, —CH$_2$—), 2.48 (s, 6 H, —CH$_3$), 2.51 (t, J=7.5 Hz, 4H, —CH$_2$—), 3.28 (s, 4H, —CH$_2$—), 7.73 (t, J=8.4 Hz, 2H, Ar—H$_{3,6}$), 8.02 (d, J=7.5 Hz, 2H, Ar—H$_{4,5}$), 9.18 (d, J=8.7 Hz, 2H, Ar—H$_{27}$), 12.55 (s, 2H, Ar—NH—)
$^{13}$C-NMR (300 MHz, CDCl$_3$) δ (ppm):
11.04, 19.76, 42.80, 59.44, 62.33, 118.90 ($C_{8a,9a}$), 121.92 ($C_{2,7}$), 126.53 ($C_{4,5}$), 133.04 ($C_{3,6}$), 134.73 ($C_{4a,5a}$), 140.79 ($C_{1,8}$), 171.07 (NCO), 182.20 ($C_{10}$O), 189.52 ($C_9$O)

1,8-Bis[2-(tert-butyl-serine methyl ester)acetamido]anthraquinone (3t)

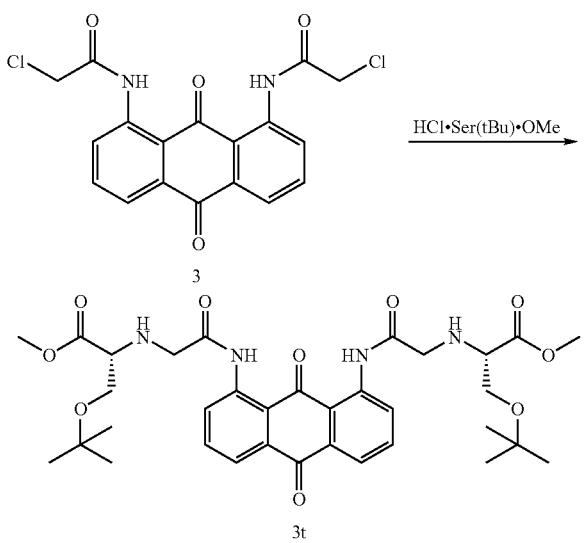

Add 1.2 g, 6 mmole O-tert-butyl-serine methyl ester hydrochloride with DIPEA (2 ml, 12 mmole), and 20 ml dehydrated dimethylformamide (DMF) and stir the mixture for 10 minutes. Then add 0.3 g, 0.75 mmol the compound 3 into the mixture and then react in a mini-reactor. The reaction temperature is 130-150° C. in the oil bath and the reaction time is 90 minutes. The reacted mixture is poured into 50 ml ice water, extracted with ethyl acetate and recrystallized from ethanol to get yellow compound 3t.

Mol. Wt.: 668.3057 ($C_{34}H_{44}N_4O_{10}$)

Yield: 44%

Mp: 139-140° C. (EtOH)

IR (KBr) cm$^{-1}$: 3206 (NH), 2967 (NH), 1691 (CO)

FAB-MS m/z (%): 670 ([M+2]+, 100), 671 ([M+1]+, 44.33)

$^1$H-NMR (300 MHz, CDCl$_3$) δ (ppm):
1.11 (s, 18H, —CH$_3$), 3.46-3.55 (m, 8H, —CH$_2$—), 3.70 (s, 6H, —OCH$_3$), 3.73 (s, 4H, —CH$_2$—), 4.21-4.30 (m, 2H, —CH—), 7.69 (t, J=8.1 Hz, 2H, Ar—H$_{3,6}$), 7.96 (d, J=6.3 Hz, 2H, Ar—H$_{4,5}$), 9.15 (d, J=8.4 Hz, 2H, Ar—H$_{2,7}$), 12.85 (s, 2H, Ar—NH—)

$^{13}$C-NMR (300 MHz, CDCl$_3$) δ (ppm):
26.69, 42.88, 51.22, 61.17, 62.09, 72.81, 118.64 ($C_{8a,9a}$), 121.75 ($C_{2,7}$), 126.14 ($C_{4,5}$), 132.92 ($C_{3,6}$), 134.86 ($C_{4a,5a}$), 140.79 ($C_{1,8}$), 165.57 (NCO), 172.30 (CCO), 182.08 ($C_{10}$O), 189.89 ($C_9$O)

1,8-Bis(3-chloropropionamido)anthraquinone (4)

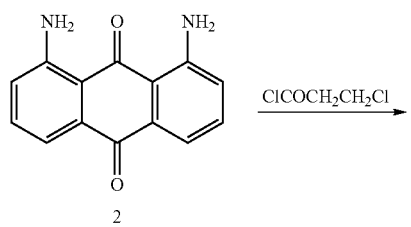

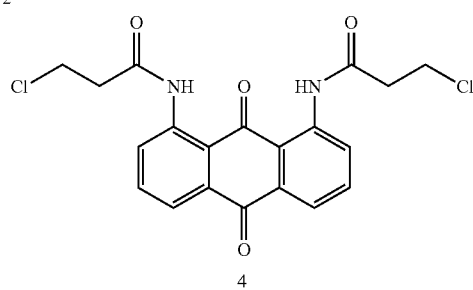

Dissolve 1,8-diaminoanthraquinone (0.476 g, 2 mmol) in N,N-dimethylformamide (20 ml). Add pyridine (0.5 ml) as catalyst in an ice bath and then add 3-chloropropioyl chloride (0.6 ml, 6 mmol). Remove the ice bath, introduce nitrogen, protect from light, and stir the solution at room temperature for one day. The reacted mixture is poured into ice water and filtered to get precipitate. The precipitate is recrystallized from ethanol to obtain orange compound 4.

Mol. Wt.: 418.0487 ($C_{20}H_{16}C_{12}N_2O_4$)

Yield: 58%

Mp: 248-249° C. (EtOH) (lit.37 mp: 249-250° C.)

HRMS (EI) m/z calcd for $C_{20}H_{16}C_{12}N_2O_4$ $^+$[M+H]$^+$: 418.0487. Found: 418.0487.

$^1$H-NMR (300 MHz, CDCl$_3$) δ (ppm):
3.06 (t, J=6.6 Hz, 4H, —CH$_2$—), 3.97 (t, J=6.6 Hz, 4H, —CH$_2$—), 7.80 (t, J=8.1 Hz, 2H, Ar—H$_{3,6}$), 8.08 (dd, J=7.8 Hz, 1.2 Hz, 2H, Ar—H$_{4,5}$), 9.17 (dd, J=8.7 Hz, 1.2 Hz, 2H, Ar—H$_{2,7}$), 12.17 (s, 2H, Ar—NH—)

1,8-Bis[3-(diethylamino) propionamido]anthraquinone (4a)

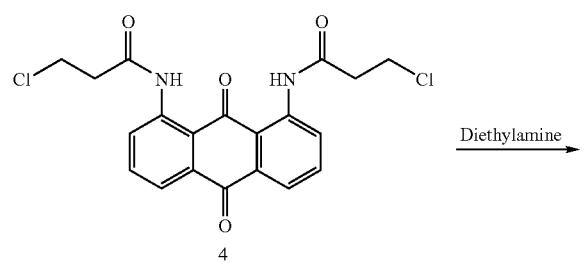

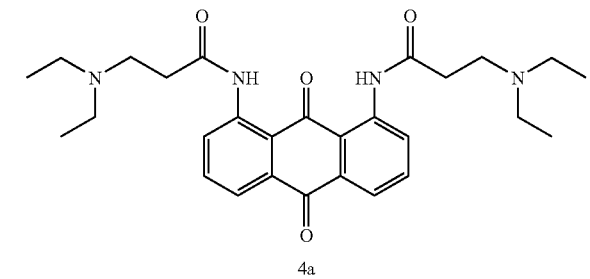

Add 1,8-Bis(3-chloropropionamido)anthraquinone (compound 4, 0.42 g, 1.0 mmol) with pyridine (0.5 ml) and diethylamine (0.6 ml, 6 mmole), dissolved in 20 ml dehydrated THF. The mixture is reacted in a mini-reactor. The reaction temperature is 70-80° C. in an oil bath and the reaction time is 6 hours. The reacted mixture is poured into 50 ml ice water, extracted with ethyl acetate and recrystallized from ethanol to get yellow orange compound 4a.

Mol. Wt.: 492.2737 ($C_{28}H_{36}N_4O_4$)

Yield: 72%

Mp: 166-167° C. (EtOH) (lit.37 mp: 175-176° C.)

IR (KBr) cm-1: 3240 (NH), 2969 (NH), 1699 (CO), 1625 (CO)

HRMS (EI) m/z calcd for $C_{28}H_{36}N_4O_4$ $^+$[M+H]$^+$: 492.2737. Found: 492.2747.

$^1$H-NMR (300 MHz, CDCl3) δ (ppm):
1.05 (t, J=7.2 Hz, 12H, —CH3), 2.60 (q, J=7.2 Hz, 8H, —CH2-), 2.63 (t, J
=7.2 Hz, 4H, —CH2-), 2.92 (t, J=7.2 Hz, 4H, —CH2-), 7.66 (t, J=7.8 Hz, 2H, Ar—H3,6), 7.92 (dd, J=7.2 Hz, 1.2 Hz, 2H, Ar—H4,5), 9.04 (dd, J=8.4 Hz, 1.2 Hz, 2H, Ar—H2,7), 12.01 (s, 2H, Ar—NH—)

13C-NMR (300 MHz, CDCl$_3$) δ (ppm):
11.12, 36.46, 46.40, 48.08, 117.99 (C8a, 9a), 121.77 (C2, 7), 126.35 (C4, 5), 132.83 (C3, 6), 135.18 (C4a, 5a), 141.49 (C1, 8), 171.40 (NCO), 181.79 (C10O), 190.71 (C9O)

1,8-Bis[3-(isobutylamino)propionamido]anthraquinone(4b)

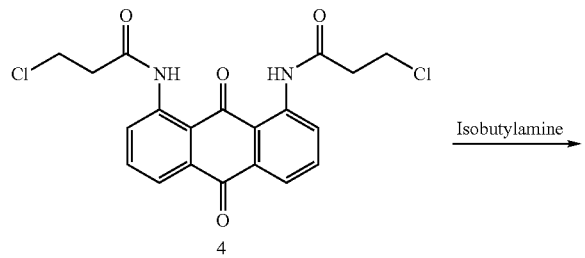

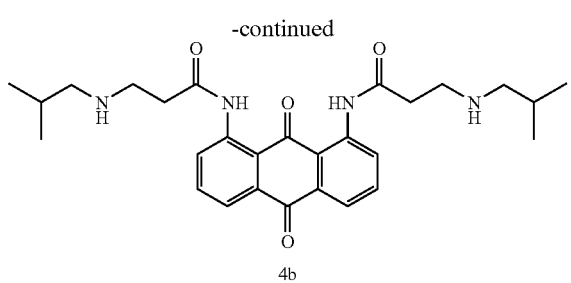

Add 1,8-Bis(3-chloropropionamido)anthraquinone (compound 4, 0.42 g, 1.0 mmol) with pyridine (0.5 ml) and isobutylamine (0.6 ml, 6 mmole), dissolved in 20 ml dehydrated THF. The mixture is reacted in a mini-reactor. The reaction temperature is 70-80° C. in an oil bath and the reaction time is 6 hours. The reacted mixture is poured into 50 ml ice water, extracted with ethyl acetate and recrystallized from ethanol to get compound 4b.

Mol. Wt.: 492.2737 (C28H36N4O4)
Yield: 54%
Mp: 224-225° C. (EtOH)
IR (KBr) cm-1: 3249 (NH), 2954 (NH), 1690 (CO), 1627 (CO)
HRMS (EI) m/z calcd for C28H36N4O4+[M+H]+: 492.2737. Found: 492.2728.

1H-NMR (300 MHz, CDCl$_3$) δ (ppm):
0.93 (d J=6.6 Hz, 12H, CH3), 1.74-1.81 (m, 2H, CH), 2.51 (d, J=6.6 Hz, 4H, CH2), 2.78 (t, J=6.3 Hz, 4H, —CH2-), 3.06 (t, J=6.3 Hz, 4H, —CH2-), 7.77 (t, J=8.1 Hz, 2H, Ar—H3,6), 8.05 (dd, J=7.8 Hz, 1.2 Hz, 2 H, Ar—H4,5), 9.15 (dd, J=8.4 Hz, 1.2 Hz, 2H, Ar—H2,7), 12.13 (s, 2H, Ar—NH—)

$^{13}$C-NMR (300 MHz, CDCl$_3$) δ (ppm):
19.72, 27.28, 38.00, 44.54, 57.12, 117.20 (C8a, 9a), 121.36 (C2, 7), 125.74 (C4, 5), 132.19 (C3, 6), 134.91 (C4a, 5a), 141.11 (C1, 8), 170.92 (NCO), 180.98 (C10O), 190.10 (C9O)

1,8-Bis[3-(3,5-difluorobenzylamino)propionamido]anthraquinone (4c)

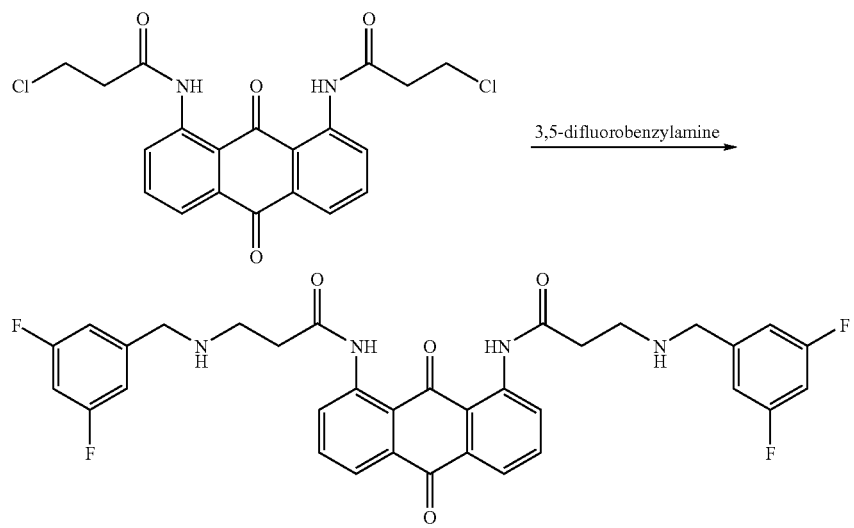

Add 1,8-Bis(3-chloropropionamido)anthraquinone (compound 4, 0.42 g, 1.0 mmol) with pyridine (0.5 ml) and 3,5-difluorobenzylamine (0.7 ml, 6 mmole), dissolved in 20 ml dehydrated THF. The mixture is reacted in a mini-reactor. The reaction temperature is 70-80° C. in an oil bath and the reaction time is 6 hours. The reacted mixture is poured into 50 ml ice water, extracted with ethyl acetate and recrystallized from ethanol to get compound 4c.

Mol. Wt.: 632.2047 (C$_{34}$H$_{28}$F$_4$N$_4$O$_4$)
Yield: 40%
Mp: 190-191° C. (EtOH)
IR (KBr) cm-1: 3246 (NH), 2909 (NH), 1702 (CO), 1626 (CO)
HRMS (EI) m/z calcd for C34H28F4N4O4+[M+H]+: 632.2047. Found: 632.2044.

$^1$H-NMR (300 MHz, CDCl$_3$) δ (ppm):
2.76 (t, J=6.3 Hz, 4H, —CH2-), 3.05 (t, J=6.3 Hz, 4H, —CH2-), 3.86 (s, 4H, —CH2-), 6.62 (tt, J=9.0 Hz, 2.1 Hz, 2H, Ar'-H4), 6.89 (dd, J=8.1Hz, 1.8 Hz, 4H, Ar'—H2,6), 7.78 (t, J=8.1 Hz, 2H, Ar—H3,6), 8.06 (dd, J=7.8 Hz, 1.2 Hz, 2H, Ar—H4,5), 9.15 (dd, J=8.4 Hz, 1.2 Hz, 2H, Ar—H2,7), 12.09 (s, 2H, Ar—NH—)

13C-NMR (300 MHz, CDCl$_3$) δ (ppm):
38.40, 44.15, 52.41, 101.68, 109.76, 110.08, 117.76 (C8a, 9a), 121.88 (C2, 7), 126.10 (C4, 5), 132.83 (C3, 6), 135.36 (C4a, 5a), 141.46 (C1, 8), 144.18, 161.16, 164.29, 170.91 (NCO), 181.53 (C10O), 191.00 (C9O)

1,8-Bis[2-(N-Boc-ethanediamino)propionamido]anthraquinone (4d)

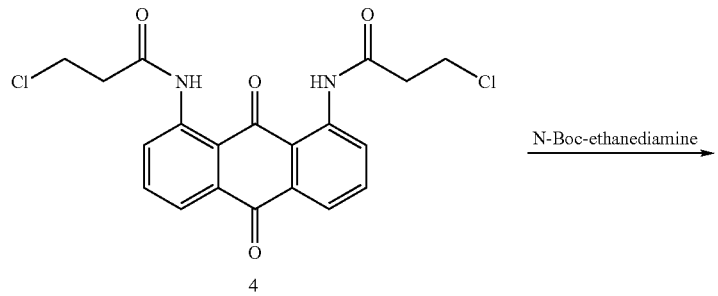

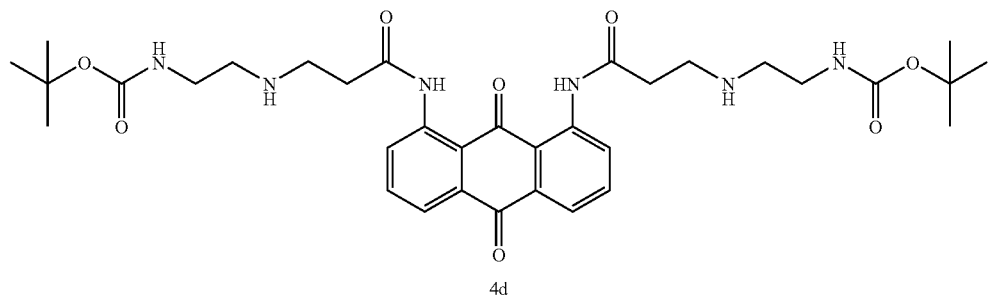

Add 1,8-Bis(3-chloropropionamido)anthraquinone (compound 4, 0.42 g, 1.0 mmol) with pyridine (0.5 ml) and N-Boc-ethanediamine (0.9 ml, 6 mmole), dissolved in 20 ml dehydrated THF. The mixture is reacted in a mini-reactor. The reaction temperature is 70-80° C. in an oil bath and the reaction time is 6 hours. The reacted mixture is poured into 50 ml ice water, extracted with ethyl acetate and recrystallized from ethanol to get compound 4d.

Mol. Wt.: 666.3377 (C34H46N6O8)
Yield: 30%
Mp: 101-102° C. (EtOH)
IR (KBr) cm-1: 3359 (NH), 2967 (NH), 1692 (CO)
FAB-MS m/z (%): 666 (M+,2.17), 668 ([M+2]+,100)
1H-NMR (300 MHz, CDCl$_3$) δ (ppm):
1.39 (s, 18H, CH3), 2.76 (t, J=6.3 Hz, 4H, —CH2-), 2.83 (t, J=5.7 Hz, 4 H, —CH2-), 3.08 (t, J=6.3 Hz, 4H, —CH2-), 3.28 (q, J=5.7 Hz, 4H, —CH2-), 5.18 (s, 2H, NH), 7.77 (t, J=8.4 Hz, 2H, Ar—H3,6), 8.05 (dd, J=7.5 Hz, 1.2 Hz, 2H, Ar—H4, 5), 9.14 (dd, J=8.7 Hz, 1.2 Hz, 2H, Ar—H2,7), 12.13 (s, 2H, Ar—NH—)

13C-NMR (300 MHz, CDCl$_3$) δ (ppm):
27.93, 40.11, 49.33, 53.32, 78.75, 118.39 (C8a, 9a), 121.77 (C2, 7), 126.07 (C4, 5), 132.77 (C3, 6), 134.90 (C4a, 5a), 140.85 (C1, 8), 155.97 (CCO), 171.92 (NCO), 181.90 (C10O), 189.71 (C9O)

1,8-Bis[2-(dimethylethanediamino)propionamido]anthraquinone (4e)

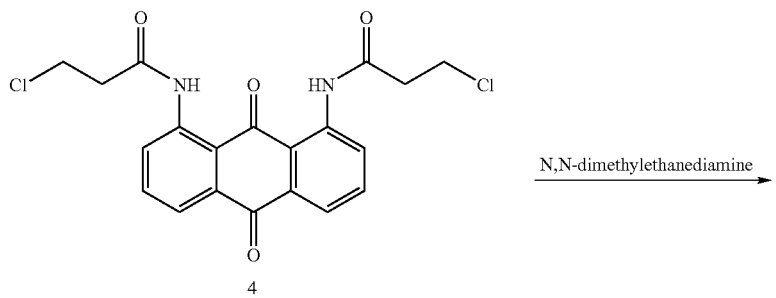

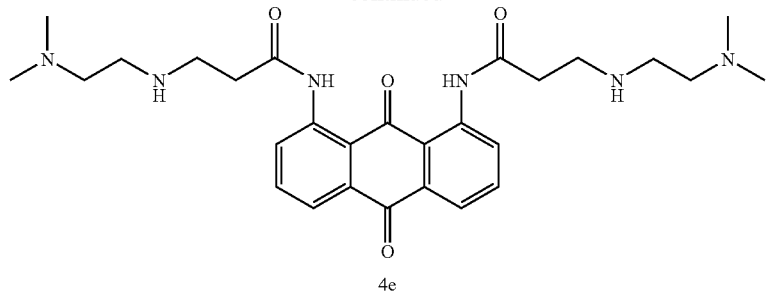

4e

Add 1,8-Bis(3-chloropropionamido)anthraquinone (compound 4, 0.42 g, 1.0 mmol) with pyridine (0.5 ml) and N,N-dimethylethanediamine (0.7 ml, 6 mmole), dissolved in 20 ml dehydrated THF. The mixture is reacted in a mini-reactor. The reaction temperature is 70-80° C. in an oil bath and the reaction time is 6 hours. The reacted mixture is poured into 50 ml ice water, extracted with ethyl acetate and recrystallized from ethanol to get compound 4e.

Mol. Wt.: 522.2955 (C28H38N6O4)
Yield: 18%
Mp: 100-102° C. (EtOH)
IR (KBr) cm-1: 3248 (NH), 2938 (NH), 1690 (CO)
HRMS (EI) m/z calcd for C28H38N6O4+[M+H]+: 522.2955. Found: 522.2964.
1H-NMR (300 MHz, CDCl3) δ (ppm):
2.22 (s, 8H, —CH3), 2.44 (t, J=6.0 Hz, 4H, —CH2-), 2.77 (t, J=6.3 Hz, 4 H, —CH2-), 2.80 (t, J=6.0 Hz, 4H, —CH2-), 3.09 (t, J=6.3 Hz, 4H, —CH2-), 7.76 (t, J=8.1 Hz, 2H, Ar—H3,6), 8.04 (dd, J=7.8 Hz, 1.5 Hz, 2H, Ar—H4,5), 9.14 (dd, J=8.7 Hz, 1.5 Hz, 2H, Ar—H2,7), 12.13 (s, 2H, Ar—NH—)
13C-NMR (300 MHz, CDCl3) δ (ppm):
38.60, 44.87, 45.29, 46.83, 58.57, 118.03 (C8a, 9a), 121.82 (C2, 7), 126.30 (C4, 5), 132.91 (C3, 6), 135.23 (C4a, 5a), 141.53 (C1, 8), 171.12 (NCO), 181.77 (C10O), 190.92 (C9O)

1,8-Bis[2-(dimethylamino)propionamido]anthraquinone (4f)

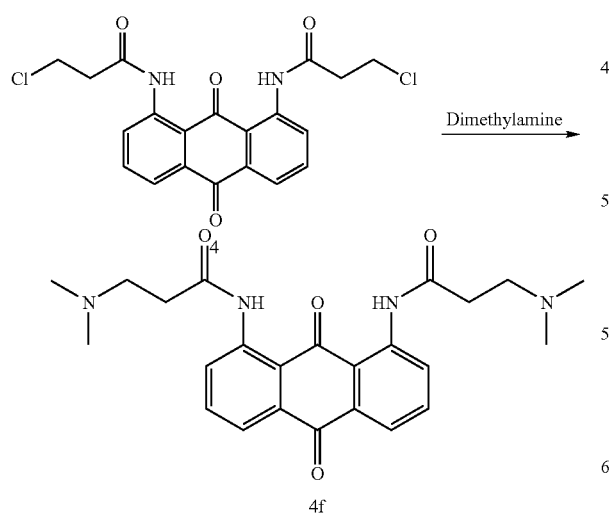

4f

Add 1,8-Bis(3-chloropropionamido)anthraquinone (compound 4, 0.42 g, 1.0 mmol) with pyridine (0.5 ml) and dimethylamine (0.6 ml, 6 mmole), dissolved in 20 ml dehydrated THF. The mixture is reacted in a mini-reactor. The reaction temperature is 70-80° C. in an oil bath and the reaction time is 6 hours. The reacted mixture is poured into 50 ml ice water, extracted with ethyl acetate and recrystallized from ethanol to get compound 4f.

Mol. Wt.: 436.2111 (C24H28N4O4)
Yield: 74%
Mp: 116-117° C. (EtOH) (lit.37 mp: 126° C.)
IR (KBr) cm-1: 3251 (NH), 2949 (NH), 1697 (CO), 1626 (CO)
HRMS (EI) m/z calcd for C24H28N4O4+[M+H]+: 436.2111. Found: 436.2111.
1H-NMR (300 MHz, CDCl3) δ (ppm):
2.36 (s, 12H, —CH3), 2.71 (t, J=6.3 Hz, 4H, —CH2-), 2.80 (t, J=6.3 Hz, 4H, —CH2-), 7.76 (t, J=8.1 Hz, 2H, Ar—H3,6), 8.05 (dd, J=7.5 Hz, 1.2 Hz, 2H, Ar—H4,5), 9.14 (dd, J=8.4 Hz, 1.2 Hz, 2H, Ar—H2,7), 12.22 (s, 2H, Ar—NH—)
13C-NMR (300 MHz, CDCl3) δ (ppm):
36.29, 44.66, 54.34, 117.89 (C8a, 9a), 121.66 (C2, 7), 126.33 (C4, 5), 132.61 (C3, 6), 135.01 (C4a, 5a), 141.29 (C1, 8), 170.84 (NCO), 181.52 (C10O), 190.34 (C9O)

1,8-Bis[2-(dipropylamino)propionamido]anthraquinone (4g)

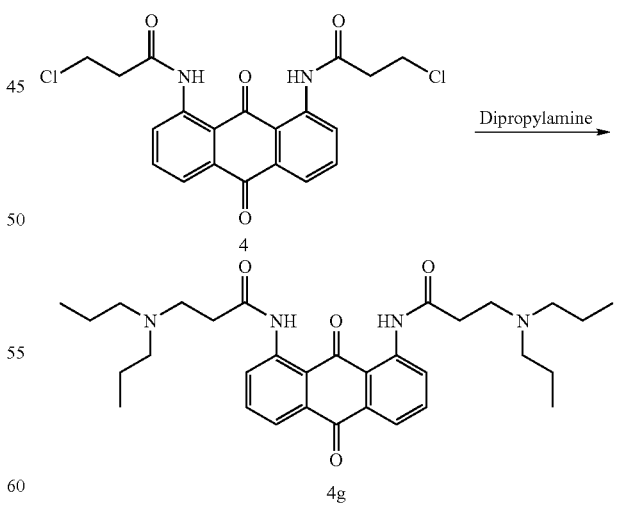

4

4g

Add 1,8-Bis(3-chloropropionamido)anthraquinone (compound 4, 0.42 g, 1.0 mmol) with pyridine (0.5 ml) and dipropylamine (0.7 ml, 6 mmole), dissolved in 20 ml dehydrated THF. The mixture is reacted in a mini-reactor. The reaction temperature is 70-80° C. in an oil bath and the reaction time is 6 hours. The reacted mixture is poured into 50 ml ice water, extracted with ethyl acetate and recrystallized from ethanol to get compound 4g.

Mol. Wt.: 548.3363 (C32H44N4O4)

Yield: 79%

Mp: 129-130° C. (EtOH)

IR (KBr) cm-1: 3234 (NH), 2959 (NH), 1698 (CO), 1626 (CO)

HRMS (EI) m/z calcd for C32H44N4O4+[M+H]+: 548.3363. Found: 548.3374.

1H-NMR (300 MHz, CDCl$_3$) δ (ppm):

0.87 (t, J=7.5 Hz, 12H, —CH3), 1.46-1.53 (m, 8H, —CH2-), 2.46 (t, J=5.4 Hz, 8H, —CH2-), 2.67 (t, J=6.9 Hz, 4H, —CH2-), 2.96 (t, J=6.9 Hz, 4H, —CH2-), 7.76 (t, J=8.1 Hz, 2H, Ar—H3,6), 8.04 (d, J=7.5 Hz, 2H, Ar—H4,5), 9.15 (d, J=8.7 Hz, 2H, Ar—H2,7), 12.11 (s, 2H, Ar—NH—)

13C-NMR 11.21, 19.66, 36.72, 49.46, 55.61, 117.79 (C8a, 9a), 121.68 (C2, 7), 126.19 (C4, 5), 132.77 (C3, 6), 135.18 (C4a, 5a), 141.58 (C1, 8), 171.43 (NCO), 181.69 (C10O), 190.78 (C9O)

1,8-Bis[2-(methylamino)propionamido]anthraquinone (4h)

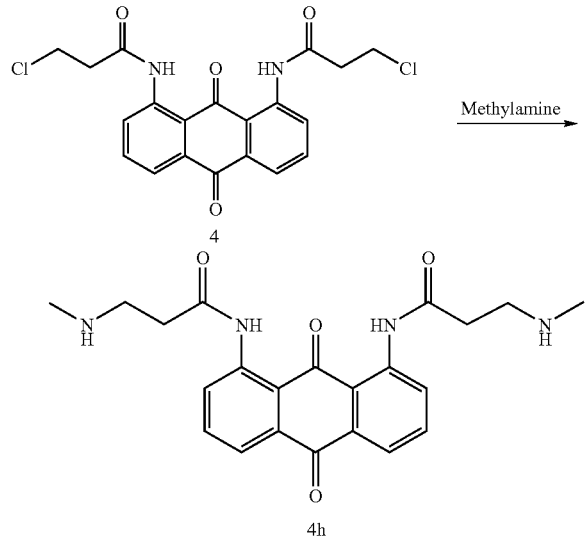

4h

Add 1,8-Bis(3-chloropropionamido)anthraquinone (compound 4, 0.42 g, 1.0 mmol) with pyridine (0.5 ml) and methylamine (0.4 ml, 6 mmole), dissolved in 20 ml dehydrated THF. The mixture is reacted in a mini-reactor. The reaction temperature is 70-80° C. in an oil bath and the reaction time is 6 hours. The reacted mixture is poured into 50 ml ice water, extracted with ethyl acetate and recrystallized from ethanol to get compound 4h.

Mol. Wt.: 408.1798 (C22H24N4O4)

Yield: 32%

Mp: 233-234° C. (EtOH)

IR (KBr) cm-1: 3249 (NH), 2967 (NH), 1690 (CO), 1624 (CO)

HRMS (EI) m/z calcd for C22H24N4O4+[M+H]+: 408.1798. Found: 408.1783.

1H-NMR (300 MHz, CDCl$_3$) δ (ppm):

2.53 (s, 6H, —CH3), 2.78 (t, J=6.3 Hz, 4H, —CH2-), 3.05 (t, J=6.3 Hz, 4 H, —CH2-), 7.77 (t, J=8.1 Hz, 2H, Ar—H3,6), 8.05 (dd, J=7.5 Hz, 1.2 Hz, 2H, Ar—H4,5), 9.14 (dd, J=8.4 Hz, 1.2 Hz, 2H, Ar—H2,7), 12.17 (s, 2H, Ar—NH—)

13C-NMR (300 MHz, CDCl$_3$) δ (ppm):

35.65, 38.03, 46.82, 118.06 (C8a, 9a), 121.99 (C2, 7), 126.33 (C4, 5), 132.90 (C3, 6), 135.35 (C4a, 5a), 141.43 (C1, 8), 171.19 (NCO), 181.83 (C10O), 190.97 (C9O)

1,8-Bis[2-(isopropylamino)propionamido]anthraquinone (4i)

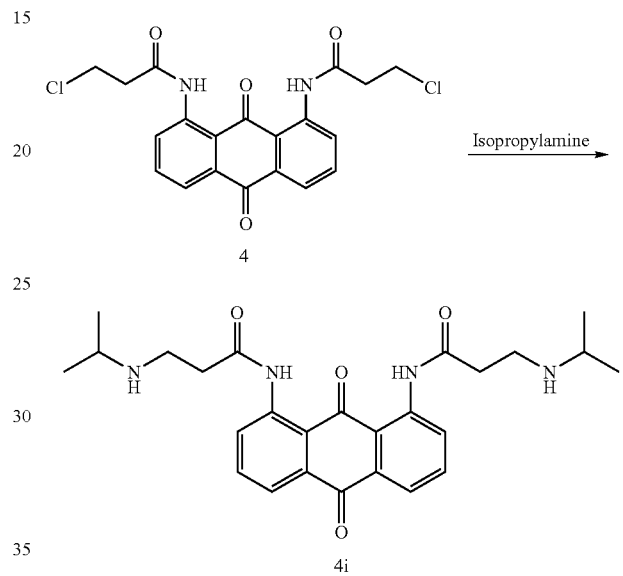

Add 1,8-Bis(3-chloropropionamido)anthraquinone (compound 4, 0.42 g, 1.0 mmol) with pyridine (0.5 ml) and isopropylamine (0.6 ml, 6 mmole), dissolved in 20 ml dehydrated THF. The mixture is reacted in a mini-reactor. The reaction temperature is 70-80° C. in an oil bath and the reaction time is 6 hours. The reacted mixture is poured into 50 ml ice water, extracted with ethyl acetate and recrystallized from ethanol to get compound 4i.

Mol. Wt.: 464.2424 (C26H32N4O4)

Yield: 58%

Mp: 105-106° C. (EtOH)

IR (KBr) cm-1: 3249 (NH), 2967 (NH), 1689 (CO), 1624 (CO)

HRMS (EI) m/z calcd for C26H32N4O4+[M+H]+: 464.2424. Found: 464.2425.

1H-NMR (300 MHz, CDCl3) δ (ppm):

1.11 (d, J=6.3 Hz, 12H, —CH3), 2.78 (t, J=6.3 Hz, 4H, —CH2-), 2.88-2.92 (m, 2H, —CH), 3.06 (t, J=6.3 Hz, 4H, —CH2-), 7.77 (t, J=7.8 Hz, 2H, Ar—H3,6), 8.05 (dd, J=7.8 Hz, 1.5 Hz, 2H, Ar—H4,5), 9.14 (dd, J=8.7 Hz, 1.5 Hz, 2H, Ar—H2,7), 12.14 (s, 2H, Ar—NH—)

13C-NMR (300 MHz, CDCl$_3$) δ (ppm):

22.20, 38.61, 42.12, 48.04, 117.59 (C8a, 9a), 121.65 (C2, 7), 126.04 (C4, 5), 132.59 (C3, 6), 135.15 (C4a, 5a), 141.36 (C1, 8), 171.11 (NCO), 181.37 (C10O), 190.55 (C9O)

1,8-Bis[2-(dimethylpropanediamino)propionamido]anthraquinone(4j)

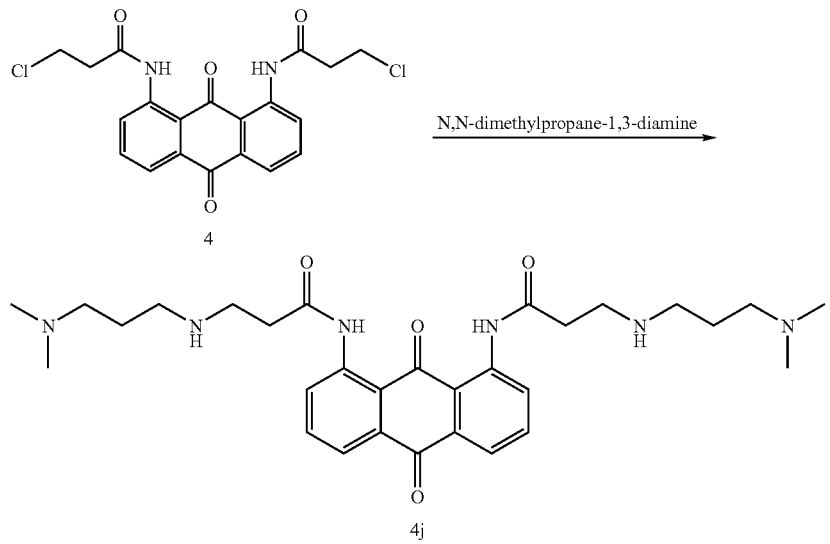

Add 1,8-Bis(3-chloropropionamido)anthraquinone (compound 4, 0.42 g, 1.0 mmol) with pyridine (0.5 ml) and N,N-dimethylpropane-1,3-diamine (0.7 ml, 6 mmole), dissolved in 20 ml dehydrated THF. The mixture is reacted in a mini-reactor. The reaction temperature is 70-80° C. in an oil bath and the reaction time is 6 hours. The reacted mixture is poured into 50 ml ice water, extracted with ethyl acetate and recrystallized from ethanol to get compound 4j.

Mol. Wt.: 550.3268 (C30H42N6O4)
Yield: 44%
Mp: 107-108° C. (EtOH)
IR (KBr) cm-1: 3254 (NH), 2928 (NH), 1688 (CO)
FAB-MS m/z (%): 552 ([M+2]+, 100)
1H-NMR (300 MHz, CDCl3) δ (ppm):
1.67-1.74 (m, 4H, —CH2-), 2.19 (s, 12H, —CH3), 2.32 (t, J=7.2 Hz, 4H, —CH2-), 2.73 (t, J=6.9 Hz, 4H, —CH2-), 2.79 (t, J=6.3 Hz, 4H, —CH2-), 3.06 (t, J=6.3 Hz, 4H, —CH2-), 7.76 (t, J=7.8 Hz, 2H, Ar—H3,6), 8.04 (dd, J=7.5 Hz, 1.2 Hz, 2H, Ar—H4,5), 9.14 (d, J=8.4 Hz, 2H, Ar—H2,7), 12.12 (s, 2H, Ar—NH—)

13C-NMR (300 MHz, CDCl$_3$) δ (ppm):
27.33, 38.41, 44.79, 47.70, 57.33, 117.93 (C8a, 9a), 121.84 (C2, 7), 126.24 (C4, 5), 132.85 (C3, 6), 135.26 (C4a, 5a), 141.48 (C1, 8), 171.19 (NCO), 181.73 (C10O), 190.88 (C9O)

1,8-Bis[2-(N-ethylmethylamino)propionamido]anthraquinone (4k)

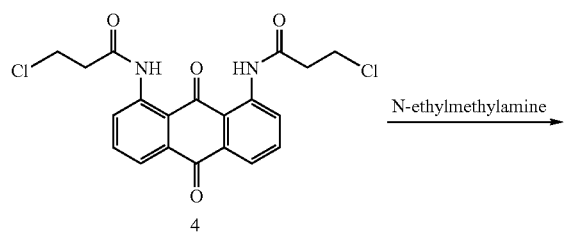

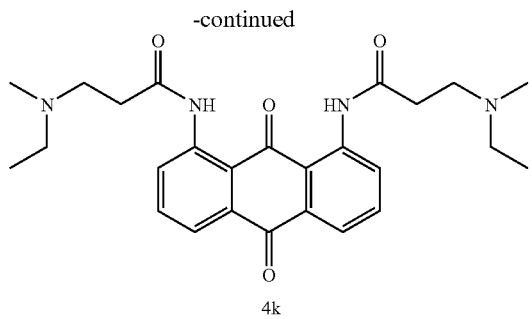

Add 1,8-Bis(3-chloropropionamido)anthraquinone (compound 4, 0.42 g, 1.0 mmol) with pyridine (0.5 ml) and N-ethylmethylamine (0.6 ml, 6 mmole), dissolved in 20 ml dehydrated THF. The mixture is reacted in a mini-reactor. The reaction temperature is 70-80° C. in an oil bath and the reaction time is 6 hours. The reacted mixture is poured into 50 ml ice water, extracted with ethyl acetate and recrystallized from ethanol to get compound 4k.

Mol. Wt.: 464.2424 (C$_{26}$H$_{32}$N$_4$O$_4$)
Yield: 79%
Mp: 129-130° C. (EtOH)
IR (KBr) cm-1: 3233 (NH), 2969 (NH), 1700 (CO), 1624 (CO)
HRMS (EI) m/z calcd for C26H32N4O4+[M+H]+: 464.2424. Found: 464.2419.
1H-NMR (300 MHz, CDCl$_3$) δ (ppm):
1.09 (t, J=7.2 Hz, 6H, —CH3), 2.33 (s, 4H, —CH3), 2.54 (q, J=7.2 Hz, 4 H, —CH2-), 2.70 (t, J=6.9 Hz, 4H, —CH2-), 2.86 (t, J=6.6 Hz, 4H, —CH2-), 7.72 (t, J=8.4 Hz, 2H, Ar—H3,6), 8.00 (dd, J=7.5 Hz, 1.2 Hz, 2 H, Ar—H4,5), 9.09 (dd, J=8.7 Hz, 1.2 Hz, 2H, Ar—H2,7), 12.14 (s, 2H, Ar—NH—)

13C-NMR (300 MHz, CDCl$_3$) δ (ppm):
11.41, 36.20, 40.80, 50.74, 51.93, 117.89 (C8a, 9a), 121.70 (C2, 7), 126.33 (C4, 5), 132.67 (C3, 6), 135.08 (C4a, 5a), 141.36 (C1, 8), 171.07 (NCO), 181.60 (C10O), 190.45 (C9O)

Results of Pharmacological Tests
MTT Colorimetric Assay

MTT (tetrazole) assay used to determine tumor viability is based on measurement of the activity of dehydrogenase to determine cell growth conditions. In live cells, dehydrogenase in active mitochondria converts yellow MTT [3-(4,5-dimethylthiazol-2-yl)-2,5-diphenyltetra zolium bromide] into purple formazan on the reductive cleavage of its tetrazolium ring. The formazan crystal is examined under the microscope. While the mitochondria in dead cells are without active dehydrogenase, no crystal is generated and the color remains yellow. After adding MTT into cell cultures and reacting for 2 hours, the amount of generated formazan precipitate is proportional to total amount of dehydrogenase. Removing the culture medium, add DMSO to dissolve the purple formazan precipitate. Then measure the absorbance of the precipitate by is measured by the spectrophotometer at 560/670 nm so as to learn inhibition effect of drugs acted on normal cells and tumor cells.

GBM 8401, GBM 8901 (human brain glioblastoma) and SVG p12 (human brain astroglia)cells line are selected to be used in 96 well petri dishes. Each well is filled into the same amount of cells-about 5000 cells per well. After being cultured for 24 hours and cells anchor/attach, the 96 wells are divided into two groups-an experimental group and a control group containing no samples. The samples are diluted into 10 μg/mL by culture medium. Take 200 μL of each sample and add into the experimental group and the control group is added with 200 μL culture medium without samples. After 46 hours of culture, each well is added with 10 μL MTT solution, incubate cells at 37° C., 5% CO2 for 2 hours.

Then each well is added with 100 μL, dissolving formazan. Shaking for 10 minutes and measure the absorbance at 560/670 nm of the sample by the spectrometer. The data of the experimental group is divided by the data of the control group to get the estimated cell viability.

Screening Results of MTT Assay

Figure 10:
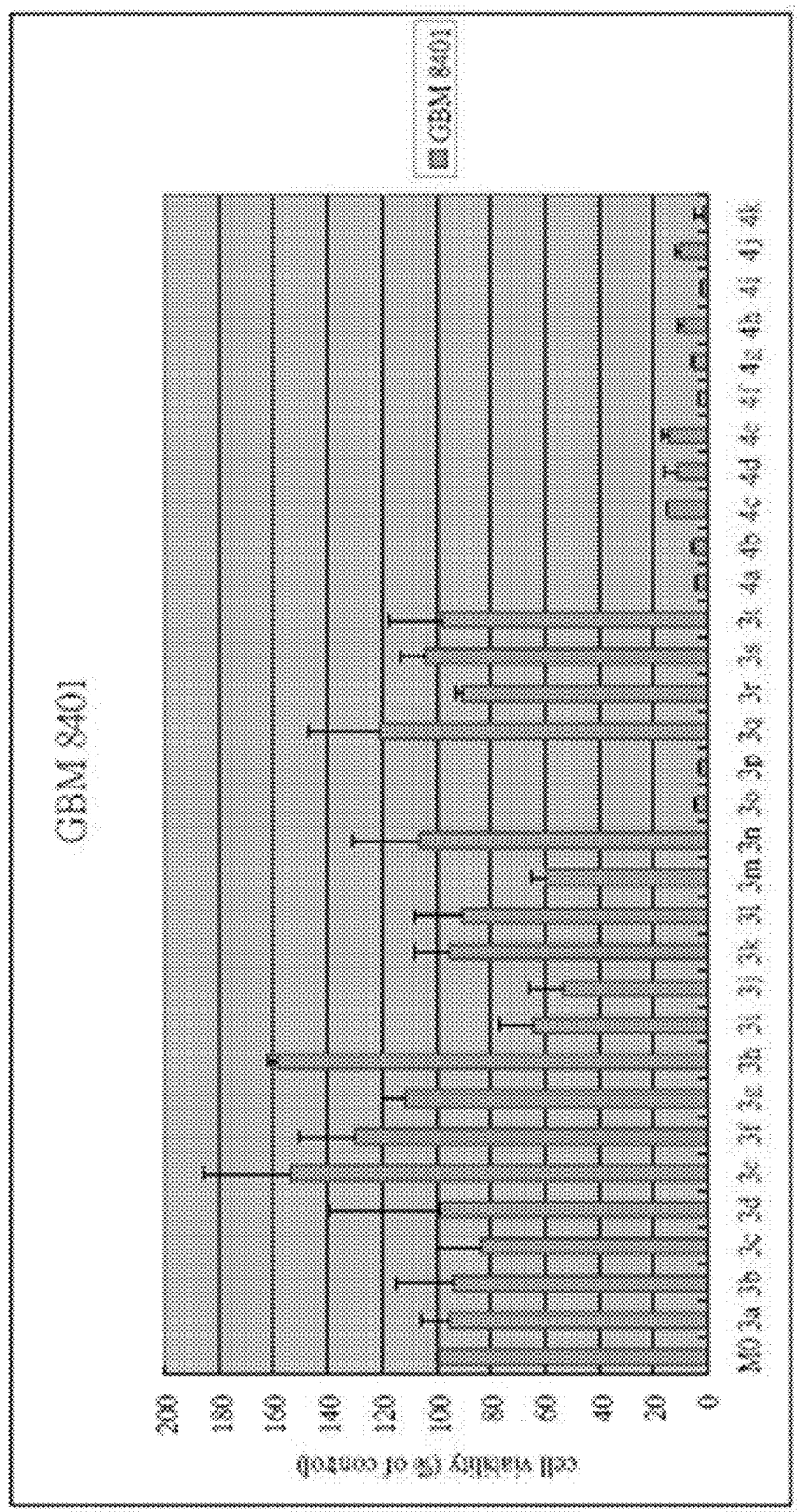
FIG. 10 shows cell viability (%) of GBM 8401 cell line reacted with anti-cancer compounds 3a-4k at a concentration of 10 μM.
Figure 11:
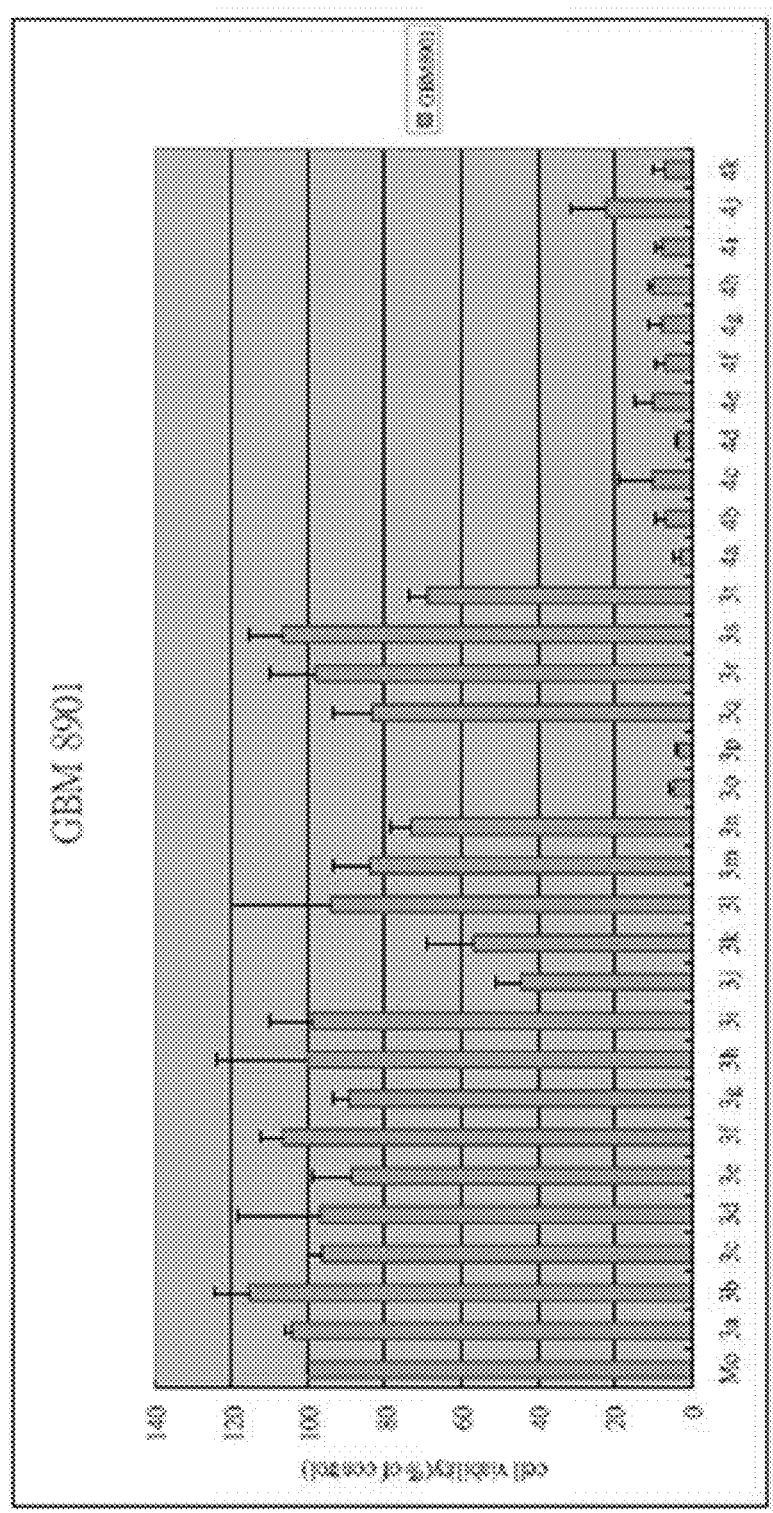
FIG. 11 shows cell viability (%) of GBM 8901 cell line reacted with anti-cancer compounds 3a-4k at a concentration of 10 μM.
Figure 12:
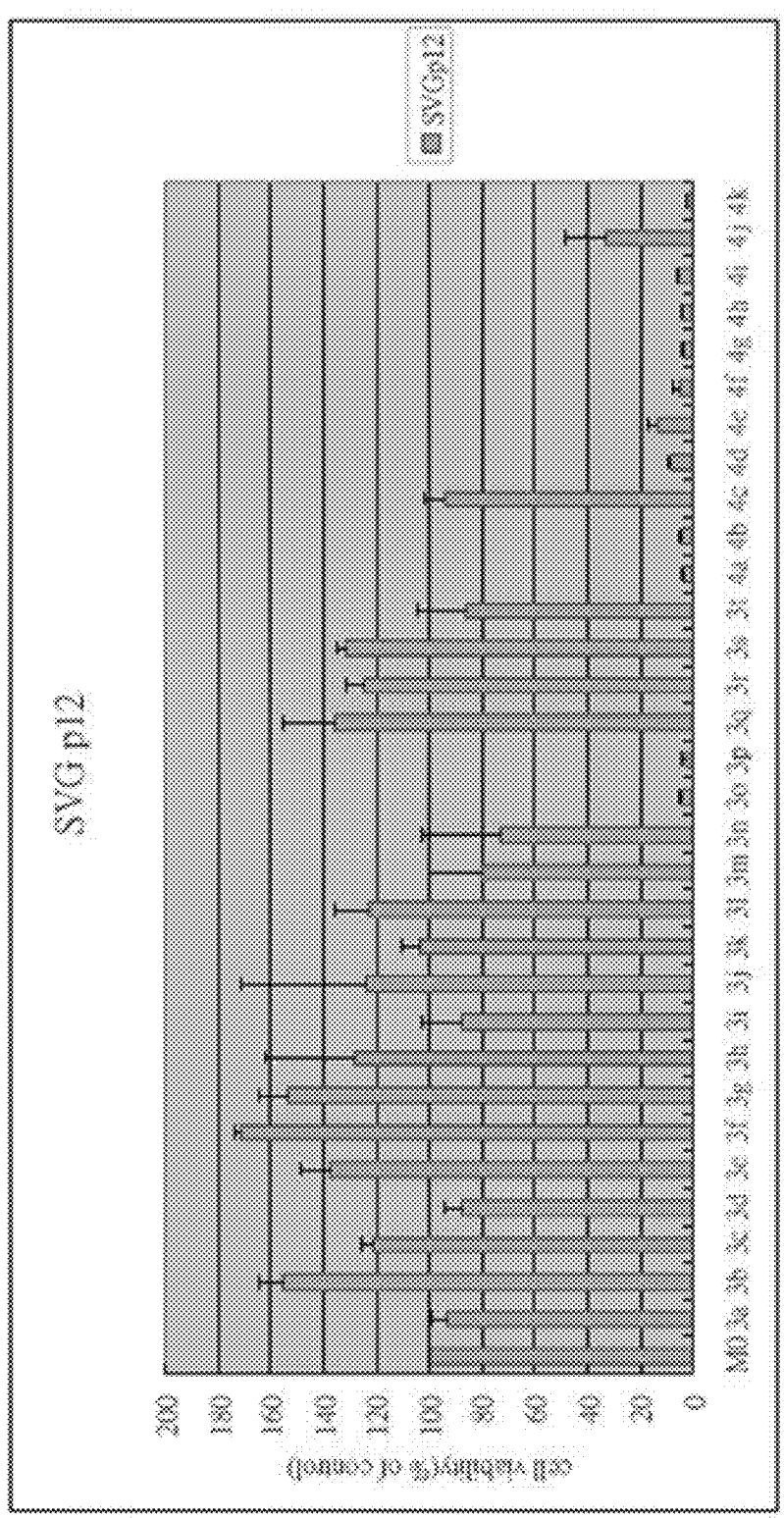
FIG. 12 shows cell viability (%) of SVG p12 cell line reacted with anti-cancer compounds 3a-4k at a concentration of 10 μM.

Screening results of GBM 8401 cell line are shown in FIG. 10, screening results of GBM 8901 cell line are shown in FIG. 11, screening results of SVG p12 cell line are shown in FIG. 12, and screening results of MTT assays are shown in list one.

Three cell lines-GBM 8401, GBM 8901, SVG p12 (normal) are used in cytotoxicity tests of 1,8-bis-substituted amidoanthraquinone. After reacting with the drug for 46 hours, the cells are reacted with certain amount of MTT solution. After 2 hours, DMSO is used to dissolve formazan and O.D. (optical density) at 560/670 nm is measured. Then calculate the radios of the experimental groups (with drugs) to the control groups (without drugs).

In the primary screening, the viability less than 80% is used as screening criterion for discussion. It is found that compounds 3i, 3j, 3m, 3o, 3p, 4a-4k can inhibit proliferation of tumor cells GBM 8401, and compounds 3j, 3k, 3n, 3o, 3p, 3t, 4a-4k inhibit growth of tumor cells GBM 8901. Compared with cytotoxicity tests, the cell viabilities of normal SVG p12 cells treated by the compounds 3i, 3j, 3k, 3m, 3t and 4c are all over 80% and these compounds are most promising drugs within results of this screening.

List one: results of primary screening of compounds 3a-4k evaluated by MTT assay (conc. 10 μM)

| Compd | R | Cell viability (%) | | |
|---|---|---|---|---|
| | | GBM 8401 | GBM 8901 | SVG p12 |
| 3a | $NHCH_2CO_2CH_3$ | 95 ± 10 | 104 ± 2 | 93 ± 6 |
| 3b | $NHCH(CH_2CH_2SCH_3)CO_2CH_3$ | 94 ± 20 | 115 ± 9 | 156 ± 9 |
| 3c | $N(CH_2CH_2CH_2CH_2)CO_2CH_3$ | 83 ± 15 | 96 ± 3 | 121 ± 5 |
| 3d | $NHCH(CH(CH_3)_2)CO_2CH_3$ | 99 ± 40 | 97 ± 22 | 87 ± 7 |
| 3e | $(D)-NHCH(CH(CH_3)_2)CO_2CH_3$ | 153 ± 32 | 88 ± 10 | 138 ± 10 |
| 3f | $N(CH_3)CH_2CO_2CH_3$ | 130 ± 20 | 107 ± 5 | 172 ± 2 |
| 3g | $NHCH(CH_2CH(CH_3)_2)CO_2CH_3$ | 111 ± 8 | 89 ± 4 | 153 ± 11 |
| 3h | $NHCH(CH_3)CO_2CH_3$ | 158 ± 3 | 100 ± 24 | 128 ± 34 |
| 3i | $(D)-NHCH(CH_3)CO_2CH_3$ | 64 ± 13 | 99 ± 11 | 87 ± 16 |
| 3j | $NHCH(C_6H_5)CO_2CH_3$ | 53 ± 12 | 45 ± 7 | 124 ± 47 |
| 3k | $NHCH_2CH(CH_3)_2$ | 95 ± 12 | 57 ± 16 | 103 ± 7 |
| 3l | $N(CH_2CH_3)_2$ | 91 ± 17 | 94 ± 26 | 123 ± 13 |
| 3m | $N(CH_3)_2$ | 60 ± 5 | 84 ± 9 | 80 ± 20 |
| 3n | $N(CH_2CH_2CH_3)_2$ | 106 ± 24 | 73 ± 5 | 73 ± 30 |
| 3o | $NHCH(CH_3)_2$ | 4 ± 1 | 5 ± 1 | 4 ± 1 |
| 3p | $NHCH_2CH_3$ | 2 ± 1 | 4 ± 1 | 3 ± 1 |
| 3q | $3-(CF_3)C_6H_4CH_2NH$ | 120 ± 26 | 83 ± 10 | 135 ± 20 |
| 3r | $N(CH_3)CH_2CH_3$ | 90 ± 2 | 98 ± 12 | 125 ± 7 |
| 3s | $N(CH_3)CH_2CH_2CH_3$ | 103 ± 9 | 107 ± 9 | 132 ± 3 |
| 3t | $NHCH(CH_2OCH(CH_3)_3)CO_2CH_3$ | 98 ± 19 | 69 ± 4 | 86 ± 18 |
| 4a | $N(CH_2CH_3)_2$ | 4 ± 0 | 3 ± 2 | 3 ± 0 |
| 4b | $NHCH_2CH(CH_3)_2$ | 4 ± 1 | 7 ± 3 | 4 ± 0 |
| 4c | $3,5-F_2C_6H_3CH_2NH$ | 14 ± 1 | 11 ± 9 | 94 ± 8 |
| 4d | $NHCH_2CH_2NHBoc$ | 10 ± 5 | 4 ± 0 | 8 ± 1 |
| 4e | $NHCH_2CH_2N(CH_3)_2$ | 14 ± 2 | 10 ± 5 | 13 ± 3 |
| 4f | $N(CH_3)_2$ | 3 ± 0 | 7 ± 3 | 4 ± 3 |
| 4g | $N(CH_2CH_2CH_3)_2$ | 5 ± 1 | 8 ± 2 | 4 ± 0 |
| 4h | $NHCH_3$ | 9 ± 2 | 10 ± 1 | 4 ± 0 |
| 4i | $NHCH(CH_3)_2$ | 2 ± 1 | 8 ± 2 | 5 ± 1 |
| 4j | $NHCH_2CH2CH_2N(CH_3)_2$ | 9 ± 2 | 22 ± 9 | 33 ± 16 |
| 4k | $N(CH_3)CH_2CH_3$ | 1 ± 3 | 7 ± 3 | 2 ± 0 |

Telomeric Repeat Amplification Protocol (TRAP)

Telomeric repeat amplification protocol (TRAP) is a common method used to detect measures enzymatic activity of telomerase. The method includes two stages-the first stage: telomerase-mediated addition of oligonucleotide with telomere sequence (TTAGGG repeats) (SEQ ID NO: 2) (TSG4 primer: 5' GGG ATT GGG ATT GGG ATT GGG TT 3') (SEQ ID NO: 5) and the second stage-PCR (polymerase chain reaction) used to amplify the extended telomerase products (CX primer: 5'CCCTTA CCCTTA CCCTTA CCCTAA3') (SEQ ID NO: 6). When the compounds have activity that inhibits telomrease, the telomere sequence is unable to be replicated. In an internal control group of the TRAP array, an oligonucleotide with 36 bases (TSNT: 5' AAT CCG TCG AGC AGA GTT AAA AGG CCG AGA AGC GAT 3') (SEQ ID NO: 7) is added. The oligonucleotide uses TS primer together with the PCR amplification of TRAP and a reverse primer for PCR is added so that the oligonucleotide can be amplified. The control group is for monitoring activity of Taq polymerase.

The assay is performed as follows: add 360 nM CX primer, 185 nM NT primer, and 400 aM oligonucleotide TSNT necessary for the reaction into a bottom of a test tube. PERKIN ELMER AmpliWax PCR Gem 50 is also put into the test tube. In a 9700 Perkin-Elmer Thermocycler, PCR is run on the condition: 10 mins at 90° C., 3 mins at 72° C., 1 min at 50° C., and 1 min at 20° C. Until the temperature cooling down to 4° C., the test tube sealed by wax is taken out.

The extract of the cell intended to be analyzed 4 μl is added into 50 μl reagent. The cell extract contains about 0.5~2 μl total protein (equal to extract of 103~104 cells). The reagent consists of 50 μM dNTP, over 3000 cpm labeled TS primer, 360 nM unlabeled TSG4 primer, 1 μg Taq polymerase, and T-PCR buffer (10×T-PCR buffer: 200 mM Tris, 15 mM $MgCl_2$, 680 mM KCl, 0.5% Tween 20, 10 mM EGTA, pH 8.3). The sterilized secondary water used in the reaction should be treated by 0.1% DEPC (USB) for 24 hours and then sterilized in the sterilizer. This step is to remove RNase that affects reaction.

The cell extract and reagents are set into a 0.2 ml PCR tube and react at 30° C. for 30 mins so that telomerase in the analyzed cell extract extends the TSG4 primer. Then the whole reacted mixture is heated to 94° C. for 3 minutes. Next PCR conditions are 94° C. for 30 sec, 50° C. for 30 sec, and 72° C. for 1 min, repeated for 45 cycles. At last, one cycle reacts at 94° C. for 30 seconds, 50° C. for 30 seconds, 72° C. for 1 minute. Then the reaction is terminated. In a negative control group of the TRAP assay, 5 μl mg/ml RNase A is added. Take 50 μL reacted mixture treated by PCR reaction, mix with 10 μL DNA dye evenly. Take 50 μL mixed solution, loaded into 10% acrylamide gel and run electrophoresis at voltage of 125 Volt and current of 400 mA for 3 hours. Take and load 50 μL mixture onto 10% acrylamide gel and run agarose gel electrophoresis at 125 Volt, 400 mA for 3 hours. After the electrophoresis being complete, take the gel, mix with SYBR Green I (diluted 10000-fold) to stain molecules therein and being vibrated for 30 mins. The gel is visualized with UV light and a photograph of the gel is taken by a camera.

Screening Results of TRAP Assay

Figure 13:
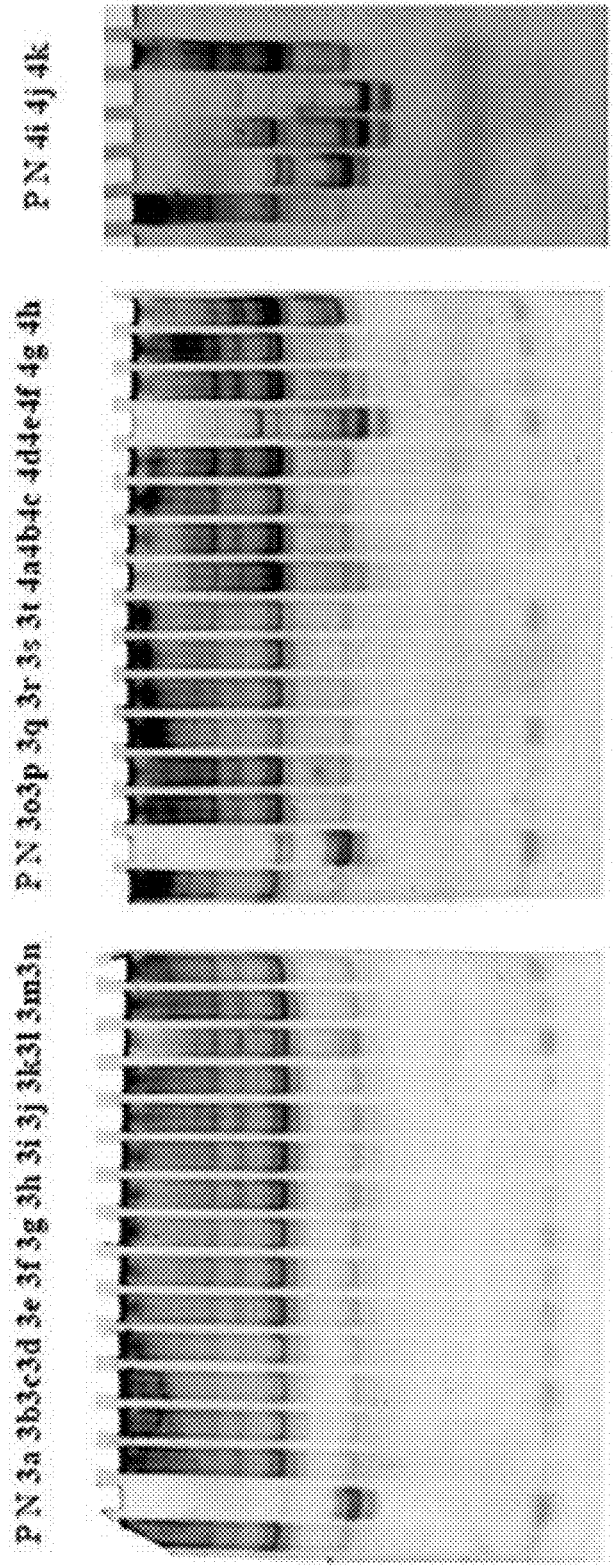
FIG. 13 shows screening results of anti-cancer compounds 3a-4k by TRAP assay at a concentration of 10 μM.

The screening results of TRAP assay are shown in FIG. 13. In the TRAP assay, the TSG4 primer itself will form G-quadruplex structure due to its telomere sequence theoretically. Once the compounds can stabilize the G-quadruplex structure, the telomerase is unable to react with the telomere. Thus telomerase inhibition is further achieved. Yet this test can't ensure whether the compounds inhibit the telomerase directly.

However, no matter through stabilization of G-quadruplex structure or direct telomerase inhibition, the final target is to find out compounds with effects of telomerase inhibition. In the gel electrophoresis results, the positive control group (P) is added with DMSO instead of the compound to perform analysis while the negative control group (N) uses 5 μL 0.1 mg/mL RNase A(CLONTECH) replaced the compound. In the positive control group (P), a plurality of telomere segments are produced while the negative control group (N) is not. In the primary screening, 1 mM sample is used. But due to poor water solubility, the compound may be precipitated. Thus samples in 10 μM are used. The compounds with effects of telomerase inhibition are compound 4e, compound 4i, and compound 4j.

Discussion and Conclusion

Chemical Synthesis

Discussion of Catalysts Used within the Processes a. pyridine: In acylation reaction, pyridine is added as catalyst. Because 1,8-aminoanthraquinone generates a large amount of hydrogen chloride(HCl), pyridine is used to neutralize HCl. On the other hand, pyridine activates nitrogen atoms on the aminoanthraquinone so as to make acylation reaction run more easily. While synthesizing compound 4 series, in the second step of connecting with the required amine, the reaction is getting easier to be complete once pyridine is used as the catalyst.

b. N,N-Diisopropylethylamine (DIPEA): DIPEA is used as a catalyst for connecting with amino acid side chain. The COOH-end of the commercial amino acid is protected by esterification and NH-end is hydrogen chloride (HCl) salt. Thus during chemical reaction, the NH-end should be activated and alkaline reagents are used as catalysts. During the processes, the solution is heated to 130° C. If the catalyst used is a strong alkaline, the ester bond on the COOH-end is hydrolyzed. Thus N,N-Diisopropylethylamine(DIPEA) is selected to be a proper catalyst.

c. Triethylamine(TEA): For synthesis of compounds 3 series, while connecting with desired amine, pyridine is firstly used as the catalyst. Later it is found that the products with higher purity are obtained once TEA is used as catalyst, together with high reaction temperature 130° C. for 30 minutes.

Discussion of Solvents and Temperature within the Processes

During acylation, the chloroacetyl chloride itself is a highreactive material that reacts with anthraquinone severely. At the same time, hydrogen chloride (HCl) is generated. Thus the addition of chloroacetyl chloride should be run in the ice-bath and then react at room temperature for 24 hours. When the compound 3 reacts with amino acids, the amino acids should be dissolved in DMF completely in advance, and then the compound 3 is added. Otherwise, the reaction will not be complete. During the reaction, the solution is set at 130° C. for at least one and a half hours and the reaction is complete. This is due to poor activity of NH-end protected by HCl. If the compound 3 is only connected with general amines, the reaction will complete at 130° C. only half an hour. The longer the reaction, the lower the yield rate. The compound 3 is quite difficult to be dissolved, even reflux heated for several days. Only in a pressured close mini-reactor, the compound 3 is dissolved under high temperature and high pressure. As to the compound 4, while connecting with general amines, DMF is used and the reaction is at 130° C. for half an hour. It is found that the product is difficult to be purified, even the reaction time is shortened. Next the solvent is changed to use THF, together with the mini-reactor, the reaction temperature is set at 60° C. for reducing collision velocity of the reaction and the reaction time is extended to 6 hours. The product with higher purity is obtained.

Purification and Product Yield Rate within the Processes:

In purification, recrystallization is performed with ethanol. Because compound 3 and compound 4 are unable to dissolve in alcohol, recrystallization from ethanol can filter initial reactants while purifying products. Refer to list two, compare the yield rate and it is found that yield rate of compounds 3c, 3f, 3l, 3m, 3n, 3r, 3s, 4a, 4f, 4g, and 4k with tertiary amines is higher than the compounds with secondary amines. It is supposed that the NH group on the side chain connected with the secondary amine works as a nucleophilic group to generate other side products. While the yield rate of the compounds 3a-3j, 3t connected with amino acids is a bit lower than the compounds connected with alkylamine, it is supposed that the prior compounds are with higher polarity so that part is dissolved in water while being extracted and this leads to reduction of the yield rate.

Discussion of Melting Point within the Processes:

The melting points of these compounds vary from one another, refer to list two. Most of compounds whose side chain is connected with a shorter straight chain have higher melting points. The longer the straight chain on the side chain, the lower the melting point. For example, 3m (194-195° C.)>3r(186-187° C.)>3s (159-166° C.). As to amino acids with larger molecular weight, the contact area between molecules is increased so that the intermolecular force is increased. This leads to higher melting point.

For example, 3g (238-239° C.)>3d (150-151° C.)>3h (119-120° C.).

Furthermore, the aromatic ring in the side chain also results in higher melting points. For example, 3j (119-120° C.), 3q (190-191° C.), 4c (190-191° C.). In addition, it is found that optical isomers such as 3d and 3e, 3h and 3i have similar melting points.

List two: derivatives of 1,8-diamidoanthraquinone

| Compd | R | Mp. (° C.) | Yield (%) |
|---|---|---|---|
| 3a | $NHCH_2CO_2CH_3$ | 173-174 | 42 |
| 3b | $NHCH(CH_2CH_2SCH_3)CO_2CH_3$ | 126-127 | 40 |
| 3c | $N(CH_2CH_2CH_2CH_2)CO_2CH_3$ | 170-171 | 60 |
| 3d | $NHCH(CH(CH_3)_2)CO_2CH_3$ | 150-151 | 47 |
| 3e | $(D)-NHCH(CH(CH_3)_2)CO_2CH_3$ | 150-151 | 35 |
| 3f | $N(CH_3)CH_2CO_2CH_3$ | 129-130 | 65 |
| 3g | $NHCH(CH_2CH(CH_3)_2)CO_2CH_3$ | 238-239 | 40 |
| 3h | $NHCH(CH_3)CO_2CH_3$ | 119-120 | 41 |
| 3i | $(D)-NHCH(CH_3)CO_2CH_3$ | 118-119 | 45 |
| 3j | $NHCH(C_6H_5)CO_2CH_3$ | 256-260 | 33 |
| 3k | $NHCH_2CH(CH_3)_2$ | 139-140 | 40 |
| 3l | $N(CH_2CH_3)_2$ | 228-229 | 70 |
| 3m | $N(CH_3)_2$ | 194-195 | 64 |
| 3n | $N(CH_2CH_2CH_3)_2$ | 129-130 | 82 |
| 3o | $NHCH(CH_3)_2$ | 196-197 | 65 |
| 3p | $NHCH_2CH_3$ | 182-183 | 52 |
| 3q | $3-(CF_3)C_6H_4CH_2NH$ | 190-191 | 66 |
| 3r | $N(CH_3)CH_2CH_3$ | 186-187 | 79 |
| 3s | $N(CH_3)CH_2CH_2CH_3$ | 159-160 | 67 |
| 3t | $NHCH(CH_2OCH(CH_3)_3)CO_2CH_3$ | 139-140 | 44 |
| 4a | $N(CH_2CH_3)_2$ | 160-161 (175-176)" | 72 |
| 4b | $NHCH_2CH(CH_3)_2$ | 224-225 | 54 |
| 4c | $3,5-F_2C_6H_3CH_2NH$ | 190-191 | 40 |
| 4d | $NHCH_2CH_2NHBoc$ | 101-102 | 30 |
| 4e | $NHCH_2CH_2N(CH_3)_2$ | 100-102 | 18 |
| 4f | $N(CH_3)_2$ | 116-117 (126)" | 74 |
| 4g | $N(CH_2CH_2CH_3)_2$ | 129-130 | 79 |
| 4h | $NHCH_3$ | 233-234 | 32 |
| 4i | $NHCH(CH_3)_2$ | 105-106 | 58 |
| 4j | $NHCH_2CH2CH_2N(CH_3)_2$ | 107-108 | 44 |
| 4k | $N(CH_3)CH_2CH_3$ | 129-130 | 76 |

Discussion of Optical Isomers of Disubstituted Peptidyl Anthraquinone by NMR Spectroscopy The optical isomers have quite similar physical properties (such as melting point and boiling point) and chemical properties. Thus it is noted from the data of the tests that hydrogen and carbon spectra of right- and left-handed isomers have very little difference. For example, refer to list 3, spectra of compound 3h contains a signal δ 1.46 that is assigned to H on C1 of the side chain while the spectra of compound 3i includes the same splitting signal with the compound 3h, split into a doublet. Next at δ 3.38 and δ 3.70, both are signals of H on C2 of the straight chain of the compounds 3h. Due to asymmetry of the molecules connected, the two hydrogens (H) on the C2 are different from and affecting each other so that the signal spit into two with similar coupling constants. Then the signal at δ 3.46 is assigned to H on C3 of the straight chain of the compound 3h and the compounds 3i includes the same signal at δ 3.46 with similar coupling constant. The signals split of H on C4 and H on aromatic ring of the compounds 3h, 3i are similar. The analysis of carbon spectra gets results similar to the hydrogen spectra. The chemical shifts of the compounds 3h, 3i are similar. During the synthesis processes, configuration of carbons of optical isomers has not been changed. In combination with data of melting points and data collected from the mass spectrometer, it is ensured that compounds 3h, 3i already have been synthesized. Other optical isomers 3d, 3e are also checked according to the way mentioned above.

List three: comparison of NMR spectra of optical isomers 3h,

3h

| $^1$H-NMR | $^{13}$C-NMR |
|---|---|
| δ 1.46 (d, J = 6.9 Hz, 6 H, —CH$_3$) | 18.29, 51.36, |
| δ 3.38 (d, J = 17.4 Hz, 2 H, —CH$_2$—), | 52.52, 55.94, |
| δ 3.46 (q, J = 6.9 Hz, 2 H, —CH—) | 118.18, 121.79, |
| δ 3.70 (d, J = 17.4 Hz, 2 H, —CH$_2$—) | 126.01, 132.67, |
| δ 3.75 (s, 6 H, —OCH$_3$) | 134.93, 140.69, |
| δ 7.77 (t, J = 7.8 Hz, 2 H, Ar—H$_{3,6}$) | 170.18(NCO), 174.86(CCO), |
| δ 8.06 (dd, J = 7.5 Hz, 1.2 Hz, 2 H, Ar—H$_{4,5}$) | 181.70(C$_9$O), 189.60(C$_{10}$O) |
| δ 9.23 (dd, J = 8.4 Hz, 1.2 Hz, 2 H, Ar—H$_{2,7}$) | |
| δ 12.84 (s, 2 H, Ar—NH—) | |

3i

| $^1$H-NMR | $^{13}$C-NMR |
|---|---|
| δ 1.45 (d, J = 7.2 Hz, 6 H, —CH$_3$) | 18.23, 51.28, |
| δ 3.38 (d, J = 17.4 Hz, 2 H, —CH$_2$—), | 52.45, 55.89, |
| δ 3.46 (q, J = 6.9 Hz, 2H, —CH—) | 118.03, 121.64, |
| δ 3.70 (d, J = 17.4 Hz, 2 H, —CH$_2$—) | 125.90, 132.54, |
| δ 3.75 (s, 6 H, —OCH$_3$) | 134.83, 140.63, |
| δ 7.77 (t, J = 7.8 Hz, 2 H, Ar—H$_{3,6}$) | 170.08(NCO), 174.77(CCO), |
| δ 8.06 (dd, J = 7.5 Hz, 1.2 Hz, 2 H, Ar—H$_{4,5}$) | 181.51(C$_9$O), 189.43(C$_{10}$O) |
| δ 9.24 (dd, J = 8.4 Hz, 1.2 Hz, 2 H, Ar—H$_{2,7}$) | |
| δ 12.85 (s, 2 H, Ar—NH—) | |

Pharmacological Tests
MTT Assay:

The results show that after the primary screening, compounds 3i, 3j, 3m, 3o, 3p, and 4a-4k (10 μM) have quite good inhibition effects on tumor cells GBM 8401, compounds 3j, 3k, 3n-3p, 3t, and 4a-4k (10 μM) also can inhibit growth of tumor cells GBM 8901. Most important of all, the cell viabilities of normal SVG p12 cells treated by the compounds 3i-3k, 3m, 3t, and 4c (10 μM) are all over 80% and these six compounds are drugs with great potential.

TRAP Assay a. When the compounds stabilize the G-quadruplex structure, telomerase is unable to extend the end of the chromosome. Thus the telomere segment will not be seen in the electrophoresis gel.

b. In the compounds being tested, the compounds at a concentration of 10 μM with effects of telomerase inhibition include compound 4e, compound 4l and compound 4j.

Discussion of Structure Activity Relationship:

a. Side Chain Length

It is found through pharmacological tests, the distance between amido group and the nitrogen atom on the side chain is preferred two carbon atoms long. This may be due to the chain length has effects on hydrogen bonding between the nitrogen atom on the end-group and the Guanine and further affects the stabilization ability of the compounds to G-quadruplex structure.

b. The End-Group

It is found by the MTT tests that the compounds with aromatic ring substitutes such as 3j~4c have better effects. However, this result is not evaluated exactly unless a series of aromatic ring substitutes are done. As to compounds whose end-group is connected with amino acid, the derivatives connected with (D)alaline, phenylalaline are more effective than others.

As to the compounds whose end-group is connected with tertiary nitrogen: in the tests, the compounds whose end-group is connected with tertiary such as 3e, 3j have effects of telomerase inhibition by the evaluation of TRAP assays. This may be due to higher affinity raised by ionic interaction between the nitrogen atom with positive charge on the end-group and the base. In contrast to telomerase inhibitors BR-ACO-19, dibenzo[b,j](1,7)phenathroline whose chemical structure is shown in FIG. 14, all of them have the same feature-a N,N-dimethyl group on the end thereof. The side chain of BR-ACO-19 further includes aromatic ring substitutes and this may increase its selectivity so that such side chain is a group with great potential for further research.

CONCLUSION

Thirty one compounds are synthesized according to the present invention.

1. In the MTT assay, a series of compounds 3 have lower cytotoxic effects on tumor cell and so does the normal cell. Among these compounds, the compounds 3i, 3j, 3k, 3m, and 3t are derivatives with great potential in tumor inhibition.

2. In the MTT assay, a series of compounds 4 have higher cytotoxic effects on tumor cell and so does the normal cell while the compound 4c is a more potent inhibitor.

3. In the TRAP assay, the compounds 3e, 4i, 4j are derivatives with effects of telomerase inhibition.

In summary, anti-cancer compounds and manufacturing methods thereof are provided by the present invention. The anti-cancer compounds are a series of 1,8-diamidoanthraquinone derivatives with amino compounds having a novel chemical structure that can inhibit growth/proliferation of tumor cells and overcome shortcomings of conventional anti-cancer drug-doxorubincine such as serious cardiac toxicity.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:

1. A compound of the structure:

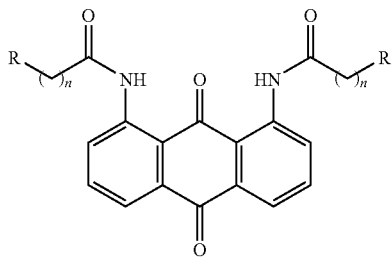

wherein n=1 and R is selected from the group consisting of:
$NHCH_2CO_2CH_3$ (3a),
$NHCH(CH_2CH_2SCH_3)CO_2CH_3$ (3b),
$(NCH_2CH_2CH_2CH)CO_2CH_3$ (3c),
|_____|
(L)-$NHCH(CH(CH_3)_2)CO_2CH_3$ (3d),
(D)-$NHCH(CH(CH_3)_2)CO_2CH_3$ (3e)
$N(CH_3)CH_2CO_2CH_3$ (3f)
(L)-$NHCH(CH_2CH)(CH_3)_2)CO_2CH_3$ (3g),
(D)-$NHCH(CH_3)CO_2CH_3$ (3i),
$NHCH(C_6H_5)CO_2CH_3$ (3j),
3-$(CF_3)C_6H_4CH_2NH$ (3q) and
$NHCH(CH_2OCH(CH_3)_3)_3)CO_2CH_3$ (3t);
and
wherein n=2, R is selected group consisting of:
3,5-$F_2C_6H_3CH_2NH$ (4c),
$NH(CH_2)_3NHCO_2C(CH_3)_3$ (4d),
$NH(CH_2)_2N(CH_3)_2$ (4e) and
$NHCH_2CH_2CH_2N(CH_3)_2$ (4j).

* * * * *

SEQUENCE LISTING

```
<160> NUMBER OF SEQ ID NOS: 3

<210> SEQ ID NO 1
<211> LENGTH: 23
<212> TYPE: DNA
<213> ORGANISM: Unknown
<220> FEATURE:
<223> OTHER INFORMATION: The sequence is synthesized

<400> SEQUENCE: 1
gggattggga ttgggattgg gtt                                        23

<210> SEQ ID NO 2
<211> LENGTH: 23
<212> TYPE: DNA
<213> ORGANISM: Unknown
<220> FEATURE:
<223> OTHER INFORMATION: The sequence is synthesized

<400> SEQUENCE: 2
gggattggga ttgggattgg gtt                                        23

<210> SEQ ID NO 3
<211> LENGTH: 24
```